US012630811B2

(12) United States Patent
Raj et al.

(10) Patent No.: US 12,630,811 B2
(45) Date of Patent: May 19, 2026

(54) LACTASE ENZYMES WITH IMPROVED PROPERTIES AT ACIDIC PH

(71) Applicant: Chr. Hansen A/S, Hoersholm (DK)

(72) Inventors: Hans Raj, Hoersholm (DK); Johannes Maarten Van Den Brink, Hoersholm (DK); Christian Gilleladen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 294 days.

(21) Appl. No.: 17/285,288

(22) PCT Filed: Oct. 17, 2019

(86) PCT No.: PCT/EP2019/078150
§ 371 (c)(1),
(2) Date: Apr. 14, 2021

(87) PCT Pub. No.: WO2020/079116
PCT Pub. Date: Apr. 23, 2020

(65) Prior Publication Data
US 2021/0348147 A1 Nov. 11, 2021

(30) Foreign Application Priority Data
Oct. 17, 2018 (EP) ..................................... 18200994

(51) Int. Cl.
*C12N 9/38* (2006.01)
*A23B 11/12* (2025.01)
*A23C 9/12* (2006.01)

(52) U.S. Cl.
CPC ............ *C12N 9/2471* (2013.01); *A23B 11/12* (2025.01); *A23C 9/1206* (2013.01); *C12Y 302/01023* (2013.01)

(58) Field of Classification Search
CPC ..... A23C 9/123; A23C 9/1232; A23C 9/1234; A23C 9/1236; A23C 9/1238; A23C 9/127; A23C 9/1275; A23C 9/1206; C12N 9/2471
See application file for complete search history.

(56) References Cited

U.S. PATENT DOCUMENTS

| | | | |
|---|---|---|---|
| 8,030,049 B2 | 10/2011 | Tzortzis et al. | |
| 10,058,107 B2 | 8/2018 | Hendriksen et al. | |
| 10,306,902 B2 | 6/2019 | Hendriksen et al. | |
| 10,555,541 B2 | 2/2020 | Hendriksen et al. | |

(Continued)

FOREIGN PATENT DOCUMENTS

| | | |
|---|---|---|
| EP | 1 227 152 A1 | 7/2002 |
| EP | 2 530 148 A1 | 12/2012 |

(Continued)

OTHER PUBLICATIONS

Banerjee, "Is divalent magnesium cation the best cofactor for bacterial beta-galactosidase?", J. Biosci. 2018, 43 (5), pp. 941-945 (hereinafter referred to as Banerjee). (Year: 2018).*

(Continued)

*Primary Examiner* — Changqing Li
(74) *Attorney, Agent, or Firm* — Yoshimi D. Barron

(57) ABSTRACT

The present invention relates to new improved peptide or dimeric peptides exhibiting betagalactosidase enzyme activity wherein the peptide has a pH optimum at acidic conditions.

15 Claims, 1 Drawing Sheet
Specification includes a Sequence Listing.

Ratio of activity at different pHs

(56) References Cited

U.S. PATENT DOCUMENTS

| | | | |
|---|---|---|---|
| 11,525,129 B2 | 12/2022 | Raj et al. | |
| 2009/0110770 A1 | 4/2009 | Tzortzis et al. | |
| 2009/0117080 A1 | 5/2009 | Tzortzis et al. | |
| 2009/0297660 A1 | 12/2009 | Silver et al. | |
| 2010/0113383 A1 | 5/2010 | Mills et al. | |
| 2010/0285175 A1 | 11/2010 | Hendriksen et al. | |
| 2012/0058223 A1 | 3/2012 | Stougaard et al. | |
| 2016/0333331 A1 | 11/2016 | De Jong et al. | |
| 2017/0215449 A1* | 8/2017 | Nagahata | A23C 9/152 |
| 2019/0343138 A1 | 11/2019 | Ba et al. | |
| 2020/0120946 A1 | 4/2020 | Hendriksen et al. | |
| 2020/0123519 A1 | 4/2020 | Bongiorni et al. | |
| 2021/0032615 A1 | 2/2021 | Raj et al. | |
| 2021/0037844 A1 | 2/2021 | Hendriksen et al. | |
| 2021/0355471 A1 | 11/2021 | Raj et al. | |
| 2023/0210121 A1 | 7/2023 | Raj et al. | |

FOREIGN PATENT DOCUMENTS

| | | | |
|---|---|---|---|
| EP | 2 957 180 B1 | 12/2015 | |
| RU | 2278160 C2 | 9/2005 | |
| RU | 2009120742 | 12/2010 | |
| WO | WO-2005/084411 A2 | 9/2005 | |
| WO | WO-2005/086794 A2 | 9/2005 | |
| WO | WO-2007/088324 A1 | 8/2007 | |
| WO | WO-2007/110619 A1 | 10/2007 | |
| WO | WO-2008/033520 A2 | 3/2008 | |
| WO | WO-2009/009142 A2 | 1/2009 | |
| WO | WO-2009/071539 A1 | 6/2009 | |
| WO | WO-2010/092057 A1 | 8/2010 | |
| WO | WO-2013/160413 A1 | 10/2013 | |
| WO | WO-2015/107050 A1 | 7/2015 | |
| WO | WO-2017/216000 A1 | 12/2017 | |
| WO | WO-2018041869 A1 * | 3/2018 | A23C 3/031 |
| WO | WO-2018/130630 A1 | 7/2018 | |
| WO | WO-2018/187524 A1 | 10/2018 | |
| WO | WO-2018/189224 A1 | 10/2018 | |
| WO | WO-2018/189238 A1 | 10/2018 | |
| WO | WO-2018/189242 A1 | 10/2018 | |

OTHER PUBLICATIONS

Genbank Accession KRO12099 (https://www.ncbi.nlm.nih.gov/protein/KRO12099.1?report=genbank&log$=protalign&blast_rank=1&RID=NRM8Y7MN016; publication date Nov. 6, 2015 (Year: 2015).*

UniprotKB Accession B2GAA1 (https://rest.uniprot.org/unisave/B2GAA1?format=txt&versions=1; publication date Jun. 10, 2008). (Year: 2008).*

"beta-galactosidase [Lactobacillus gasseri]"; NCBI Reference Sequence: WP_049161922.1; NCBI; https:// https://www.ncbi.nlm.nih.gov/protein/896142157?sat=48&satkey=130325244; Jul. 19, 2015; 1 page (Year: 2015).*

"beta-galactosidase [Bifidobacterium adolescentis]"; UniprotKB/TrEMBL Accession No. A0A174BHI7; UniprotKB/TrEMBL; https://rest.uniprot.org/unisave/A0A174BHI7?format=txt&versions=1, Sep. 7, 2016 (Year: 2016).*

"beta-galactosidase [Lactobacillus acidophilus]"; NCBI Reference Sequence: WP_011254434.1; NCBI; https://www.ncbi.nlm.nih.gov/protein/499573651?sat=47&satkey=80782391; May 15, 2013 (Year: 2013).*

Broune et al. "Catalytic Plasticity of Fatty Acid Modification Enzymes Underlying Chemical Diversity of Plant Lipids," Science, vol. 282, pp. 1315-1317 (1998).

Devos et al., "Practical Limits of Function Prediction," Proteins: Structure, Function, and Genetics, vol. 41, pp. 98-107 (Aug. 2000).

Seffernick et al., "Melamine Deaminase and Atrazine Chlorohydrolase: 98 Percent Identical but Functionally Different," Journal of Bacteriology, vol. 183, No. 8, pp. 2405-2410 (Apr. 2001).

Whisstock et al., "Prediction of protein function from protein sequence and structure," Quarterly Reviews of Biophysics, vol. 36, No. 3 (pp. 307-340) (2003).

Witkowski et al. "Conversion of β-Ketoacyl Synthase to a Malonyl Decarboxylase by Replacement of the Active-Site Cysteine with Glutamine," Biochemistry, vol. 38, pp. 11643-11650 (1999).

U.S. Appl. No. 17/986,618, filed Nov. 14, 2022, Raj et al.

Skripnyuk A.A., et al.; "Modern methods for producing beta-galactosidase"; Science Innovations Technologies, 3; 2014; pp. 198-204.

GenBank Accession No. CAI98003.1.

Kreft et al., "Lactose hydrolysing ability of sonicated cultures of Lactobacillus delbrueckii ssp. bulgaricus 11842," Le Lait, vol. 81, No. 3, pp. 355-364 (Jan. 2001).

Office Action issued on Apr. 12, 2022 in U.S. Appl. No. 16/998,706 (US 2021-0032615).

Office Action issued on Apr. 29, 2022 in U.S. Appl. No. 16/604,129 (US 2021-0355471).

Rhimi et al., "Exploring the acidotolerance of B-galactosidase from Lactobacillus delbrueckii subsp. bulgaricus: an attractive enzyme for lactose bioconversion," Research in Microbiology, vol. 160, pp. 775-784 (Sep. 2009).

UniProt Accession No. F0K2P6, May 3, 2011.

UniProt Accession No. G6F860, Jan. 25, 2012.

Guo et al., "Protein tolerance to random amino acid change," PNAS, vol. 101, No. 25, pp. 9205-9210 (Jun. 2004).

Keskin et al., "A new, structurally nonredundant, diverse data set of protein-protein interfaces and its implications," Protein Science, vol. 13, pp. 1043-1055 (2004).

Klimova E.V. Advantages of using beta-galactosidase for hydrolysis of lactose and obtaining galactooligosaccharides; prospects for the use of the obtained products in industrial food technologies, Food and processing industry, Abstract journal, No. 4, 2008, p. 1269.

Ogurtsov A.N., Methods of bioinformatic analysis, Textbook, Kharkov, 2011, NTU "KhPI", pp. 4-5, 25.

Singer et al., "Genes & Genomes, A changing Perspective," University Science Books Mill Valley, CA (1998).

UniProt Accession Nos. TrEMBL, A7A6G3_BIFAD, Sep. 11, 2007, Q38UW6_LACSS, Nov. 22, 2005, Q38UW7_LACSS, Nov. 22, 2005, R5YYAO_9LACO, Jul. 24, 2013, F0TG79_LACAM, May 3, 2011, K2MWD3_BIFBI, Nov. 28, 2012, D4QFE8_BIFBI, Jul. 15, 2012, A0A133L394_BIFBR, Jul. 8, 2016, A0A1VSPPN6_9BIFI, Jul. 7, 2017, A0A1Q6ESN3_9BIFI, Apr. 12, 2016, A0A045FVZ6_LACDE, Mar. 16, 2017, 0A1L3JVR5_LACDL, Mar. 15, 2017, F0K2P6_LACD2, May 3, 2011 A0A0D5MI45_LACHE, May 27, 2015, A0A0D5MHU_LACHE, May 27, 2015, A0A1V8RDS6_BIFIN, Jun. 7, 2017, B3XQL8_LACRI, Sep. 23, 2008, B3XQL9_LACRI, Sep. 23, 2008, U6F4Q6_LACHE, Jan. 22, 2014, A8YWAO_LACH4, Jan. 15, 2008, LOCMGO_9LACO, Mar. 6, 2016, A0A0M410A2_STRR, Dec. 9, 2015, A0A0CORIHO_9LACO, Nov. 11, 2015, 0A174B8K1_BIFAD, Apr. 7, 2016.

Office Action and Search Report issued on May 14, 2021 in Russian Application No. 2019134223/10.

UniProtKB—A0A076JKA5 (A0A076JKA5_BIFAD); Oct. 29, 2014; 7 pages.

UniProtKB—A0A0A1GLP4 (A0A0A1GLP4_BIFLN); Feb. 4, 2015; 8 pages.

UniProtKB—A0A0A715K5 (A0A0A715K5_9BIFI); Mar. 4, 2015; 8 pages.

UniProtKB—A0A0H2P357 (A0A0H2P357_BIFBI); Sep. 16, 2015; 7 pages.

UniProtKB—A0A0U5FVZ6 (A0A0U5FVZ6_LACDE); Mar. 16, 2016; 9 pages.

UniProtKB—A0A126SWK6 (A0A126SWK6_9BIFI); Jul. 6, 2016; 8 pages.

UniProtKB—A0A174BAQ4 (A0A174BAQ4_9BIFI); Sep. 7, 2016; 8 pages.

UniProtKB—A0A174BB61 (A0A174BB61_BIFAD); Sep. 7, 2016; 8 pages.

UniProtKB—A0A174BH17 (A0A174BH17_9FIRM); Sep. 7, 2016; 5 pages.

UniProtKB—A0A1D7UM07 (A0A1D7UM07_BIFLN); Jan. 18, 2017; 8 pages.

UniProtKB—A0A1D7ZXL7 (A0A1D7ZXL7_LIMFE); Jan. 18, 2017; 7 pages.

(56)  References Cited

OTHER PUBLICATIONS

UniProtKB—A0A1S2W2V3 (A0A1S2W2V3_BIFLN); Apr. 12, 2017; 8 pages.
UniProtKB—A0A1X2Z956 (A0A1X2Z956_BIFAD); Jul. 5, 2017; 8 pages.
UniProtKB—A0A1X2ZA47 (A0A1X2ZA47_BIFAD); Jul. 5, 2017; 7 pages.
UniProtKB—A0A1X2ZAP4 (A0A1X2ZAP4_BIFAD); Jul. 5, 2017; 7 pages.
UniProtKB—A0A2G5Q4A6 (A0A2G5Q4A6_9BIFI); Jan. 31, 2018; 8 pages.
UniProtKB—A0A4R0SL12 (A0A4R0SL12_BIFLN); Jul. 31, 2019; 8 pages.
UniProtKB—A0A4R0U1N4 (A0A4R0U1N4_BIFLN); Jul. 31, 2019; 8 pages.
UniProtKB—A0A6A2R535 (A0A6A2R535_BIFAD); Jun. 17, 2020; 7 pages.
UniProtKB—A0A6B1X5Q7 (A0A6B1X5Q7_9BIFI); Jun. 17, 2020; 6 pages.
UniProtKB—A0A6I1DQE1 (A0A6I1DQE1_BIFLN); Aug. 12, 2020; 8 pages.
UniProtKB—A0A6L4K944 (A0A6L4K944_BIFAD); Oct. 7, 2020; 7 pages.
UniProtKB—A0A6L4V5B5 (A0A6L4V5B5_9BIFI); Oct. 7, 2020; 8 pages.
UniProtKB—A0A7D9N5G4 (A0A7D9N5G4_LACJH); Dec. 2, 2020; 8 pages.
UniProtKB—A0A829LWJ6 (A0A829LWJ6_LIMFE); Sep. 29, 2021; 7 pages.
UniProtKB—A5VKG8 (A5VKG8_LIMRD); Jul. 10, 2007; 8 pages.
UniProtKB—B2GAA1 (B2GAA1_LIMF3); Jun. 10, 2008; 7 pages.
UniProtKB—B2GAA2 (B2GAA2_LIMF3); Jun. 10, 2008; 6 pages.
UniProtKB—D6ZY97 (D6ZY97_BIFLJ); Aug. 10, 2010; 8 pages.
UniProtKB—E4SLB1 (E4SLB1_LACAR); Feb. 8, 2011; 8 pages.
UniProtKB—E8MRV2 (E8MRV2_BIFL1); Apr. 5, 2011; 8 pages.
UniProtKB—F0HTF8 (F0HTF8_LACDL); May 3, 2011; 9 pages.
UniProtKB—F0TG75 (F0TG75_LACAM); May 3, 2011; 8 pages.
UniProtKB—F2M1D8 (F2MID8_LACAL); May 11, 2011; 8 pages.
UniProtKB—F4AFP0 (F4AFP0_LACJH); Jun. 28, 2011; 8 pages.
UniProtKB—F8ASA8 (F8ASA8_BIFLN); Sep. 21, 2011; 8 pages.
UniProtKB—G6F860 (G6F860_LACDE); Jan. 25, 2012; 9 pages.
UniProtKB—I3WJ66 (I3WJ66_BIFBI); Sep. 5, 2012; 8 pages.
UniProtKB—K2I5J0 (K2I5J0_BIFBI); Nov. 28, 2012; 8 pages.
UniProtKB—Q5FJD5 (Q5FJD5_LACAC); Mar. 1, 2005; 9 pages.
UniProtKB—Q74KL4 (Q74KL4_LACJO); Jul. 5, 2004; 8 pages.
UnitProtKB—D9ZDZ1 (D9ZDZ1_9ZZZZ); Oct. 5, 2010; 7 pages.
Database GenBank: ACE06986.1, (Jun. 8, 2012).
Database GenBank: CDR82630.1, (Jun. 11, 2014).
U.S. Appl. No. 16/604,129, filed Oct. 9, 2019, Raj et al.
U.S. Appl. No. 16/604,133, filed Oct. 9, 2019, Raj et al.
U.S. Appl. No. 16/604,134, filed Oct. 9, 2019, Raj et al.
"Chapter 3 Lactose content of milk and milk products," The American Journal of Clinical Nutrition, vol. 48, No. 4 pp. 1099-1104 (Oct. 1988) Available online, URL: https://academic.oup.com/ajcn/article/abstract/48/4/1099/4791817?redirectedFrom=fulltext.
"UNIPROT: A0AOB5BJ47" (Apr. 1, 2015), Retrieved from the Internet, URL:http://ibis/exam/dbfetch.jsp?id=UNIPROT:A0A0B5J47 (Retrieved on May 11, 2017).
"UNIPROT: A0A0S2MCC8—beta galactosidase," (Feb. 17, 2016) Retrieved from the Internet, URL: https://ibis/exam/dbfetch.jsp?id=UNIPROT:A0A0S2MCC8 [retrieved on Mar. 9, 2018].
Horner et al., "β-Galactosidase activity of commercial lactase samples in raw and pasteurized milk at refrigerated temperatures," J. Dairy Sci. 94: 3242-3249 (2011).
Kreft et al., "Lactose hydrolysing ability of sonicated cultures of Lactobacillus delbrueckii ssp. bulgaricus 11842," Le Lait, INRA Editions 81(3) pp. 355-364 (2001).

Nakagawa et al., "Overexpression and functional analysis of cold-active β-galactosidase from Arthrobacter psychrolactophilus strain F2," Protein Expression and Purification 54 (2007) 295-299 (Available on line Mar. 2007).
Office Action issued on Jan. 22, 2021, in U.S. Appl. No. 16/998,706 (US 2021-0032615).
Office Action issued on Jun. 9, 2021, in U.S. Appl. No. 16/998,706 (US 2021-0032615).
Palak-Szukalska et al., "A novel cold-active β-D-galactosidase with transglycosylation activity from the Antarctic Arthrobacter sp. 32cB—Gene cloning, purification and characterization," Process Biochemistry 49 (2014) 2122-2133 (Available online Sep. 28, 2014).
Rhimi et al., "Exploring the acidotolerance of β-galactosidase from Lactobacillus delbrueckii subsp. bulgaricus: an attractive enzyme for lactose bioconversion," Research in Microbiology, vol. 160 pp. 775-784 (2009) (Available online Sep. 2009).
Schmidt et al., "Identification, cloning and expression of a cold-active β-galactosidase from a novel Arctic bacterium, Alkalilactibacillus ikkense," (2010) Environmental Technology, 31:10, 1107-1114 (Published online Jun. 2010).
UNIPROT:G6F860_LACDE (Oct. 2020).
Van De Guchte, et. al., "Beta-galactosidase [Lactobacillus delbrueckii subsp. bulgaricus ATCC 11842=JCM 1002]" GenBank: CAI98003.1 [Feb. 2015].
Wang et al., "A novel cold-adapted β-galactosidase isolated from Halomonas sp. S62: gene cloning, purification and enzymatic characterization," World J. Microbiol Biotechnol (2013) 29:1473-1480 (Published on line Mar. 2013).
Wierzbicka-Wośet al., "A novel cold-active 3-D-galactosidase from the Paracoccus sp. 32d - gene cloning, purification and characterization," Microbial Cell Factories 2011, 10:108 pp. 1-12.
Biocceleration Ltd.; Seq Alignment Result (U.S. Appl. No. 16/604,134 SEQ #7 vs Tzortis et al. (US2009/0110770); Seq #2 using SLIC and ABSS SEQ-to SEQ (aa); Jun. 27, 2023.
Nguyen, Thao Thi et al.; "Effect of mutations to amino acid A301 and F361 in thermostability and catalytic activity of the β-galactosidase from Bacillus subtilis VTCC-DVN-12-01"; BMC Biochemistry (2016) 17:15; Jul. 2016; 11 pages.
Patent Office of the Russian Federation: Federal Institute of Industrial Property; Office Action (Enquiry); Russian Patent Application No. 2021112325/10(026315) (English translation); Jun. 19, 2023; 10 pages.
Seffernick, Jennifer et al.; "Melamine Deaminase and Atrazine Chlorohydrolase: 98 Percent Identical but Functionally Different"; Journal of Bacteriology, vol. 183, No. 8; Apr. 2001; pp. 2405-2410.
Whisstock, James C. et al.; "Prediction of protein function from protein sequence and structure"; Quarterly Review of Biophysics 36, 3; Aug. 2003; pp. 307-340.
"Beta-galactosidase [Bifidobacterium angulatum]"; NCBI Reference Sequence: WP_033508907.1; NCBI; https://www.ncbi.nlm.nih.gov/protein/WP_033508907.1?report=genbank&log$=prottop&blast_rank=1&RID=STY73TRP013; Nov. 7, 2014; 1 page.
"Beta-galactosidase [Bifidobacterium bifidum]"; NCBI Reference Sequence: ALE11829.1; NCBI; https://www.ncbi.nlm.nih.gov/protein/ALE11829.1?report=genbank&log$=prottop&blast_rank=1&RID=STXB9JWN016; Sep. 14, 2015; 2 pages.
"Beta-galactosidase [Bifidobacterium longum]"; NCBI Reference Sequence: WP_013582379.1; NCBI; https://www.ncbi.nlm.nih.gov/protein/WP_013582379.1?report=genbank&log$=prottop&blast_rank=1&RID=STXT9S92016; May 18, 2013; 1 page.
"Beta-galactosidase [Lactobacillus amylovorus]"; NCBI Reference Sequence: WP_013438360.1; NCBI; https://www.ncbi.nlm.nih.gov/protein/WP_013438360.1?report=genbank&log$=prottop&blast_rank=1&RID=STWKFN82013; May 18, 2013; 1 page.
"Beta-galactosidase [Limosilactobacillus reuteri]"; NCBI Reference Sequence: WP_003666991.1; NCBI; https://www.ncbi.nlm.nih.gov/protein/WP_003666991.1?report=genbank&log$=prottop&blast_rank=1&RID=STXX2K05013; Jul. 31, 2013; 1 page.
Odamaki, Toshitaka et al.; "Comparative Genomics Revealed Genetic Diversity and Species/Strain-Level Differences in Carbohydrate

(56)         References Cited

OTHER PUBLICATIONS

Metabolism of Three Probiotic Bifidobacterial Species"; International Journal of Genomics, vol. 2015, article ID 567809; Jul. 2015; 12 pages.

Cecchini et al.; OM protein—protein search, using sw model; GenCore version 6.4.2; run on Jan. 31, 2022; title: US-16-604-129A-22; 6 pages.

* cited by examiner

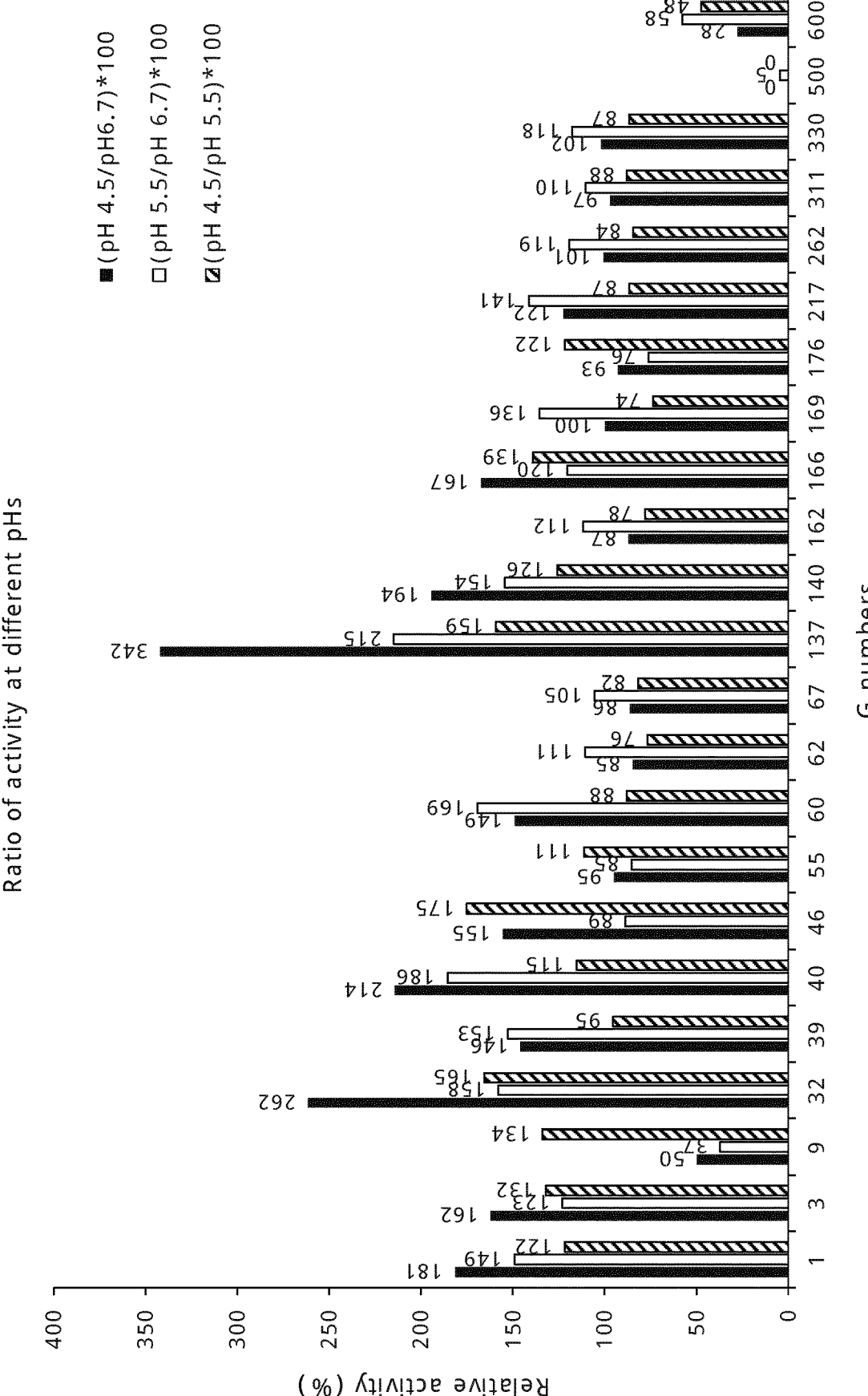

SEQUENCE LISTING

<160> NUMBER OF SEQ ID NOS: 28

<210> SEQ ID NO 1
<211> LENGTH: 698
<212> TYPE: PRT
<213> ORGANISM: Bifidobacterium adolescentis

<400> SEQUENCE: 1

```
Met Arg Arg Asn Phe Glu Trp Pro Lys Leu Leu Thr Ala Asp Gly Arg
1               5                   10                  15

Gly Ile Ala Phe Gly Gly Asp Tyr Asn Pro Asp Gln Trp Ser Glu Asp
            20                  25                  30

Ile Trp Asp Asp Asp Ile Arg Leu Met Lys Gln Ala Gly Val Asn Thr
        35                  40                  45

Val Ala Leu Ala Ile Phe Ser Trp Asp Arg Ile Gln Pro Thr Glu Asp
    50                  55                  60

Arg Trp Asp Phe Gly Trp Leu Asp Arg Ile Ile Asp Lys Leu Gly Asn
65                  70                  75                  80

Ala Gly Ile Ala Val Asp Leu Ala Ser Ala Thr Ala Thr Ala Pro Leu
                85                  90                  95

Trp Leu Tyr Glu Ser His Pro Glu Val Leu Pro Arg Asp Lys Tyr Gly
            100                 105                 110

His Pro Val Asn Ala Gly Ser Arg Gln Ser Trp Ser Pro Thr Ser Pro
            115                 120                 125

Val Phe Lys Glu Tyr Ala Leu Thr Leu Cys Arg Lys Leu Ala Glu Arg
    130                 135                 140

Tyr Gly Thr Asn Pro Tyr Val Thr Ala Trp His Met Gly Asn Glu Tyr
145                 150                 155                 160

Gly Trp Asn Asn Arg Glu Asp Tyr Ser Asp Asn Ala Leu Asp Ala Phe
                165                 170                 175

Arg Ala Trp Cys Arg Arg Lys Tyr Gly Thr Ile Gly Ala Leu Asn Gln
            180                 185                 190

Ala Trp Gly Thr Thr Phe Trp Gly Gln Glu Met Asn Gly Phe Asp Glu
            195                 200                 205

Val Leu Ile Pro Arg Phe Met Gly Ala Asp Ser Met Val Asn Pro Gly
    210                 215                 220

Gln Lys Leu Asp Phe Glu Arg Phe Gly Asn Asp Met Leu Leu Asp Phe
225                 230                 235                 240

Tyr Lys Ala Glu Arg Asp Ala Ile Ala Glu Ile Cys Pro Asp Lys Pro
                245                 250                 255

Phe Thr Thr Asn Phe Met Val Ser Thr Asp Gln Cys Cys Met Asp Tyr
            260                 265                 270

Ala Ala Trp Ala Glu Glu Val Asn Phe Val Ser Asn Asp His Tyr Phe
            275                 280                 285

His Glu Gly Glu Ser His Leu Asp Glu Leu Ala Cys Ser Asp Ala Leu
    290                 295                 300

Met Asp Ser Leu Ala Leu Gly Lys Pro Trp Tyr Val Met Glu His Ser
305                 310                 315                 320

Thr Ser Ala Val Gln Trp Lys Pro Leu Asn Thr Arg Lys Arg Lys Gly
                325                 330                 335

Glu Thr Val Arg Asp Ser Leu Ala His Val Ala Met Gly Ala Asp Ala
            340                 345                 350

Ile Asn Phe Phe Gln Trp Arg Ala Ser Ala Phe Gly Ala Glu Ser Phe
            355                 360                 365
```

-continued

```
His Ser Ala Met Val Pro His Ala Gly Glu Asp Thr Lys Leu Phe Arg
    370             375             380

Gln Val Cys Glu Leu Gly Ala Ser Leu His Thr Leu Ala Asp Ala Gly
385             390             395             400

Val Gln Gly Thr Glu Leu Ala His Ser Asp Thr Ala Ile Leu Phe Ser
            405             410             415

Ala Glu Ser Glu Trp Ala Thr Arg Ser Gln Thr Leu Pro Ser Met Lys
            420             425             430

Leu Asn His Trp His Asp Val Arg Asp Trp Tyr Arg Ala Phe Leu Asn
            435             440             445

Ala Gly Ser Arg Ala Asp Ile Val Pro Leu Ala Tyr Asp Trp Ser Ser
    450             455             460

Tyr Lys Thr Val Val Leu Pro Thr Val Leu Ile Leu Ser Ala Ala Asp
465             470             475             480

Thr Gln Arg Leu Ala Asp Phe Ala Ala Ala Gly Gly Arg Val Val Val
            485             490             495

Gly Tyr Ala Thr Gly Leu Ile Asp Glu His Phe His Thr Trp Leu Gly
            500             505             510

Gly Tyr Pro Gly Ala Gly Asp Gly Leu Leu Arg Ser Met Leu Gly Val
            515             520             525

Arg Gly Glu Glu Phe Asn Ile Leu Gly Ala Glu Ala Glu Gly Glu Pro
    530             535             540

Gly Glu Ile Arg Leu Ser Ser Ala Asp Asp Ser Ala Ala Leu Asp Gly
545             550             555             560

Thr Thr Thr Arg Leu Trp Gln Asn Asp Val Asn Val Thr Gly Glu His
            565             570             575

Ala Gln Val Leu Ala Thr Tyr Ala Gly Glu Glu Ala Asp Glu Trp Glu
            580             585             590

Leu Asp Gly Thr Ala Ala Val Thr Arg Asn Pro Tyr Gly Ser Gly Glu
            595             600             605

Ala Tyr Phe Val Gly Cys Asp Leu Asp Val Ala Asp Leu Thr Lys Leu
    610             615             620

Val Arg Ala Tyr Leu Ala Ala Pro Ser Gln Asp Asn Ala Asp Val Leu
625             630             635             640

His Thr Val Arg Glu Ser Ala Asp Ala Thr Phe Asp Phe Tyr Leu Pro
            645             650             655

Arg Gly Lys Glu Thr Val Glu Leu Gln Gly Ile Glu Gly Glu Pro Val
            660             665             670

Ile Leu Phe Gln Thr Glu Arg Gly Lys Lys Pro Gly Ser Tyr Thr Val
            675             680             685

His Arg Asn Gly Val Leu Val Val Arg Arg
    690             695
```

```
<210> SEQ ID NO 2
<211> LENGTH: 690
<212> TYPE: PRT
<213> ORGANISM: Bifidobacterium adolescentis

<400> SEQUENCE: 2

Met Asn Gln Arg Arg Glu His Arg Trp Pro Arg Pro Leu Glu Gly Arg
1               5               10              15

Arg Ala Arg Ile Trp Tyr Gly Gly Asp Tyr Asn Pro Asp Gln Trp Pro
            20              25              30

Glu Glu Val Trp Asp Glu Asp Val Arg Leu Met Val Lys Ala Gly Val
            35              40              45
```

```
Asn Leu Val Ser Val Gly Ile Phe Ser Trp Ala Lys Ile Glu Pro Arg
    50                  55                  60

Glu Asp Met Tyr Asp Phe Gly Trp Leu Asp Arg Ile Ile Asp Lys Leu
65                  70                  75                  80

Gly Lys Ala Gly Ile Ala Val Asp Leu Ala Ser Ala Thr Ala Ser Pro
                85                  90                  95

Pro Met Trp Leu Thr Gln Ala His Pro Glu Val Leu Trp Lys Asp Tyr
                100                 105                 110

Arg Gly Asp Val Cys Gln Pro Gly Ala Arg Gln His Trp Arg Pro Thr
                115                 120                 125

Ser Pro Val Phe Cys Glu Tyr Ala Leu Lys Leu Cys Arg Ala Met Ala
    130                 135                 140

Glu His Tyr Lys Asp Asn Pro Tyr Val Val Ala Trp His Val Gly Asn
145                 150                 155                 160

Glu Tyr Gly Cys His Asn Arg Phe Asp Tyr Ser Glu Asp Ala Glu Arg
                165                 170                 175

Ala Phe Gln Asp Trp Cys Glu Glu Arg Tyr Gly Thr Ile Glu Ala Val
                180                 185                 190

Asn Asp Ala Trp Gly Thr Ala Phe Trp Ala Gln His Leu Asn Asp Phe
                195                 200                 205

Ser Glu Ile Val Pro Pro Arg Phe Ile Gly Asp Gly Asn Phe Met Asn
    210                 215                 220

Pro Gly Lys Leu Leu Asp Phe Lys Arg Phe Ser Ser Asp Ala Leu Lys
225                 230                 235                 240

Ser Phe Tyr Val Ala Glu Arg Asp Ala Leu Ala Glu Ile Thr Pro Glu
                245                 250                 255

Lys Pro Leu Thr Thr Asn Phe Met Val Ser Ala Gly Gly Ser Val Leu
                260                 265                 270

Asp Tyr Asp Asp Trp Gly Gly Glu Val Asp Phe Val Ser Asn Asp His
                275                 280                 285

Tyr Phe Ile Pro Gly Glu Ala His Leu Asp Glu Leu Ala Phe Ser Ala
    290                 295                 300

Ser Leu Val Asp Gly Ile Ser Arg Lys Asp Pro Trp Phe Leu Met Glu
305                 310                 315                 320

His Ser Thr Ser Ala Val Asn Trp Arg Pro Ile Asn Tyr Arg Lys Glu
                325                 330                 335

Pro Gly Gln Leu Val Arg Asp Ser Leu Ala His Val Ala Met Gly Ala
                340                 345                 350

Asp Ala Val Cys Tyr Phe Gln Trp Arg Gln Ser Arg Ser Gly Ala Glu
                355                 360                 365

Lys Phe His Ser Ala Met Leu Pro His Ala Gly Glu Asp Ser Gln Thr
    370                 375                 380

Phe Arg Asp Val Cys Glu Leu Gly Arg Asp Leu Gly Thr Leu Ala Asp
385                 390                 395                 400

Glu Gly Leu Leu Gly Thr Lys Leu Ala Lys Ser Ser Val Ala Ile Val
                405                 410                 415

Phe Asp Tyr Glu Ser Glu Trp Ala Ser Glu His Thr Ala Thr Pro Thr
                420                 425                 430

Gln Asn Val His His Ile Asp Glu Pro Leu Ala Trp Phe Arg Ala Leu
    435                 440                 445

Ala Asp Val Gly Val Thr Ala Asp Val Val Pro Ile Arg Ser Asn Trp
    450                 455                 460
```

-continued

```
Asp Glu Tyr Asp Val Ala Ile Leu Pro Ser Val Tyr Ile Leu Ser Glu
465             470             475             480

Glu Asn Thr Arg Arg Val Arg Asp Tyr Val Ala Asn Gly Gly Lys Leu
            485             490             495

Ile Ala Thr Tyr Tyr Thr Gly Ile Ser Asp Glu Arg Asp His Val Trp
            500             505             510

Leu Gly Gly Tyr Pro Gly Ser Ile Arg Asp Val Val Gly Val Arg Ile
            515             520             525

Glu Glu Phe Ala Pro Met Gly Ser Asp Trp Pro Gly Val Pro Asp His
            530             535             540

Leu Asp Leu Asp Asn Gly Ala Val Ala His Asp Ile Val Asp Val Ile
545             550             555             560

Gly Ser Ile Gly Lys Asp Ala Lys Val Leu Ala Ser Phe Lys Asp Asp
            565             570             575

Pro Trp Thr Gly Met Asp Gly Arg Pro Ala Ile Val Ser Asn Pro Tyr
            580             585             590

Gly Glu Gly Arg Ser Val Tyr Val Gly Ala Arg Leu Gly Arg Asp Gly
            595             600             605

Ile Ala Arg Ser Leu Pro Met Ile Leu Glu Thr Leu Gly Val Glu Val
            610             615             620

Lys Asp Ser Ser Asp Pro Asp Leu Leu Arg Ile Glu Arg Val Asp Glu
625             630             635             640

Ser Thr Gly Ala Arg Phe Thr Phe Leu Phe Asn Arg Thr Lys Glu Pro
            645             650             655

Val Ser Met Leu Val Glu Gly Arg Pro Val Val Met Ser Leu Ala Asp
            660             665             670

Cys Ala Gly Ala Thr Val Thr Ile Asn Pro Asn Gly Val Leu Val Val
            675             680             685

Lys Gln
690
```

```
<210> SEQ ID NO 3
<211> LENGTH: 698
<212> TYPE: PRT
<213> ORGANISM: Bifidobacterium adolescentis

<400> SEQUENCE: 3
```

```
Met Arg Arg Asn Phe Glu Trp Pro Lys Leu Leu Thr Ala Asp Gly Arg
1               5               10              15

Gly Ile Ala Phe Gly Gly Asp Tyr Asn Pro Asp Gln Trp Ser Glu Asp
            20              25              30

Ile Trp Asp Asp Asp Ile Arg Leu Met Lys Gln Ala Gly Val Asn Thr
            35              40              45

Val Ala Leu Ala Ile Phe Ser Trp Asp Arg Ile Gln Pro Thr Glu Asp
            50              55              60

Arg Trp Asp Phe Gly Trp Leu Asp Arg Ile Ile Asp Lys Leu Gly Asn
65              70              75              80

Ala Gly Ile Ala Val Asp Leu Ala Ser Ala Thr Ala Thr Ala Pro Leu
            85              90              95

Trp Leu Tyr Glu Ser His Pro Glu Val Leu Pro Arg Asp Lys Tyr Gly
            100             105             110

His Pro Val Asn Ala Gly Ser Arg Gln Ser Trp Ser Pro Thr Ser Pro
            115             120             125

Val Phe Lys Glu Tyr Ala Leu Thr Leu Cys Arg Lys Leu Ala Glu Arg
            130             135             140
```

-continued

```
Tyr Gly Thr Asn Pro Tyr Val Thr Ala Trp His Met Gly Asn Glu Tyr
145                 150                 155                 160

Gly Trp Asn Asn Arg Glu Asp Tyr Ser Asp Asn Ala Leu Asp Ala Phe
                165                 170                 175

Arg Ala Trp Cys Arg Arg Lys Tyr Gly Thr Ile Gly Ala Leu Asn Gln
                180                 185                 190

Ala Trp Gly Thr Thr Phe Trp Gly Gln Glu Met Asn Gly Phe Asp Glu
                195                 200                 205

Val Leu Ile Pro Arg Phe Met Gly Ala Asp Ser Met Val Asn Pro Gly
        210                 215                 220

Gln Lys Leu Asp Phe Glu Arg Phe Gly Asn Asp Met Leu Leu Asp Phe
225                 230                 235                 240

Tyr Lys Ala Glu Arg Asp Ala Ile Ala Glu Ile Cys Pro Asp Lys Pro
                245                 250                 255

Phe Thr Thr Asn Phe Met Val Ser Thr Asp Gln Cys Cys Met Asp Tyr
                260                 265                 270

Ala Ala Trp Ala Glu Glu Val Asn Phe Val Ser Asn Asp His Tyr Phe
                275                 280                 285

His Glu Gly Lys Ser His Leu Asn Lys Leu Ala Cys Ser Asp Ala Leu
        290                 295                 300

Met Asp Ser Leu Ala Leu Gly Lys Pro Trp Tyr Val Met Glu His Ser
305                 310                 315                 320

Thr Ser Ala Val Gln Trp Lys Pro Leu Asn Thr Arg Lys Arg Lys Gly
                325                 330                 335

Glu Thr Val Arg Asp Ser Leu Ala His Val Ala Met Gly Ala Asp Ala
                340                 345                 350

Ile Asn Phe Phe Gln Trp Arg Ala Ser Ala Phe Gly Ala Glu Ser Phe
                355                 360                 365

His Ser Ala Met Val Pro His Ala Gly Glu Asp Thr Lys Leu Phe Arg
        370                 375                 380

Gln Val Cys Glu Leu Gly Ala Ser Leu His Thr Leu Ala Asp Ala Gly
385                 390                 395                 400

Val Gln Gly Thr Glu Leu Ala His Ser Asp Thr Ala Ile Leu Phe Ser
                405                 410                 415

Ala Glu Ser Glu Gln Ala Thr Arg Ser Gln Thr Leu Pro Ser Met Lys
                420                 425                 430

Leu Asn His Trp His Asp Val Arg Asp Trp Tyr Arg Ala Phe Leu Asp
        435                 440                 445

Ala Gly Ser Arg Ala Asp Ile Val Pro Leu Ala Tyr Asp Trp Ser Ser
        450                 455                 460

Tyr Lys Thr Val Val Leu Pro Thr Val Leu Ile Leu Ser Ala Ala Asp
465                 470                 475                 480

Thr Gln Arg Leu Ala Asp Phe Ala Ala Ala Gly Gly Arg Val Val Ile
                485                 490                 495

Gly Tyr Ala Thr Gly Leu Ile Asp Glu His Phe His Thr Trp Leu Gly
                500                 505                 510

Gly Tyr Pro Gly Ala Gly Asp Gly Leu Leu Arg Leu Met Leu Gly Val
        515                 520                 525

Arg Gly Glu Glu Phe Asn Ile Leu Gly Ala Glu Ala Glu Gly Glu Pro
        530                 535                 540

Ser Glu Ile Arg Leu Ala Ser Ala Asp Asp Ser Val Ala Met Asp Gly
545                 550                 555                 560
```

-continued

```
Ser Thr Thr Arg Leu Trp Gln Asn Asp Val Asn Val Thr Gly Glu His
            565             570             575

Ala Gln Val Leu Ala Thr Tyr Ala Gly Glu Glu Ala Asp Glu Trp Glu
            580             585             590

Leu Asp Gly Thr Ala Ala Val Thr Arg Asn Pro Tyr Gly Ser Gly Glu
            595             600             605

Ala Tyr Phe Val Gly Cys Asp Leu Asp Val Ala Asp Leu Thr Lys Leu
            610             615             620

Val Arg Ala Tyr Leu Ala Ala Pro Ser Gln Asp Asn Ala Asp Val Leu
625             630             635             640

His Thr Val Arg Glu Ser Ala Asp Ala Thr Phe Asp Phe Tyr Leu Pro
            645             650             655

Arg Gly Lys Glu Thr Val Glu Leu Gln Gly Ile Glu Gly Glu Pro Val
            660             665             670

Ile Leu Phe Gln Thr Glu Arg Gly Lys Lys Pro Gly Ser Tyr Thr Val
            675             680             685

His Arg Asn Gly Val Leu Val Val Arg Arg
    690             695
```

```
<210> SEQ ID NO 4
<211> LENGTH: 668
<212> TYPE: PRT
<213> ORGANISM: Lactobacillus amylovorus

<400> SEQUENCE: 4

Met Thr Lys Thr Leu Ser Arg Phe Leu Tyr Gly Gly Asp Tyr Asn Pro
1               5               10              15

Asp Gln Trp Thr Glu Glu Thr Trp Pro Glu Asp Ile Lys Val Phe Lys
            20              25              30

Lys Val Asp Leu Asn Ser Ala Thr Ile Asn Ile Phe Ser Trp Ala Val
            35              40              45

Leu Glu Pro Arg Glu Gly Val Tyr Asp Phe Ser Lys Leu Asp Lys Ile
            50              55              60

Val Gln Glu Leu Ser Asp Ala Asn Phe Asp Ile Val Met Gly Thr Ala
65              70              75              80

Thr Ala Ala Met Pro Ala Trp Met Phe Lys Lys Tyr Pro Asp Ile Ala
            85              90              95

Arg Val Asp Tyr Gln Gly Arg Arg His Val Phe Gly Gln Arg His Asn
            100             105             110

Phe Cys Pro Asn Ser Lys Asn Tyr Gln Arg Leu Asp Ser Glu Leu Val
            115             120             125

Glu Lys Leu Ala Gln His Tyr Ala Asp Asn Ser His Ile Val Val Trp
            130             135             140

His Val Asn Asn Glu Tyr Gly Gly Asn Cys Tyr Cys Gly Asn Cys Gln
145             150             155             160

Asn Ala Phe Arg Asp Trp Leu Arg Asn Lys Tyr Lys Thr Leu Gly Ala
            165             170             175

Leu Asn Lys Ala Trp Asn Met Asn Val Trp Ser His Thr Ile Tyr Asp
            180             185             190

Trp Asp Glu Ile Val Val Pro Asn Glu Leu Gly Asp Ala Trp Gly Pro
            195             200             205

Glu Ser Ser Glu Thr Ile Val Ala Gly Leu Ser Ile Asp Tyr Leu Arg
            210             215             220

Phe Gln Ser Glu Ser Leu Gln Asn Leu Phe Lys Met Glu Lys Ala Val
225             230             235             240
```

```
Ile Lys Lys Tyr Asp Pro Glu Thr Pro Val Thr Thr Asn Phe His Ser
            245                 250                 255

Leu Pro Asn Lys Met Ile Asp Tyr Gln Lys Trp Ala Lys Asp Gln Asp
            260                 265                 270

Ile Ile Ser Tyr Asp Ser Tyr Pro Thr Tyr Asp Ala Pro Ala Tyr Lys
            275                 280                 285

Pro Ala Phe Leu Tyr Asp Leu Met Arg Ser Leu Lys His Gln Pro Phe
        290                 295                 300

Met Leu Met Glu Ser Ala Pro Ser Gln Val Asn Trp Gln Ser Tyr Ser
305                 310                 315                 320

Pro Leu Lys Arg Pro Gly Gln Met Ala Ala Thr Glu Leu Gln Ala Val
            325                 330                 335

Ala His Gly Ala Asp Thr Val Gln Phe Phe Gln Leu Lys Gln Ala Val
            340                 345                 350

Gly Gly Ser Glu Lys Phe His Ser Ala Ile Ile Ala His Ser Gln Arg
            355                 360                 365

Thr Asp Thr Arg Ala Phe Cys Glu Leu Ala Asp Leu Gly Gln Lys Leu
        370                 375                 380

Lys Glu Ala Gly Pro Thr Ile Leu Gly Ser Lys Thr Lys Ala Lys Val
385                 390                 395                 400

Ala Ile Val Phe Asp Trp Ser Asn Phe Trp Ser Tyr Glu Tyr Val Asp
            405                 410                 415

Gly Ile Thr Gln Asp Leu Asn Tyr Val Asp Ser Ile Leu Asp Tyr Tyr
            420                 425                 430

Arg Gln Phe Tyr Glu Arg Asn Ile Pro Thr Asp Ile Ile Gly Val Asp
            435                 440                 445

Asp Asp Phe Ser Asn Tyr Asp Leu Val Val Ala Pro Val Leu Tyr Met
        450                 455                 460

Val Lys Ala Gly Leu Ala Glu Lys Ile Asn Ser Tyr Val Glu Lys Gly
465                 470                 475                 480

Gly His Leu Val Thr Thr Tyr Met Ser Gly Met Val Asp Ser Thr Asp
            485                 490                 495

Asn Val Tyr Leu Gly Gly Tyr Pro Gly Pro Leu Lys Asp Val Thr Gly
            500                 505                 510

Ile Trp Val Glu Glu Ser Asp Ala Met Val Pro Gly Gln Lys Val Arg
            515                 520                 525

Val Thr Met Asp Gly Lys Glu Tyr Glu Thr Asn Leu Met Cys Asp Leu
        530                 535                 540

Ile His Pro Asn Lys Ala Lys Val Leu Ala Ser Tyr Ala Asp Glu Phe
545                 550                 555                 560

Tyr Thr Gly Thr Ala Ala Ile Thr Glu Asn Asp Tyr Gly Lys Gly Lys
            565                 570                 575

Ala Trp Tyr Val Gly Thr Lys Leu Gly His Gln Gly Leu Thr Gln Leu
            580                 585                 590

Phe Asn His Ile Val Leu Glu Thr Gly Val Glu Ser Leu Val Cys Asp
            595                 600                 605

Ser His Lys Leu Glu Val Thr Lys Arg Val Thr Ala Asp Gly Lys Glu
        610                 615                 620

Leu Tyr Phe Val Leu Asn Met Ser Asn Glu Glu Arg Glu Leu Pro Asn
625                 630                 635                 640

Lys Phe Ala Asp Tyr Glu Asp Ile Leu Thr Gly Glu Lys Ala Lys Ser
            645                 650                 655
```

-continued

```
Ser Met Lys Gly Trp Asp Val Gln Val Leu Thr Lys
            660               665

<210> SEQ ID NO 5
<211> LENGTH: 626
<212> TYPE: PRT
<213> ORGANISM: Lactobacillus amylovorus

<400> SEQUENCE: 5

Met Lys Ala Asn Ile Lys Trp Leu Asp Asp Pro Glu Val Phe Arg Ile
1               5                   10                  15

Asn Gln Leu Pro Ala His Ser Asp His Pro Phe Tyr Lys Asp Tyr Arg
            20                  25                  30

Glu Trp Gln Asn His Ser Ser Ser Phe Lys Gln Ser Leu Asn Gly Ala
        35                  40                  45

Trp Gln Phe His Phe Ser Lys Asp Pro Gln Ser Arg Pro Ile Asp Phe
    50                  55                  60

Tyr Lys Arg Ser Phe Asp Ser Ser Ser Phe Asp Thr Ile Pro Val Pro
65                  70                  75                  80

Ser Glu Ile Glu Leu Asn Gly Tyr Ala Gln Asn Gln Tyr Thr Asn Ile
                85                  90                  95

Leu Tyr Pro Trp Glu Ser Lys Ile Tyr Arg Lys Pro Ala Tyr Thr Leu
            100                 105                 110

Gly Arg Gly Ile Lys Asp Gly Asp Phe Ser Gln Gly Lys Asp Asn Thr
            115                 120                 125

Val Gly Ser Tyr Leu Lys His Phe Asp Leu Asn Pro Ala Leu Ala Gly
        130                 135                 140

His Asp Ile His Ile Gln Phe Glu Gly Val Glu Arg Ala Met Tyr Val
145                 150                 155                 160

Tyr Leu Asn Gly His Phe Ile Gly Tyr Ala Glu Asp Ser Phe Thr Pro
                165                 170                 175

Ser Glu Phe Asp Leu Thr Pro Tyr Ile Gln Ala Lys Asp Asn Ile Leu
            180                 185                 190

Ala Val Glu Val Phe Lys His Ser Thr Ala Ser Trp Leu Glu Asp Gln
            195                 200                 205

Asp Met Phe Arg Phe Ser Gly Ile Phe Arg Ser Val Glu Leu Leu Ala
        210                 215                 220

Leu Pro Arg Thr His Leu Met Asp Leu Asp Ile Lys Pro Thr Val Val
225                 230                 235                 240

Asn Asp Tyr His Asp Gly Val Phe Asn Ala Lys Leu His Phe Met Gly
                245                 250                 255

Lys Thr Ser Gly Asn Val His Val Leu Ile Glu Asp Ile Asp Gly Lys
            260                 265                 270

Thr Leu Leu Asn Lys Lys Leu Pro Leu Lys Ser Thr Val Glu Ile Glu
            275                 280                 285

Asn Glu Thr Phe Ala Asn Val His Leu Trp Asp Asn His Asp Pro Tyr
        290                 295                 300

Leu Tyr Gln Leu Ile Ile Glu Val His Asp Gln Asp Gly Lys Leu Val
305                 310                 315                 320

Glu Leu Ile Pro Tyr Gln Phe Gly Phe Arg Lys Ile Glu Ile Thr Lys
                325                 330                 335

Asp His Val Val Leu Leu Asn Gly Lys Arg Leu Ile Ile Asn Gly Val
            340                 345                 350

Asn Arg His Glu Trp Asp Ala Lys Arg Gly Arg Ser Ile Thr Leu Ala
            355                 360                 365
```

```
Asp Met Lys Gln Asp Ile Ala Thr Phe Lys His Asn Asn Ile Asn Ala
    370             375             380
Val Arg Thr Cys His Tyr Pro Asn Gln Ile Pro Trp Tyr Tyr Leu Cys
385             390             395             400
Asp Gln Asn Gly Ile Tyr Met Met Ala Glu Asn Asn Leu Glu Ser His
            405             410             415
Gly Thr Trp Gln Lys Leu Gly Gln Val Glu Ala Thr Ser Asn Val Pro
            420             425             430
Gly Ser Ile Pro Glu Trp Arg Glu Val Val Val Asp Arg Ala Arg Ser
            435             440             445
Asn Tyr Glu Thr Phe Lys Asn His Thr Ala Ile Leu Phe Trp Ser Leu
    450             455             460
Gly Asn Glu Ser Tyr Ala Gly Ser Asn Ile Ala Ala Met Asn Lys Leu
465             470             475             480
Tyr Lys Asp His Asp Ser Ser Arg Leu Thr His Tyr Glu Gly Val Phe
            485             490             495
His Ala Pro Glu Phe Lys Lys Glu Ile Ser Asp Leu Glu Ser Cys Met
            500             505             510
Tyr Leu Pro Pro Lys Glu Ala Glu Glu Tyr Leu Gln Asn Pro Lys Lys
            515             520             525
Pro Leu Val Glu Cys Glu Tyr Met His Asp Met Gly Thr Pro Asp Gly
            530             535             540
Gly Met Gly Ser Tyr Ile Lys Leu Ile Asp Lys Tyr Pro Gln Tyr Met
545             550             555             560
Gly Gly Phe Ile Trp Asp Phe Ile Asp Gln Ala Leu Leu Val His Asp
            565             570             575
Pro Val Ser Gly Gln Asp Val Leu Arg Tyr Gly Gly Asp Phe Asp Asp
            580             585             590
Arg His Ser Asp Tyr Glu Phe Ser Gly Asp Gly Leu Met Phe Ala Asp
            595             600             605
Arg Thr Pro Lys Pro Ala Met Gln Glu Val Arg Tyr Tyr Tyr Gly Leu
    610             615             620
His Lys
625

<210> SEQ ID NO 6
<211> LENGTH: 316
<212> TYPE: PRT
<213> ORGANISM: Lactobacillus amylovorus

<400> SEQUENCE: 6

Met Ala Tyr Thr Asn Asn Leu His Val Val Tyr Gly Glu Ala Ser Leu
1               5               10              15
Gly Val Asn Gly Gln Asp Phe Ala Tyr Leu Phe Ser Tyr Glu Arg Gly
            20              25              30
Gly Leu Glu Ser Leu Lys Ile Lys Asp Lys Glu Trp Leu Tyr Arg Thr
            35              40              45
Pro Thr Pro Thr Phe Trp Arg Ala Thr Thr Asp Asn Asp Arg Gly Ser
    50              55              60
Gly Phe Asn Gln Lys Ala Ala Gln Trp Leu Gly Ala Asp Met Phe Thr
65              70              75              80
Lys Cys Val Gly Ile His Val Gln Val Asp Asp His Arg Phe Asp Glu
            85              90              95
Leu Pro Val Ala Pro Ile Asn Asn Gln Phe Ser Asn Gln Glu Phe Ala
```

-continued

```
                100               105               110

His Glu Val Lys Val Ala Phe Asp Tyr Glu Thr Leu Thr Thr Pro Ala
        115               120               125

Thr Lys Val Lys Ile Ile Tyr Asn Ile Asn Asp Phe Gly His Met Thr
    130               135               140

Ile Thr Met His Tyr Phe Gly Lys Lys Gly Leu Pro Pro Leu Pro Val
145               150               155               160

Ile Gly Met Arg Phe Ile Met Pro Thr Lys Ala Lys Ser Phe Asp Tyr
            165               170               175

Thr Gly Leu Ser Gly Glu Thr Tyr Pro Asp Arg Met Ala Gly Ala Glu
            180               185               190

Arg Gly Thr Phe His Ile Asp Gly Leu Pro Val Thr Lys Tyr Leu Val
            195               200               205

Pro Gln Glu Asn Gly Met His Met Gln Thr Asn Glu Leu Val Ile Thr
        210               215               220

Arg Asn Ser Thr Gln Asn Asn Ala Asp Lys Asp Gly Asp Phe Ser Leu
225               230               235               240

Lys Ile Thr Gln Thr Lys Gln Pro Phe Asn Phe Ser Leu Leu Pro Tyr
            245               250               255

Thr Ala Glu Glu Leu Glu Asn Ala Thr His Ile Glu Glu Leu Pro Leu
            260               265               270

Ala Arg Arg Ser Val Leu Val Ile Ala Gly Ala Val Arg Gly Val Gly
            275               280               285

Gly Ile Asp Ser Trp Gly Ser Asp Val Glu Glu Gln Tyr His Ile Asp
        290               295               300

Pro Glu Gln Asp His Glu Phe Ser Phe Thr Leu Asn
305               310               315

<210> SEQ ID NO 7
<211> LENGTH: 693
<212> TYPE: PRT
<213> ORGANISM: Bifidobacteriumbifidum

<400> SEQUENCE: 7

Met Glu Arg Asn Met Ser Lys Arg Arg Lys His Ser Trp Pro Gln Pro
1               5                 10                15

Leu Lys Gly Ala Glu Ser Arg Leu Trp Tyr Gly Gly Asp Tyr Asn Pro
            20                25                30

Asp Gln Trp Pro Glu Glu Val Trp Asp Asp Asp Ile Arg Leu Met Lys
        35                40                45

Lys Ala Gly Val Asn Leu Val Ser Val Gly Ile Phe Ser Trp Ala Lys
    50                55                60

Ile Glu Pro Glu Glu Gly Lys Tyr Asp Phe Asp Trp Leu Asp Arg Ala
65                70                75                80

Ile Asp Lys Leu Gly Lys Ala Gly Ile Ala Val Asp Leu Ala Ser Ala
            85                90                95

Thr Ala Ser Pro Pro Met Trp Leu Thr Gln Ala His Pro Glu Val Leu
            100               105               110

Trp Lys Asp Glu Arg Gly Asp Thr Val Trp Pro Gly Ala Arg Glu His
        115               120               125

Trp Arg Pro Thr Ser Pro Val Phe Arg Glu Tyr Ala Leu Asn Leu Cys
    130               135               140

Arg Arg Met Ala Glu His Tyr Lys Gly Asn Pro Tyr Val Val Ala Trp
145               150               155               160
```

-continued

```
His Val Ser Asn Glu Tyr Gly Cys His Asn Arg Phe Asp Tyr Ser Asp
            165             170             175

Asp Ala Met Arg Ala Phe Gln Lys Trp Cys Lys Lys Arg Tyr Lys Thr
        180             185             190

Ile Asp Ala Val Asn Glu Ala Trp Gly Thr Ala Phe Trp Ala Gln His
        195             200             205

Met Asn Asp Phe Ser Glu Ile Ile Pro Pro Arg Tyr Ile Gly Asp Gly
    210             215             220

Asn Phe Met Asn Pro Gly Lys Leu Leu Asp Tyr Lys Arg Phe Ser Ser
225             230             235             240

Asp Ala Leu Lys Glu Leu Tyr Ile Ala Glu Arg Asp Val Leu Glu Ser
            245             250             255

Ile Thr Pro Gly Leu Pro Leu Thr Thr Asn Phe Met Val Ser Ala Gly
            260             265             270

Gly Ser Met Leu Asp Tyr Asp Asp Trp Gly Ala Glu Val Asp Phe Val
        275             280             285

Ser Asn Asp His Tyr Phe Thr Pro Gly Glu Ala His Phe Asp Glu Val
    290             295             300

Ala Tyr Ala Ala Ser Leu Met Asp Gly Ile Ser Arg Lys Glu Pro Trp
305             310             315             320

Phe Gln Met Glu His Ser Thr Ser Ala Val Asn Trp Arg Pro Ile Asn
            325             330             335

Tyr Arg Ala Glu Pro Gly Ser Val Val Arg Asp Ser Leu Ala Gln Val
            340             345             350

Ala Met Gly Ala Asp Ala Ile Cys Tyr Phe Gln Trp Arg Gln Ser Lys
        355             360             365

Ala Gly Ala Glu Lys Trp His Ser Ser Met Val Pro His Ala Gly Glu
        370             375             380

Asp Ser Gln Ile Phe Arg Asp Val Cys Glu Leu Gly Ala Asp Leu Gly
385             390             395             400

Arg Leu Ser Asp Glu Gly Leu Met Gly Thr Lys Thr Val Lys Ser Lys
            405             410             415

Val Ala Val Val Phe Asp Tyr Glu Ser Gln Trp Ala Thr Glu Tyr Thr
        420             425             430

Ala Asn Pro Thr Gln Gln Val Asp His Trp Thr Glu Pro Leu Asp Trp
        435             440             445

Phe Arg Ala Leu Ala Asp Asn Gly Ile Thr Ala Asp Val Val Pro Val
    450             455             460

Arg Ser Asp Trp Asp Ser Tyr Glu Ile Ala Val Leu Pro Cys Val Tyr
465             470             475             480

Leu Leu Ser Glu Glu Thr Ser Arg Arg Val Arg Glu Phe Val Ala Asn
            485             490             495

Gly Gly Lys Leu Phe Val Thr Tyr Tyr Thr Gly Leu Ser Asp Glu Asn
            500             505             510

Asp His Ile Trp Leu Gly Gly Tyr Pro Gly Ser Ile Arg Asp Val Val
        515             520             525

Gly Val Arg Val Glu Glu Phe Ala Pro Met Gly Asn Asp Met Pro Gly
        530             535             540

Ala Leu Asp His Leu Asp Leu Asp Asn Gly Thr Val Ala His Asp Phe
545             550             555             560

Ala Asp Val Ile Thr Ser Thr Ala Asp Thr Ser Thr Val Leu Ala Ser
            565             570             575

Tyr Lys Ala Glu Arg Trp Thr Gly Met Asn Glu Val Pro Ala Ile Val
```

-continued

```
                 580              585              590

Ala Asn Gly Tyr Gly Asp Gly Arg Thr Val Tyr Val Gly Cys Arg Leu
         595              600              605

Gly Arg Gln Gly Leu Ala Lys Ser Leu Pro Ala Met Leu Gly Ser Met
     610              615              620

Gly Leu Ser Asp Leu Ala Gly Asp Gly Arg Val Leu Arg Val Glu Arg
625              630              635              640

Ala Asp Ala Ala Ala Ala Ser His Phe Glu Phe Val Phe Asn Arg Thr
             645              650              655

His Glu Pro Val Thr Val Asp Val Glu Gly Glu Ala Ile Ala Ala Ser
             660              665              670

Leu Ala His Val Asp Asp Gly Arg Ala Thr Ile Asp Pro Thr Gly Val
         675              680              685

Val Val Leu Arg Arg
         690

<210> SEQ ID NO 8
<211> LENGTH: 680
<212> TYPE: PRT
<213> ORGANISM: Lactobacillus brevis

<400> SEQUENCE: 8

Met Lys Arg Glu Leu Lys Ser Lys Val Phe Leu His Gly Gly Asp Tyr
1               5               10              15

Asn Pro Glu Gln Trp Leu Gly Glu Pro Glu Ile Ile Asn Glu Asp Phe
             20              25              30

Ala Leu Phe Lys Asn Ala Ala Ile Asn Thr Val Thr Val Gly Ile Phe
         35              40              45

Ser Trp Ala Lys Leu Glu Pro Glu Glu Gly Lys Tyr Asp Phe Ala Trp
     50              55              60

Leu Asp Asp Ile Phe Asp Arg Val Glu Lys Met Asn Gly Tyr Val Ile
65              70              75              80

Leu Ala Thr Pro Ser Gly Ala Arg Pro Ala Trp Leu Ala Arg Lys Tyr
             85              90              95

Pro Glu Val Leu Arg Thr Asp Phe Asn Asn Gln Lys Arg Gly Phe Gly
         100             105             110

Gly Arg His Asn His Cys Leu Thr Ser Pro Ile Tyr Arg Lys Lys Val
     115             120             125

Arg Glu Ile Asn Thr Lys Leu Ala Glu His Phe Gly Lys Arg Pro Ser
     130             135             140

Leu Ile Leu Trp His Ile Ser Asn Glu Tyr Ser Gly Glu Cys Tyr Cys
145             150             155             160

Asp Leu Cys Gln Gln Ala Phe Arg Asp Trp Leu Lys Lys Lys Tyr Arg
             165             170             175

Thr Leu Glu Arg Leu Asn His Ser Trp Trp Asn Thr Phe Trp Ser His
             180             185             190

Thr Phe Ser Asp Trp Asn Gln Ile His Ala Pro Ser Pro Leu Ser Glu
             195             200             205

Met Gly Asn Lys Gly Met Asn Leu Asp Trp Lys Arg Phe Val Ser Asp
     210             215             220

Gln Ala Ile Ser Phe Ile Asp Asn Glu Val Glu Pro Leu Arg Lys Ile
225             230             235             240

Thr Ser Glu Ile Pro Val Thr Thr Asn Met Met Ala Gly Asn Pro Leu
             245             250             255
```

```
Met Asp Pro Phe Thr Gly Tyr Asn Tyr Gln Glu Met Ala Lys His Leu
            260             265             270

Asp Val Ile Ser Trp Asp Ser Tyr Pro Leu Trp Gly Asn Asp Phe Gln
            275             280             285

Ser Thr Glu Lys Leu Gly Gln Asn Val Gly Leu Ile His Asp Phe Phe
            290             295             300

Arg Ser Leu Lys His Gln Asn Phe Met Ile Met Glu Asn Thr Pro Ser
305             310             315             320

Arg Val Asn Trp Ala Asp Ile Asp Arg Ala Lys Arg Pro Gly Met His
            325             330             335

Gln Leu Ala Ser Leu Gln Asp Ile Ala His Ser Ser Asp Ser Val Leu
            340             345             350

Tyr Phe Gln Leu Arg Ala Ser Arg Gly Ser Ala Glu Met Phe His Gly
            355             360             365

Ala Val Ile Glu His Arg His Pro Glu Lys Thr Arg Val Phe His Asp
            370             375             380

Val Lys Asp Val Gly His Asp Leu Glu Lys Leu Glu Ser Ile Tyr Ser
385             390             395             400

Thr Ser Tyr Thr Lys Ala Lys Val Gly Ile Val Tyr Asp Tyr Asn Asn
            405             410             415

Ile Trp Ala Leu Glu Asp Ala Glu Gly Tyr Ser Lys Asp Lys Lys Ile
            420             425             430

Trp Gln Thr Ile Gln Ser Gln Tyr Gln Tyr Phe Tyr Gln Asn Asp Ile
            435             440             445

Pro Val Asp Phe Val Ser Pro Asn Asp Asn Phe Thr Gln Tyr Lys Leu
            450             455             460

Leu Ile Asp Pro Met His Phe Leu Met Thr Lys Glu Tyr Met Asp Lys
465             470             475             480

Leu Glu Ser Phe Val Lys Lys Cys Gly Tyr Val Val Gly Thr Tyr Ile
            485             490             495

Ser Gly Val Val Asp Glu Asn Gly Leu Ala Tyr Met Asn Glu Trp Pro
            500             505             510

Lys Gln Leu Gln Ser Ile Tyr Gly Ile Glu Pro Leu Glu Thr Asp Ser
            515             520             525

Leu Tyr Pro Lys Gln Ser Asn Ser Ile Glu Phe Ala Gly His Arg Tyr
            530             535             540

Gln Ala Tyr Asp Phe Cys Glu Thr Ile Phe Lys His Asp Ala Lys Val
545             550             555             560

Leu Ala Lys Tyr Thr Thr Asp Phe Tyr Ser Gly Thr Pro Ala Leu Thr
            565             570             575

Ala His Lys Cys Gly Glu Gly Lys Gly Tyr Tyr Ile Ala Cys Arg Thr
            580             585             590

Asp Thr Asp Phe Leu Ser Ala Ile Tyr Gly Gln Ile Val Lys Glu Leu
            595             600             605

Asp Leu Leu Pro Asn Leu Pro Ile Lys Lys Glu Thr Thr Lys Ile Ser
            610             615             620

Leu Gln Val Arg Glu Asn Asp Asp Glu Lys Tyr Leu Phe Val Gln Asn
625             630             635             640

Phe Ser His Glu Gln Gln Ser Ile Leu Leu Lys Gln Lys Met Lys Glu
            645             650             655

Met Leu Ser Asp Glu Phe Glu Glu Asn Lys Val Ile Val Lys Pro Tyr
            660             665             670

Gly Thr Lys Ile Tyr Gln Met Asn
```

-continued

```
                675                          680

<210> SEQ ID NO 9
<211> LENGTH: 689
<212> TYPE: PRT
<213> ORGANISM: Bifidobacterium catenulatum

<400> SEQUENCE: 9

Met Thr Gln Arg Arg Ser Tyr Arg Trp Pro Gln Pro Leu Ala Gly Gln
1               5                   10                  15

Gln Ala Arg Ile Trp Tyr Gly Gly Asp Tyr Asn Pro Asp Gln Trp Pro
                20                  25                  30

Glu Glu Val Trp Asp Asp Asp Val Arg Leu Met Lys Lys Ala Gly Val
            35                  40                  45

Asn Leu Val Ser Val Gly Ile Phe Ser Trp Ala Lys Ile Glu Thr Ser
    50                  55                  60

Glu Gly Val Tyr Asp Phe Asp Trp Leu Asp Arg Ile Ile Asp Lys Leu
65                  70                  75                  80

Gly Glu Ala Gly Ile Ala Val Asp Leu Ala Ser Ala Thr Ala Ser Pro
                85                  90                  95

Pro Met Trp Leu Thr Gln Ala His Pro Glu Val Leu Trp Lys Asp Tyr
                100                 105                 110

Arg Gly Asp Val Cys Gln Pro Gly Ala Arg Gln His Trp Arg Pro Thr
                115                 120                 125

Ser Pro Val Phe Arg Glu Tyr Ala Leu Lys Leu Cys Arg Ala Met Ala
    130                 135                 140

Glu His Tyr Lys Gly Asn Pro Tyr Val Val Ala Trp His Val Ser Asn
145                 150                 155                 160

Glu Tyr Gly Cys His Asn Arg Phe Asp Tyr Ser Glu Asp Ala Glu Arg
                165                 170                 175

Ala Phe Arg Lys Trp Cys Glu Glu Arg Tyr Gly Thr Ile Asp Ala Val
                180                 185                 190

Asn Asp Ala Trp Gly Thr Ala Phe Trp Ala Gln Arg Met Asn Asp Phe
                195                 200                 205

Thr Glu Ile Val Pro Pro Arg Phe Ile Gly Asp Gly Asn Phe Met Asn
    210                 215                 220

Pro Gly Lys Leu Leu Asp Phe Lys Arg Phe Ser Ser Asp Ala Leu Lys
225                 230                 235                 240

Ala Phe Tyr Val Ala Glu Arg Asp Ala Leu Ala Glu Ile Thr Pro Asp
                245                 250                 255

Leu Pro Leu Thr Thr Asn Phe Met Val Ser Ala Ala Gly Ser Val Leu
                260                 265                 270

Asp Tyr Asp Asp Trp Gly Arg Glu Val Asp Phe Val Ser Asn Asp His
            275                 280                 285

Tyr Phe Ile Pro Gly Glu Ala His Leu Asp Glu Leu Ala Phe Ser Ala
    290                 295                 300

Ser Leu Val Asp Gly Ile Ala Arg Lys Asp Pro Trp Phe Leu Met Glu
305                 310                 315                 320

His Ser Thr Ser Ala Val Asn Trp Arg Pro Val Asn Tyr Arg Lys Glu
                325                 330                 335

Pro Gly Gln Leu Val Arg Asp Ser Leu Ala His Val Ala Met Gly Ala
                340                 345                 350

Asp Ala Val Cys Tyr Phe Gln Trp Arg Gln Ser Lys Ala Gly Ala Glu
            355                 360                 365
```

-continued

```
Lys Phe His Ser Ala Met Val Pro His Thr Gly Glu Asp Ser Ala Val
    370             375             380

Phe Arg Asp Val Cys Glu Leu Gly Ala Asp Leu Asn Thr Leu Ala Asp
385             390             395             400

Asn Gly Leu Leu Gly Thr Lys Leu Ala Lys Ser Lys Val Ala Val Val
            405             410             415

Phe Asp Tyr Glu Ser Glu Trp Ala Thr Glu His Thr Ala Thr Pro Thr
            420             425             430

Gln Lys Val His His Val Asp Glu Pro Leu Gln Trp Phe Arg Ala Leu
        435             440             445

Ala Asp His Gly Val Thr Ala Asp Val Val Pro Val Ser Ser Asn Trp
    450             455             460

Asp Glu Tyr Glu Val Val Val Leu Pro Ser Val Tyr Ile Leu Ser Glu
465             470             475             480

Glu Thr Thr Arg Arg Val Arg Asp Tyr Val Val Asn Gly Gly Arg Leu
            485             490             495

Ile Val Thr Tyr Tyr Thr Gly Leu Ser Asp Glu Lys Asp His Val Trp
            500             505             510

Leu Gly Gly Tyr Pro Gly Ser Ile Arg Asp Val Val Gly Val Arg Val
        515             520             525

Glu Glu Phe Met Pro Met Gly Asp Asp Phe Pro Gly Val Pro Asp Cys
    530             535             540

Leu Gly Leu Ser Asn Gly Ala Val Ala His Asp Ile Ala Asp Val Ile
545             550             555             560

Gly Ser Val Asp Gly Thr Ala Thr Val Leu Glu Thr Phe Arg Asp Asp
            565             570             575

Pro Trp Thr Gly Met Asp Gly Ala Pro Ala Ile Val Ala Asn Thr Phe
            580             585             590

Gly Glu Gly Arg Ser Val Tyr Val Gly Ala Arg Leu Gly Arg Asp Gly
            595             600             605

Ile Ala Lys Ser Leu Pro Glu Ile Phe Glu Ser Leu Gly Met Ala Glu
    610             615             620

Thr Gly Glu Asn Asp Ser Arg Val Leu Arg Val Glu Arg Glu Gly Ser
625             630             635             640

Asp Gly Ser Arg Phe Val Phe Ser Phe Asn Arg Thr His Glu Ala Val
            645             650             655

Gln Ile Pro Phe Glu Gly Lys Ile Val Val Ser Ser Phe Ala Glu Val
            660             665             670

Ser Gly Glu Asn Val Ser Ile Lys Pro Asn Gly Val Ile Val Thr Lys
        675             680             685

Gln

<210> SEQ ID NO 10
<211> LENGTH: 689
<212> TYPE: PRT
<213> ORGANISM: Bifidobacterium pseudocatenulatum

<400> SEQUENCE: 10

Met Thr Gln Arg Arg Ala Tyr Arg Trp Pro Gln Pro Leu Ala Gly Gln
1               5               10              15

Gln Ala Arg Ile Trp Tyr Gly Gly Asp Tyr Asn Pro Asp Gln Trp Pro
            20              25              30

Glu Glu Val Trp Asp Asp Asp Val Arg Leu Met Lys Lys Ala Gly Val
            35              40              45
```

-continued

```
Asn Leu Val Ser Val Gly Ile Phe Ser Trp Ala Lys Ile Glu Thr Ser
    50                  55                  60

Glu Gly Val Tyr Asp Phe Asp Trp Leu Asp Arg Ile Ile Asn Lys Leu
65                  70                  75                  80

Gly Glu Ala Gly Ile Ala Val Asp Leu Ala Ser Ala Thr Ala Ser Pro
                85                  90                  95

Pro Met Trp Leu Thr Gln Ala His Pro Glu Val Leu Trp Lys Asp Tyr
            100                 105                 110

Arg Gly Asp Val Cys Gln Pro Gly Ala Arg Gln His Trp Arg Pro Thr
            115                 120                 125

Ser Pro Val Phe Arg Glu Tyr Ala Leu Lys Leu Cys Arg Ala Met Ala
    130                 135                 140

Glu His Tyr Lys Gly Asn Pro Tyr Val Val Ala Trp His Val Ser Asn
145                 150                 155                 160

Glu Tyr Gly Cys His Asn Arg Phe Asp Tyr Ser Glu Asp Ala Glu Arg
                165                 170                 175

Ala Phe Arg Lys Trp Cys Glu Glu Arg Tyr Gly Thr Ile Asp Ala Val
            180                 185                 190

Asn Asp Ala Trp Gly Thr Ala Phe Trp Ala Gln Arg Met Asn Asp Phe
            195                 200                 205

Thr Glu Ile Val Pro Pro Arg Phe Ile Gly Asp Gly Asn Phe Met Asn
    210                 215                 220

Pro Gly Lys Leu Leu Asp Phe Lys Arg Phe Ser Ser Asp Ala Leu Lys
225                 230                 235                 240

Ala Phe Tyr Val Ala Glu Arg Asp Ala Leu Ala Glu Ile Thr Pro Asp
                245                 250                 255

Leu Pro Leu Thr Thr Asn Phe Met Val Ser Ala Ala Gly Ser Val Leu
            260                 265                 270

Asp Tyr Asp Asp Trp Gly Arg Glu Val Asp Phe Val Ser Asn Asp His
            275                 280                 285

Tyr Phe Ile Pro Gly Glu Ala His Leu Asp Glu Leu Ala Phe Ser Ala
    290                 295                 300

Ser Leu Val Asp Gly Ile Ala Arg Lys Asp Pro Trp Phe Leu Met Glu
305                 310                 315                 320

His Ser Thr Ser Ala Val Asn Trp Arg Pro Val Asn Tyr Arg Lys Glu
                325                 330                 335

Pro Gly Gln Leu Val Arg Asp Ser Leu Ala His Val Ala Met Gly Ala
            340                 345                 350

Asp Ala Val Cys Tyr Phe Gln Trp Arg Gln Ser Lys Ala Gly Ala Glu
            355                 360                 365

Lys Phe His Ser Ala Met Val Pro His Ala Gly Glu Asp Ser Ala Val
    370                 375                 380

Phe Arg Asp Val Cys Glu Leu Gly Ala Asp Leu Asn Thr Leu Ala Asp
385                 390                 395                 400

Asn Gly Leu Leu Gly Thr Lys Leu Ala Lys Ser Lys Val Ala Val Val
                405                 410                 415

Phe Asp Tyr Glu Ser Glu Trp Ala Ser Glu His Thr Ala Thr Pro Thr
            420                 425                 430

Gln Lys Val His His Val Asp Glu Pro Leu Gln Trp Phe Arg Ala Leu
            435                 440                 445

Ala Asp His Gly Val Thr Ala Asp Val Val Pro Val Arg Gly Ala Trp
    450                 455                 460

Asp Asp Tyr Glu Met Val Val Leu Pro Ser Val Tyr Leu Leu Ser Glu
```

-continued

```
465                 470                 475                 480
Glu Thr Thr Arg Arg Val Arg Asp Tyr Val Val Gly Gly Arg Leu
                485                 490                 495
Val Val Thr Tyr Tyr Thr Gly Ile Ser Asp Glu Lys Asp His Val Trp
            500                 505                 510
Leu Gly Gly Tyr Pro Gly Ser Ile Arg Asp Val Val Gly Val Arg Val
            515                 520                 525
Glu Glu Phe Met Pro Met Gly Asp Asp Phe Pro Gly Val Pro Asp Cys
        530                 535                 540
Leu Gly Leu Ser Asn Gly Ala Val Ala His Asp Ile Ala Asp Val Ile
545                 550                 555                 560
Gly Ser Val Asp Gly Thr Ala Thr Val Leu Glu Thr Phe Lys Asp Asp
                565                 570                 575
Pro Trp Thr Gly Met Asp Gly Ala Pro Ala Ile Val Ala His Thr Phe
            580                 585                 590
Gly Glu Gly Arg Ser Val Tyr Val Gly Ala Arg Leu Gly Arg Asp Gly
            595                 600                 605
Ile Ala Leu Ser Leu Pro Glu Ile Leu Asp Ser Leu Gly Met Ala Glu
        610                 615                 620
Ala Gly Gly Asn Asp Gly Arg Val Leu Arg Val Glu Arg Glu Gly Ala
625                 630                 635                 640
Asp Gly Ser Arg Phe Val Phe Ser Phe Asn Arg Thr His Glu Thr Val
                645                 650                 655
Arg Val Pro Val Glu Gly Glu Val Val Val Ser Ser Phe Ala Glu Val
            660                 665                 670
Ser Gly Glu Thr Ile Ser Ile Lys Pro Asn Gly Val Ile Val Thr Lys
            675                 680                 685
Gln

<210> SEQ ID NO 11
<211> LENGTH: 680
<212> TYPE: PRT
<213> ORGANISM: Lactobacillus gasseri

<400> SEQUENCE: 11

Met Lys Arg Ile Leu Asn Thr Asn Glu Phe Leu His Gly Gly Asp Tyr
1               5                   10                  15
Asn Pro Glu Gln Trp Trp Asp Glu Pro Asp Val Ile Asn Gln Asp Phe
                20                  25                  30
Ala Leu Phe Lys Gln Ala Lys Ile Asn Thr Val Thr Val Gly Ile Phe
            35                  40                  45
Ser Trp Ala Lys Leu Glu Pro Glu Glu Gly Asn Tyr Asp Phe Ser Trp
        50                  55                  60
Leu Asp Ser Ile Phe Asp Arg Val Glu Glu Met Asn Gly His Val Val
65                  70                  75                  80
Leu Ala Thr Pro Ser Gly Ala Arg Pro Ala Trp Leu Ala Gln Lys Tyr
                85                  90                  95
Pro Glu Val Leu Arg Thr Asp Asn Leu Gly Asn Lys Arg Gly Phe Gly
            100                 105                 110
Gly Arg His Asn His Cys Leu Thr Ser Pro Ile Tyr Arg Glu Lys Val
            115                 120                 125
Arg Glu Ile Asn Thr Lys Leu Ala Glu His Phe Gly Gln Arg Lys Ser
        130                 135                 140
Leu Val Leu Trp His Ile Ser Asn Glu Tyr Ser Gly Glu Cys Tyr Cys
```

-continued

```
145                150                155                160
Glu Ser Cys Lys Asn Ala Phe Arg Asp Trp Leu Lys Asn Lys Tyr Gly
                165                170                175

Asn Leu Asp Asn Leu Asn His Ala Trp Trp Asn Thr Phe Trp Ser His
                180                185                190

Thr Tyr Asn Asp Trp Ser Gln Val Asn Pro Pro Ser Pro Leu Gly Glu
                195                200                205

Met Gly Asn Lys Gly Met Asn Leu Asp Trp Lys Arg Phe Ile Thr Asp
    210                215                220

Gln Thr Ile Ser Phe Ile Asp Asn Glu Ala Ala Pro Leu Arg Lys Ile
225                230                235                240

Thr Pro Asn Val Pro Val Thr Thr Asn Met Met Ala Gly Asn Pro Leu
                245                250                255

Met Asp Pro Phe Ala Gly Phe Asp Tyr Gln Lys Val Ala Lys His Leu
                260                265                270

Asp Phe Ile Ser Trp Asp Ser Tyr Pro Ala Trp Gly Asn Asp Asn Gln
                275                280                285

Thr Thr Ala Glu Leu Gly Arg Asn Val Gly Leu Val His Asp Phe Phe
    290                295                300

Arg Ser Leu Lys His Gln Asn Phe Leu Val Met Glu Asn Thr Pro Ser
305                310                315                320

Arg Val Asn Trp His Ser Val Asp Arg Ala Lys Arg Pro Gly Met His
                325                330                335

Glu Leu Ala Ser Leu Gln Asp Val Ala Arg Gly Ser Gln Gly Val Leu
                340                345                350

Tyr Phe Gln Leu Arg Ala Ser Arg Gly Ser Ser Glu Met Phe His Gly
                355                360                365

Ala Val Ile Glu His Leu His Pro Glu Gln Thr Arg Ala Phe Lys Asp
    370                375                380

Val Thr Thr Val Gly Lys Asp Leu Glu Asn Ile Arg Pro Ile Ile Asn
385                390                395                400

Thr Asn Tyr Ala Lys Ala Arg Val Ala Ile Val Phe Ser Tyr Asp Ser
                405                410                415

Tyr Trp Ala Leu Gln Asp Ala Glu Ser Tyr Ser Lys Asp Lys Lys Ile
                420                425                430

Trp Gln Thr Ile Gln Lys His Tyr Arg Tyr Phe Tyr Lys His Asp Ile
                435                440                445

Pro Val Asp Phe Val Ser Val Glu Asp Asp Phe Ser Asn Tyr Asp Leu
    450                455                460

Leu Ile Asp Pro Met His Phe Leu Met Ser Lys Ala Tyr Leu Lys Lys
465                470                475                480

Leu Ala Ser Tyr Val Lys Asn Gly Gly Arg Val Val Gly Thr Tyr Ile
                485                490                495

Ser Gly Val Val Asp Glu Asn Asp Leu Ala Tyr Met Asn Glu Trp Pro
                500                505                510

Lys Glu Leu Gln Asp Ile Tyr Gly Val Glu Pro Leu Glu Thr Asp Val
                515                520                525

Leu Tyr Pro Gly Gln Ser Asn Thr Leu Asn Phe Asp Gly His Glu Tyr
                530                535                540

Lys Ala His Asp Tyr Cys Glu Thr Leu Ile Asn Cys Arg Gly Lys Val
545                550                555                560

Leu Ala Lys Tyr Ala Ser Asp Phe Tyr Gln Asp Thr Pro Ala Val Val
                565                570                575
```

```
Glu His Glu Tyr Gly Ala Gly Lys Gly Tyr Tyr Leu Ala Cys Arg Thr
            580             585             590

Asp Tyr Asp Leu Leu Glu Lys Phe Tyr Glu Lys Ile Thr Ala Asn Leu
        595             600             605

Ile Pro Glu Phe Pro Val Lys Lys Phe Ser Ser Asn Ile Ser Ile Gln
    610             615             620

Val Arg Glu Asn Lys Asp Gln Lys Tyr Tyr Phe Val Gln Asn Phe Ser
625             630             635             640

Asp Lys Ser Glu Gln Ile Lys Val Asp Gly Glu Leu Glu Asp Leu Leu
            645             650             655

Glu Lys Lys Ile Asp Arg Gly Glu Val Val Leu Asn Pro Phe Gly Ser
            660             665             670

Lys Ile Tyr Tyr Lys Lys Gly Asn
        675             680

<210> SEQ ID NO 12
<211> LENGTH: 621
<212> TYPE: PRT
<213> ORGANISM: Lactobacillushelveticus

<400> SEQUENCE: 12

Met Leu Glu Pro Glu Glu Gly Lys Tyr Asp Phe Ser Glu Leu Asp Lys
1               5               10              15

Val Val Lys Lys Leu Ser Asp Ala Asn Phe Asp Ile Val Ile Gly Thr
            20              25              30

Ser Thr Ala Ala Met Pro Ala Trp Met Phe Lys Lys Tyr Pro Asp Val
        35              40              45

Ala Arg Val Asp Tyr Gln Gly Arg Arg His Val Phe Gly Gln Arg Tyr
    50              55              60

Asn Phe Cys Pro Asn Ser Lys Asn Tyr Gln Arg Leu Ala Gly Asn Leu
65              70              75              80

Val Glu Glu Leu Ala Lys His Tyr Gln Asn Asn Pro Asn Ile Val Val
            85              90              95

Trp His Val Asn Asn Glu Tyr Gly Gly Asn Cys Tyr Cys Glu Asn Cys
        100             105             110

Gln His Glu Phe Arg Lys Trp Leu Lys Asp Lys Tyr Gln Thr Leu Asp
        115             120             125

Ala Leu Asn Lys Ala Trp Asn Met Asn Val Trp Ser His Thr Ile Tyr
    130             135             140

Asp Trp Asp Glu Ile Val Val Ser Asn Glu Leu Gly Asp Ala Trp Gly
145             150             155             160

Pro Glu Gly Ser Glu Thr Ile Val Ala Gly Leu Ser Ile Asp Tyr Leu
            165             170             175

Arg Phe Gln Ser Glu Ser Leu Gln Asn Leu Phe Lys Met Glu Lys Gln
            180             185             190

Ile Ile Lys Lys His Asp Ser Glu Ala Pro Val Thr Thr Asn Phe His
        195             200             205

Ser Leu Pro Asn Lys Met Ile Asp Tyr Gln Lys Trp Ala Lys Asp Gln
    210             215             220

Asp Ile Ile Ser Tyr Asp Ser Tyr His Thr Tyr Asp Ala Pro Thr Tyr
225             230             235             240

Lys Pro Ala Phe Leu Tyr Asn Leu Met Arg Ser Leu Lys His Gln Pro
            245             250             255

Phe Met Leu Met Glu Ser Ala Pro Ser Gln Val Asn Trp Gln Pro Tyr
```

-continued

```
            260              265              270
Ser Pro Leu Lys Arg Pro Gly Gln Met Ala Ala Thr Glu Leu Gln Ala
        275              280              285

Val Ala His Gly Ala Asp Thr Val Gln Phe Phe Gln Leu Lys Gln Ala
        290              295              300

Val Gly Gly Ser Glu Lys Phe His Ser Ala Val Ile Ala His Ser Gln
305              310              315              320

Arg Thr Asp Thr Arg Val Phe Lys Glu Leu Val Asp Leu Gly His Lys
                325              330              335

Leu Lys Arg Ala Gly Ser Thr Ile Leu Gly Ser Thr Ile Asn Ala Lys
            340              345              350

Val Gly Ile Val Phe Asp Trp Ser Asn Phe Trp Ser Tyr Glu Tyr Val
            355              360              365

Asp Gly Ile Ser Gln Asp Met Asp Tyr Val Asp Ser Ile Leu Asp Tyr
        370              375              380

Tyr Arg Gln Phe Tyr Glu Arg Asn Ile Pro Thr Asp Ile Ile Ser Val
385              390              395              400

Asp Asp Asp Phe Ser Lys Tyr Asp Leu Ile Val Ala Pro Val Leu Tyr
                405              410              415

Met Val Lys Asp Gly Leu Ala Glu Lys Ile Asn Asn Tyr Val Glu Cys
                420              425              430

Gly Gly Asn Phe Val Thr Thr Tyr Met Ser Gly Met Val Asp Ser Thr
            435              440              445

Asp Asn Val Tyr Leu Gly Gly Tyr Pro Gly Pro Leu Lys Asn Val Thr
        450              455              460

Gly Ile Trp Val Glu Glu Ser Asp Ala Val Val Pro Gly His Thr Thr
465              470              475              480

Thr Val Ser Leu Lys Gly Lys Asp Tyr Lys Ala Gly Phe Val Cys Asp
                485              490              495

Leu Ile His Pro Glu Gln Ala Lys Val Leu Ala Glu Tyr Ser Asn Glu
                500              505              510

Phe Tyr Ala Gly Thr Pro Ala Ile Thr Glu Asn Lys Tyr Gly Gln Gly
            515              520              525

Lys Ala Trp Tyr Val Gly Thr Arg Leu Asp His Thr Gly Leu Thr Gln
        530              535              540

Leu Phe Asn His Ile Val Leu Glu Ser Asn Ile Glu Ser Leu Val Cys
545              550              555              560

Asp Gly Asp Lys Leu Glu Val Thr Lys Arg Val Thr Gln Asp Gly Gln
                565              570              575

Glu Leu Tyr Phe Val Leu Asn Met Ser Asn Glu Val Arg Asn Leu Pro
                580              585              590

Gln Lys Phe Ile Gly Tyr Gln Asp Ile Leu Thr Asp Lys Lys Ala Ser
            595              600              605

Asp Lys Leu Glu Arg Trp Gly Val Gln Val Leu Thr Lys
        610              615              620
```

```
<210> SEQ ID NO 13
<211> LENGTH: 710
<212> TYPE: PRT
<213> ORGANISM: Bifidobacterium longum

<400> SEQUENCE: 13

Met Thr Thr His Arg Ala Phe Arg Trp Pro Ser Leu Leu Thr Glu Ser
1               5               10              15
```

-continued

```
Gly Arg Gly Ile Ala Phe Gly Gly Asp Tyr Asn Pro Asp Gln Trp Pro
            20                  25                  30

Glu Glu Thr Leu Asp Glu Asp Ile Arg Leu Met Gly Glu Ala Gly Val
            35                  40                  45

Asn Val Val Ser Leu Ala Ile Phe Ser Trp Asp Lys Ile Glu Pro Val
        50                  55                  60

Glu Gly Ala Phe Thr Phe Glu Trp Leu Asp His Val Ile Asp Arg Leu
65                  70                  75                  80

Gly Arg Ala Gly Ile Ala Val Asp Leu Ala Ser Ala Thr Ala Ala Ala
                85                  90                  95

Pro Leu Trp Leu Tyr Glu Ser His Pro Glu Val Leu Pro Val Asp Arg
            100                 105                 110

Tyr Gly His Thr Val Asn Ala Gly Ser Arg Gln Ser Trp Gln Pro Thr
            115                 120                 125

Ser Pro Val Phe Lys Glu Tyr Ala Leu Arg Leu Cys Arg Lys Leu Ala
        130                 135                 140

Glu His Tyr Lys Asp Asn Pro Tyr Val Thr Ala Trp His Met Gly Asn
145                 150                 155                 160

Glu Tyr Gly Trp Asn Asn Arg Tyr Asp Tyr Ser Asp Asn Ala Leu Ala
                165                 170                 175

Ala Phe Arg Thr Trp Cys Glu Ala Lys Tyr Gly Thr Ile Asp Ala Leu
            180                 185                 190

Asn Glu Ala Trp Gly Thr Ala Phe Trp Ser Gln His Val Asn Ser Phe
            195                 200                 205

Asp Glu Val Leu Leu Pro Arg His Met Gly Gly Asp Ala Met Val Asn
        210                 215                 220

Pro Ser Gln Gln Leu Asp Tyr Glu Arg Phe Gly Asn Asp Met Leu Leu
225                 230                 235                 240

Asp Phe Tyr Lys Ala Glu Arg Asp Ala Ile Glu Gln Ile Cys Pro Asp
                245                 250                 255

Lys Pro Phe Thr Thr Asn Phe Met Val Ser Thr Asp Gln Cys Val Met
            260                 265                 270

Asn Tyr Ala Lys Trp Ala Asp Glu Val Asp Phe Val Ser Asn Asp His
            275                 280                 285

Tyr Phe His Glu Gly Glu Ser His Leu Asp Glu Leu Ala Cys Ser Asp
        290                 295                 300

Ala Leu Met Asp Ser Leu Ala Leu Gly Lys Pro Trp Tyr Val Met Glu
305                 310                 315                 320

His Ser Thr Ser Ala Val Gln Trp Lys Pro Leu Asn Thr Arg Lys Arg
                325                 330                 335

Ala Gly Glu Leu Met Arg Asp Ser Leu Ala His Val Ala Met Gly Ala
            340                 345                 350

Asp Ala Ile Cys Phe Phe Gln Trp Arg Gln Ser Lys Ser Gly Ala Glu
            355                 360                 365

Ala Phe His Ser Ala Met Leu Pro His Ala Gly Ala Asp Ser Lys Val
        370                 375                 380

Phe Arg Gly Val Cys Glu Leu Gly Lys Ala Leu Lys Thr Leu Ser Asp
385                 390                 395                 400

Ala Gly Leu Gln Gly Thr Glu Leu Glu Arg Ala Gly Thr Ala Ile Leu
                405                 410                 415

Phe Ser Ala Glu Ser Glu Trp Ala Thr Arg Ser Glu Thr Leu Pro Ser
            420                 425                 430

Met Lys Leu Asn His Trp His Asp Val Arg Asp Trp Tyr Arg Gly Phe
```

-continued

```
              435                 440                 445

Leu Asp Ala Gly Leu Arg Ala Asp Val Val Pro Leu Ala Tyr Asp Trp
    450                 455                 460

Thr Gly Tyr Lys Thr Ile Val Leu Pro Thr Val Leu Ser Leu Ser Asp
465                 470                 475                 480

Glu Asp Val Leu Arg Ile Ala Asp Phe Ala Lys Ala Gly Gly Thr Val
                    485                 490                 495

Ile Val Gly Tyr Ala Ala Gly Leu Ile Asp Glu His Phe His Ile Gly
                500                 505                 510

Leu Gly Gly Tyr Pro Gly Ala Gly Asn Gly Leu Leu Arg Asp Met Leu
                515                 520                 525

Gly Ile Arg Ser Glu Glu Phe Asn Ile Leu Gly Glu Glu Ala Glu Gly
                530                 535                 540

Glu Pro Ser Glu Ile Ser Leu Ser Asn Gly Leu Thr Thr Arg Leu Trp
545                 550                 555                 560

Gln Asn Asp Val Thr Ser Val Ala Ala Asp Thr Thr Val Leu Ala Ser
                    565                 570                 575

Tyr Ala Gly Glu Ser Ala Ala Asp Trp Glu Leu Glu Arg Thr Pro Ala
                580                 585                 590

Ile Thr Ser Arg Pro Tyr Gly Asn Gly Thr Ala Ile Tyr Val Gly Cys
                595                 600                 605

Asp Leu Asn Arg His Asp Ile Ala Gln Leu Leu Lys Ala Leu Gly Ser
            610                 615                 620

Arg Trp Gln Glu Leu Ser Ala Gln Pro Thr Glu Ser Gly Gln Thr Pro
625                 630                 635                 640

Thr Tyr Pro Thr Thr Asp Pro Arg Ile Leu His Thr Ile Arg Arg Ser
                    645                 650                 655

Ala Asp Gly Ser Thr Arg Phe Asp Phe Tyr Leu Asn Arg Ser Asn Gln
                660                 665                 670

Pro Val Ala Ile Asn Gly Val Glu Gly Asp Pro Ile Ile Ala His Arg
                675                 680                 685

Cys Glu Thr Asp Ala Val Gly Tyr Thr Leu Asn Arg Asn Ala Ile Leu
    690                 695                 700

Ile Ala Lys Thr Ser Cys
705                 710

<210> SEQ ID NO 14
<211> LENGTH: 691
<212> TYPE: PRT
<213> ORGANISM: Bifidobacterium longum

<400> SEQUENCE: 14

Met Glu Arg Lys Glu Phe Lys Trp Pro Gln Pro Leu Ala Gly Asn Lys
1               5                   10                  15

Pro Arg Ile Trp Tyr Gly Gly Asp Tyr Asn Pro Asp Gln Trp Pro Glu
                20                  25                  30

Glu Val Trp Asp Glu Asp Val Ala Leu Met Gln Gln Ala Gly Val Asn
                35                  40                  45

Leu Val Ser Val Ala Ile Phe Ser Trp Ala Lys Leu Glu Pro Glu Glu
    50                  55                  60

Gly Val Tyr Asp Phe Asp Trp Leu Asp Arg Val Ile Asp Lys Leu Gly
65                  70                  75                  80

Lys Ala Gly Ile Ala Val Asp Leu Ala Ser Gly Thr Ala Ser Pro Pro
                85                  90                  95
```

-continued

```
Met Trp Met Thr Gln Ala His Pro Glu Ile Leu Trp Val Asp Tyr Arg
            100                 105                 110

Gly Asp Val Cys Gln Pro Gly Ala Arg Gln His Trp Arg Ala Thr Ser
            115                 120                 125

Pro Val Phe Leu Asp Tyr Ala Leu Ser Leu Cys Arg Lys Met Ala Glu
            130                 135                 140

His Tyr Lys Asp Asn Pro Tyr Val Val Ser Trp His Val Ser Asn Glu
145                 150                 155                 160

Tyr Gly Cys His Asn Arg Phe Asp Tyr Ser Glu Asp Ala Glu Arg Ala
                165                 170                 175

Phe Gln Lys Trp Cys Glu Lys Lys Tyr Gly Thr Ile Asp Ala Val Asn
                180                 185                 190

Asp Ala Trp Gly Thr Ala Phe Trp Ala Gln Arg Met Asn Asn Phe Ser
            195                 200                 205

Glu Ile Ile Pro Pro Arg Phe Ile Gly Asp Gly Asn Phe Met Asn Pro
    210                 215                 220

Gly Lys Leu Leu Asp Trp Lys Arg Phe Ser Ser Asp Ala Leu Leu Asp
225                 230                 235                 240

Phe Tyr Lys Ala Glu Arg Asp Ala Leu Leu Glu Ile Ala Pro Lys Pro
                245                 250                 255

Gln Thr Thr Asn Phe Met Val Ser Ala Gly Gly Thr Gly Ile Asp Tyr
            260                 265                 270

Asp Lys Trp Gly Tyr Asp Val Asp Phe Val Ser Asn Asp His Tyr Phe
            275                 280                 285

Thr Pro Gly Glu Ala His Phe Asp Glu Leu Ala Tyr Ser Ala Ser Leu
    290                 295                 300

Cys Asp Gly Ile Ala Arg Lys Asn Pro Trp Phe Leu Met Glu His Ser
305                 310                 315                 320

Ser Ser Ala Val Asn Trp Arg Pro Ile Asn Tyr Arg Val Glu Pro Gly
                325                 330                 335

Glu Leu Val Arg Asp Ser Leu Ala His Leu Ala Met Gly Ser Asp Ala
            340                 345                 350

Ile Cys Tyr Phe Gln Trp Arg Gln Ser Lys Ala Gly Ala Glu Lys Trp
            355                 360                 365

His Ser Ser Met Val Pro His Ala Gly Pro Asp Ser Gln Ile Phe Arg
    370                 375                 380

Asp Val Cys Glu Leu Gly Ala Asp Leu Asn Lys Leu Ala Asp Glu Gly
385                 390                 395                 400

Leu Leu Ser Thr Lys Leu Val Lys Ser Lys Val Ala Val Val Phe Asp
                405                 410                 415

Tyr Glu Ser Gln Trp Val Thr Glu His Thr Ala Thr Pro Thr Gln Glu
            420                 425                 430

Val Arg His Trp Thr Glu Pro Leu Ala Trp Phe Arg Ala Leu Ala Asp
            435                 440                 445

Asn Gly Leu Thr Ala Asp Val Val Pro Val Arg Gly Ser Trp Asp Glu
    450                 455                 460

Tyr Glu Ala Val Val Leu Pro Ser Leu Thr Ile Leu Ser Glu Glu Thr
465                 470                 475                 480

Thr Arg Arg Val Arg Glu Tyr Val Ala Asn Gly Gly Lys Leu Phe Val
                485                 490                 495

Thr Tyr Tyr Thr Gly Leu Val Asp Asp Lys Asp His Val Trp Leu Gly
            500                 505                 510

Gly Tyr Pro Gly Ser Ile Arg Asp Val Val Gly Val Arg Val Glu Glu
```

-continued

```
                515                 520                 525

Phe Ala Pro Met Gly Asn Asp Phe Pro Gly Ala Met Asp His Leu Asp
    530                 535                 540

Leu Asp Asn Gly Thr Val Ala His Asp Phe Ala Asp Val Ile Thr Ser
545                 550                 555                 560

Val Ala Asp Thr Ala His Val Val Ala Ser Phe Lys Ala Asp Lys Trp
                565                 570                 575

Thr Gly Phe Asp Gly Ala Pro Ala Ile Thr Val Asn Asp Phe Gly Asp
                580                 585                 590

Gly Lys Ala Ala Tyr Val Gly Ala Arg Leu Gly Arg Glu Gly Leu Ala
                595                 600                 605

Lys Ser Leu Pro Ala Leu Leu Glu Glu Leu Gly Ile Glu Thr Ser Ala
    610                 615                 620

Glu Asp Asp Arg Gly Glu Val Leu Arg Val Glu Arg Ala Asp Glu Thr
625                 630                 635                 640

Gly Glu Asn His Phe Val Phe Leu Phe Asn Arg Thr His Asp Val Ala
                645                 650                 655

Val Val Asp Val Glu Gly Glu Pro Leu Val Ala Ser Leu Ala Gln Val
                660                 665                 670

Asn Glu Ser Glu Arg Thr Ala Ala Ile Gln Pro Asn Gly Val Leu Val
    675                 680                 685

Val Lys Leu
    690

<210> SEQ ID NO 15
<211> LENGTH: 719
<212> TYPE: PRT
<213> ORGANISM: Bifidobacterium longum

<400> SEQUENCE: 15

Met Thr Thr Arg Arg Thr Phe Arg Trp Pro Ser Leu Leu Thr Glu Ser
1               5                   10                  15

Gly Arg Gly Ile Ala Phe Gly Gly Asp Tyr Asn Pro Asp Gln Trp Pro
                20                  25                  30

Glu Glu Thr Leu Asp Glu Asp Ile Arg Leu Met Val Gln Ala Gly Val
            35                  40                  45

Asn Thr Val Ala Leu Ala Ile Phe Ser Trp Asp Lys Ile Glu Pro Arg
    50                  55                  60

Glu Gly Glu Phe Thr Phe Glu Trp Leu Asp His Val Ile Asp Lys Leu
65                  70                  75                  80

Gly Ala Ala Ser Ile Ala Val Asp Leu Ala Ser Ala Thr Ala Thr Ala
                85                  90                  95

Pro Leu Trp Leu Tyr Glu Arg His Pro Glu Val Leu Pro Ile Asp Arg
                100                 105                 110

Tyr Gly His Val Val Asn Ala Gly Ser Arg Gln Ser Trp Gln Pro Thr
            115                 120                 125

Ser Pro Val Leu Lys Glu Tyr Ala Leu Arg Leu Cys Arg Lys Leu Ala
    130                 135                 140

Glu His Tyr Lys Asp Asn Pro Tyr Val Thr Ala Trp His Met Gly Asn
145                 150                 155                 160

Glu Tyr Gly Trp Asn Asn Arg Tyr Asp Tyr Ser Asp Asn Ala Leu Ala
                165                 170                 175

Ala Phe Arg Thr Trp Cys Glu Ala Lys Tyr Gly Thr Val Asp Ala Leu
            180                 185                 190
```

```
Asn Glu Ala Trp Gly Thr Ala Phe Trp Ser Gln His Val Asn Ser Phe
        195                 200             205

Asp Glu Val Leu Leu Pro Arg His Met Gly Gly Asp Ser Met Val Asn
    210             215             220

Pro Pro Gln Gln Leu Asp Tyr Glu Arg Phe Gly Asn Asp Met Leu Leu
225             230             235                 240

Asp Phe Tyr Lys Ala Glu Arg Asp Ala Ile Glu Glu Ile Cys Pro Gly
            245             250             255

Lys Pro Phe Thr Thr Asn Phe Met Val Ser Thr Asp Gln Cys Thr Met
            260             265             270

Asp Tyr Ala Gln Trp Ala Asn Glu Val Asp Phe Val Ser Asn Asp His
        275             280             285

Tyr Phe His Glu Gly Glu Ser His Leu Asp Glu Leu Ala Cys Ser Asp
    290             295             300

Ala Leu Met Asp Ser Leu Ala Leu Gly Lys Pro Trp Tyr Val Met Glu
305             310             315                 320

His Ser Thr Ser Ala Val Gln Trp Lys Pro Leu Asn Thr Arg Lys Arg
            325             330             335

Ala Gly Glu Leu Met Arg Asp Ser Leu Ala His Val Ala Met Gly Ala
        340             345             350

Asp Ala Ile Asn Phe Phe Gln Trp Arg Gln Ser Ala Ser Gly Ala Glu
        355             360             365

Ala Phe His Ser Ala Met Val Pro His Ala Gly Ser Asp Thr Lys Leu
    370             375             380

Phe Arg Gly Val Cys Glu Leu Gly Ala Ala Leu Lys Thr Leu Ser Asp
385             390             395                 400

Ala Gly Val Gln Asp Thr Glu Leu Lys Arg Ala Asp Thr Ala Ile Leu
            405             410             415

Phe Ser Ala Glu Ser Glu Trp Ala Thr Arg Ser Glu Thr Leu Pro Ser
            420             425             430

Met Lys Leu Asn His Trp His Asp Val Arg Asp Trp Tyr Arg Gly Tyr
        435             440             445

Leu Asp Ala Gly Ala Arg Ala Asp Val Val Pro Leu Ala Tyr Asp Trp
    450             455             460

Ser Gly Tyr Gln Thr Ile Val Leu Pro Thr Val Ile Ala Leu Ser Asp
465             470             475                 480

Glu Asp Thr Arg Arg Ile Ala Asp Phe Ala Glu Asn Gly Gly Thr Val
            485             490             495

Ile Val Gly Tyr Ala Thr Gly Leu Ile Asp Glu His Phe His Ile Gly
            500             505             510

Leu Gly Gly Tyr Pro Gly Ala Gly Asn Gly Leu Leu Arg Asp Met Leu
        515             520             525

Gly Ile Arg Ser Glu Glu Phe Asn Ile Leu Gly Glu Glu Ala Glu Asp
    530             535             540

Glu Pro Ala Glu Ile Gly Leu Ser Asn Gly Leu Thr Thr Arg Leu Trp
545             550             555                 560

Gln Asn Asp Val Thr Ser Val Ala Pro Asp Thr Arg Val Leu Ala Thr
            565             570             575

Tyr Val Gly Thr Ala Ala Ala Asp Trp Glu Leu Asp Gly Val Pro Ala
            580             585             590

Ile Thr Ser His Pro His Gly Gln Gly Ala Ala Ile Tyr Val Gly Cys
        595             600             605

Asp Leu Gly Arg His Asp Ile Thr His Leu Leu Lys Glu Leu Asn Thr
```

-continued

```
            610              615              620
Thr Ala Pro Ser Asp Glu Arg Ala Pro Asp Gln Arg Pro Gly Gly Gly
625              630              635              640

Glu Ile Asn Ala Ala Thr Thr Thr Ala Ala Ala Thr Thr His Asp Pro
            645              650              655

Arg Ile Leu His Thr Ile Arg Gln Ser Ser Asp Gly Thr Ile Arg Phe
            660              665              670

Asp Phe Tyr Leu Asn Arg Ser Lys Gln Pro Val Ala Val Asn Gly Val
            675              680              685

Glu Gly Asp Pro Ile Ile Ala His Arg Cys Glu Thr Asp Ala Val Gly
            690              695              700

Tyr Thr Leu Asn Arg Asn Ala Ile Leu Ile Ala Lys Thr Ser Cys
705              710              715

<210> SEQ ID NO 16
<211> LENGTH: 672
<212> TYPE: PRT
<213> ORGANISM: Lactobacillus reuteri

<400> SEQUENCE: 16

Met Met Lys Lys Glu Leu Pro Arg Phe Leu Tyr Gly Gly Asp Tyr Asn
1               5                10               15

Pro Glu Gln Trp Pro Glu Glu Thr Trp Asp Glu Asp Ile Lys Val Phe
            20               25               30

Lys Gln Ala Asp Ile Asn Ser Ala Thr Ile Asn Val Phe Ser Trp Ala
            35               40               45

Leu Leu Glu Pro Gln Glu Gly Lys Tyr Asp Phe Thr Lys Leu Asp Lys
            50               55               60

Ile Ile Lys Glu Leu Thr Val Ala Asp Phe Asp Ile Val Leu Ala Thr
65               70               75               80

Ser Thr Ala Ala Met Pro Ala Trp Met Phe Lys Lys Tyr Pro Asp Val
            85               90               95

Ala Arg Val Asp Tyr Gln Gly Arg Arg His Val Phe Gly Ala Arg His
            100              105              110

Asn Phe Cys Pro Ser Ser Lys Asn Tyr Arg Arg Leu Ala Lys Asn Leu
            115              120              125

Val Glu Gln Leu Ala Lys Arg Tyr Gly Asp Asn Pro His Ile Val Ala
            130              135              140

Trp His Val Asn Asn Glu Tyr Gly Gly Asn Cys Tyr Cys Glu Glu Cys
145              150              155              160

Gln Thr Glu Phe Gln Gln Trp Leu Lys Ala Arg Tyr Gln Thr Leu Asp
            165              170              175

Asn Leu Asn His Ala Trp Asn Met Asn Val Trp Ser His Thr Ile His
            180              185              190

Asp Trp Asn Glu Ile Val Val Pro Asn Glu Leu Gly Asp Ala Trp Gly
            195              200              205

Pro Glu Gly Ser Glu Thr Ile Val Ala Gly Leu Ser Ile Asp Tyr Leu
            210              215              220

Arg Phe Gln Ser Ala Gln Met Leu Asp Leu Phe Lys Met Glu Lys Gln
225              230              235              240

Ile Ile Glu Lys Tyr Asp Pro Thr Thr Leu Val Thr Thr Asn Phe His
            245              250              255

Ser Leu Pro Asn Lys Met Ile Asp Tyr Gln Gln Trp Ala Ser Ala Gln
            260              265              270
```

```
Asp Ile Ile Ser Tyr Asp Ser Tyr Pro Ala Tyr Asp Ala Pro Ile Tyr
        275                 280                 285

Gln Pro Ala Phe Leu Tyr Asp Leu Met Arg Ser Leu Lys His Gln Pro
    290                 295                 300

Phe Met Leu Met Glu Ser Thr Pro Ser Gln Val Asn Trp Gln Pro Tyr
305                 310                 315                 320

Ser Pro Leu Lys Arg Pro Gly Gln Met Ala Ala Thr Glu Leu Gln Ala
                325                 330                 335

Val Ala His Gly Ala Asp Thr Val Gln Phe Phe Gln Leu Lys Gln Ala
            340                 345                 350

Leu Gly Gly Ser Glu Lys Phe His Gly Ala Val Ile Ser His Ala Asn
            355                 360                 365

Arg Thr Asp Thr Arg Val Phe Lys Glu Val Ala Lys Leu Gly His Asp
    370                 375                 380

Leu Arg Lys Val Gly Pro Val Ile Lys Asp Ser Gln Thr Lys Ala Arg
385                 390                 395                 400

Val Ala Leu Ile Phe Asp Trp Ser Asn Phe Trp Ser Phe Glu Tyr Val
                405                 410                 415

Asp Gly Ile Thr Gln Asp Leu Lys Tyr Val Pro Ile Ile Leu Asp Tyr
            420                 425                 430

Tyr Arg Gln Phe Tyr Glu Leu Asn Ile Pro Thr Asp Val Ile Ser Val
        435                 440                 445

Asp Asp Asp Phe Arg Gln Tyr Asp Leu Val Val Ala Pro Val Leu Tyr
    450                 455                 460

Met Val Lys Gly Gly Leu Gly Lys Lys Ile Thr Asp Tyr Val Ala Asn
465                 470                 475                 480

Gly Gly Asn Phe Ile Thr Ser Phe Met Ser Gly Met Val Asn Glu Ser
                485                 490                 495

Asp Asn Ile Tyr Pro Gly Gly Tyr Pro Gly Pro Leu Lys Asp Val Met
            500                 505                 510

Gly Leu Trp Val Glu Glu Ser Asp Ala Ile Leu Pro Asn Lys Asp Val
            515                 520                 525

Lys Leu Thr Met Thr Thr Gly Asp Glu Leu Thr Gly Tyr Leu Ile Ala
    530                 535                 540

Asp Leu Ile Arg Leu Asn Gly Ala His Val Leu Ala Glu Tyr Ala Ser
545                 550                 555                 560

Glu Phe Tyr Ala Gly Thr Pro Ala Val Thr Glu Asn Thr Tyr Ser Lys
                565                 570                 575

Gly Lys Ala Trp Tyr Val Gly Ser Arg Leu Asp His Ala Ser Leu Arg
            580                 585                 590

Lys Ile Ile Met His Ile Val Asp Asp Val His Leu Ser Ala Leu Val
            595                 600                 605

Lys Glu Pro Thr Glu Leu Glu Ile Thr Lys Arg Gln Asn Ser Ala Gly
    610                 615                 620

Gln Asp Ile Tyr Phe Val Leu Asn Met Gly Lys Gly Lys Gln Pro Leu
625                 630                 635                 640

Pro Val Glu Phe Gln Lys Gly Tyr Arg Asp Leu Leu Thr Gly Asp Ser
                645                 650                 655

Pro Glu Thr Met Leu Asp Ser Trp Asp Val Glu Ile Leu Val Gln Glu
                660                 665                 670
```

```
<210> SEQ ID NO 17
<211> LENGTH: 1007
<212> TYPE: PRT
```

-continued

<213> ORGANISM: Lactobacillus delbrueckii

<400> SEQUENCE: 17

```
Met Ser Asn Lys Leu Val Lys Glu Lys Arg Val Asp Gln Ala Asp Leu
1               5                   10                  15

Ala Trp Leu Thr Asp Pro Glu Val Tyr Glu Val Asn Thr Ile Pro Pro
                20                  25                  30

His Ser Asp His Glu Ser Phe Gln Ser Gln Glu Glu Leu Glu Glu Gly
            35                  40                  45

Lys Ser Ser Leu Val Gln Ser Leu Asp Gly Asn Trp Leu Ile Asp Tyr
        50                  55                  60

Ala Glu Asn Gly Gln Gly Pro Ile Asn Phe Tyr Ala Glu Asp Phe Asp
65                  70                  75                  80

Asp Ser Asn Phe Lys Ser Val Lys Val Pro Gly Asn Leu Glu Leu Gln
                85                  90                  95

Gly Phe Gly Gln Pro Gln Tyr Val Asn Ile Gln Tyr Pro Trp Asp Gly
            100                 105                 110

Ser Glu Glu Ile Phe Pro Pro Gln Val Pro Ser Lys Asn Pro Leu Ala
        115                 120                 125

Ser Tyr Val Arg Tyr Phe Asp Leu Asp Glu Ala Leu Trp Asp Lys Glu
        130                 135                 140

Val Ser Leu Lys Phe Ala Gly Ala Ala Thr Ala Ile Tyr Val Trp Leu
145                 150                 155                 160

Asn Gly His Phe Val Gly Tyr Gly Glu Asp Ser Phe Thr Pro Ser Glu
                165                 170                 175

Phe Met Val Thr Lys Phe Leu Lys Lys Glu Gly Asn Arg Leu Ala Val
            180                 185                 190

Ala Leu Tyr Lys Tyr Ser Ser Ala Ser Trp Leu Glu Asp Gln Asp Phe
        195                 200                 205

Trp Arg Leu Ser Gly Leu Phe Arg Ser Val Thr Leu Glu Ala Lys Pro
    210                 215                 220

Leu Leu His Leu Glu Asp Leu Lys Leu Thr Ala Ser Leu Thr Asp Asn
225                 230                 235                 240

Tyr Gln Lys Gly Lys Leu Glu Val Glu Ala Asn Ile Ala Tyr Arg Leu
                245                 250                 255

Pro Asn Ala Ser Phe Lys Leu Glu Val Arg Asp Ser Glu Gly Asp Leu
            260                 265                 270

Val Ala Glu Lys Val Gly Pro Ile Arg Ser Glu Lys Leu Gly Phe Ser
        275                 280                 285

Leu Ala Asp Leu Pro Val Ala Ala Trp Ser Ala Glu Lys Pro Asn Leu
    290                 295                 300

Tyr Gln Val Arg Leu Tyr Leu Tyr Gln Ala Gly Ser Leu Leu Glu Val
305                 310                 315                 320

Ser Arg Gln Glu Val Gly Phe Arg Asn Phe Glu Leu Lys Asp Gly Ile
                325                 330                 335

Met Tyr Leu Asn Gly Gln Arg Ile Val Phe Lys Gly Val Asn Arg His
            340                 345                 350

Glu Phe Asp Ser Lys Leu Gly Arg Ala Ile Thr Glu Ala Asp Met Ile
        355                 360                 365

Trp Asp Ile Lys Thr Met Lys Gln Ser Asn Ile Asn Ala Val Arg Cys
    370                 375                 380

Ser His Tyr Pro Asn Gln Ser Leu Phe Tyr Arg Leu Cys Asp Lys Tyr
385                 390                 395                 400
```

-continued

```
Gly Leu Tyr Val Ile Asp Glu Ala Asn Leu Glu Ser His Gly Thr Trp
            405                 410                 415

Glu Lys Val Gly His Glu Asp Pro Ser Phe Asn Val Pro Gly Asp Asp
            420                 425                 430

Gln His Trp Leu Gly Ala Ser Leu Ser Arg Val Lys Asn Met Met Ala
            435                 440                 445

Arg Asp Lys Asn His Ala Ser Ile Leu Ile Trp Ser Leu Gly Asn Glu
    450                 455                 460

Ser Tyr Ala Gly Thr Val Phe Ala Gln Met Ala Asp Tyr Val Arg Lys
465                 470                 475                 480

Ala Asp Pro Thr Arg Val Gln His Tyr Glu Gly Val Thr His Asn Arg
                485                 490                 495

Lys Phe Asp Asp Ala Thr Gln Ile Glu Ser Arg Met Tyr Ala Pro Ala
            500                 505                 510

Lys Glu Ile Glu Glu Tyr Leu Thr Lys Lys Pro Ala Lys Pro Phe Ile
            515                 520                 525

Ser Val Glu Tyr Ala His Ala Met Gly Asn Ser Val Gly Asp Leu Ala
    530                 535                 540

Ala Tyr Thr Ala Leu Glu Lys Tyr Pro His Tyr Gln Gly Gly Phe Ile
545                 550                 555                 560

Trp Asp Trp Ile Asp Gln Gly Leu Glu Lys Asp Gly His Leu Leu Tyr
                565                 570                 575

Gly Gly Asp Phe Asp Asp Arg Pro Thr Asp Tyr Glu Phe Cys Gly Asp
                580                 585                 590

Gly Leu Val Phe Ala Asp Arg Thr Thr Ser Pro Lys Leu Ala Asn Val
            595                 600                 605

Lys Ala Leu Tyr Ser Asn Leu Lys Leu Glu Val Lys Asp Gly Gln Leu
    610                 615                 620

Phe Ile Lys Asn Asp Asn Leu Phe Thr Asn Ser Ser Ala Tyr Tyr Phe
625                 630                 635                 640

Leu Ala Ser Leu Leu Val Asp Gly Lys Leu Thr Tyr Gln Ser Gln Pro
                645                 650                 655

Leu Thr Phe Gly Leu Glu Pro Gly Glu Ser Gly Thr Phe Val Leu Pro
                660                 665                 670

Trp Pro Glu Val Glu Asp Glu Lys Gly Glu Ile Val Tyr Gln Val Thr
            675                 680                 685

Ala His Leu Lys Glu Asp Leu Pro Trp Ala Asp Glu Gly Phe Thr Val
    690                 695                 700

Ala Glu Ala Glu Glu Ala Val Thr Lys Leu Pro Glu Phe Tyr Pro Ala
705                 710                 715                 720

Gly Arg Pro Glu Leu Val Asp Ser Asp Phe Asn Leu Gly Leu Lys Gly
            725                 730                 735

Asn Gly Phe Arg Ile Leu Phe Ser Lys Ala Lys Gly Trp Pro Val Ser
            740                 745                 750

Ile Lys Tyr Ala Gly Arg Glu Tyr Leu Lys Arg Leu Pro Glu Phe Thr
            755                 760                 765

Phe Trp Arg Ala Leu Thr Asp Asn Asp Arg Gly Ala Gly Tyr Gly Tyr
    770                 775                 780

Asp Leu Ala Lys Trp Glu Asn Ala Gly Lys Tyr Ala Arg Leu Gln Asp
785                 790                 795                 800

Ile Ser Tyr Glu Ile Lys Glu Asn Ser Ala Leu Val Lys Thr Thr Phe
                805                 810                 815

Thr Leu Pro Val Ala Leu Lys Gly Asp Leu Thr Ile Thr Tyr Glu Val
```

-continued

```
              820             825             830

Asp Ser Leu Gly Lys Ile Ala Val Thr Ala Asn Phe Pro Gly Ala Val
        835             840             845

Glu Asn Gly Leu Leu Pro Ala Phe Gly Leu Asn Phe Ala Leu Pro Lys
    850             855             860

Glu Leu Ser Asp Tyr Arg Tyr Tyr Gly Leu Gly Pro Asn Glu Ser Tyr
865             870             875             880

Ala Asp Arg Leu Glu Gly Ser Tyr Leu Gly Ile Tyr Gln Gly Ala Val
            885             890             895

Glu Lys Asn Phe Thr Pro Tyr Leu Arg Pro Gln Glu Ala Gly Asn Arg
        900             905             910

Ser Lys Val Arg Tyr Tyr Gln Leu Phe Asp Glu Glu Gly Gly Leu Glu
        915             920             925

Phe Thr Ala Asn Gly Ala Asp Leu Asn Leu Ser Ala Leu Pro Tyr Ser
    930             935             940

Ala Ala Gln Ile Glu Ala Ala Asp His Ala Phe Glu Leu Thr Asn Asn
945             950             955             960

Tyr Thr Trp Val Arg Ala Leu Ala Ala Gln Met Gly Val Gly Gly Asp
            965             970             975

Asp Ser Trp Gly Gln Lys Val His Pro Glu Phe Cys Leu Asp Ala Gln
            980             985             990

Glu Ala Arg Gln Leu Lys Leu Val  Ile Gln Pro Leu Leu  Leu Lys
        995            1000            1005

<210> SEQ ID NO 18
<211> LENGTH: 705
<212> TYPE: PRT
<213> ORGANISM: Bifidobacterium angulatum

<400> SEQUENCE: 18

Met Ala His Arg Arg Thr Phe His Trp Pro Ser Leu Leu Thr Glu Ser
1               5               10              15

Gly Arg Gly Ile Ala Phe Gly Gly Asp Tyr Asn Pro Asp Gln Trp Pro
            20              25              30

Glu Asp Val Trp Asp Asp Asp Ile Arg Leu Met Lys Gln Ala Gly Val
        35              40              45

Asn Thr Val Ala Leu Ala Ile Phe Ser Trp Asp Arg Ile Gln Pro Glu
    50              55              60

Lys His Arg Trp Glu Phe Gly Trp Leu Asp Cys Ile Ile Asp Lys Leu
65              70              75              80

Gly Lys Ala Gly Ile Ala Val Asp Leu Ala Ser Ala Thr Ala Thr Ala
            85              90              95

Pro Leu Trp Leu Tyr Glu Gln His Pro Glu Val Leu Pro His Asp Lys
            100             105             110

Tyr Gly His Pro Ile Asn Ala Gly Ser Arg Gln Ser Trp Ser Pro Thr
        115             120             125

Ser Pro Val Phe Lys Glu Tyr Ala Leu Thr Leu Cys Arg Lys Leu Ala
    130             135             140

Glu Arg Tyr Gly Thr Asn Pro Tyr Val Thr Ala Trp His Met Gly Asn
145             150             155             160

Glu Tyr Gly Trp Asn Asn Arg Tyr Asp Tyr Cys Asp Asn Ala Leu His
            165             170             175

Ala Phe Arg Ala Trp Cys Glu Arg Lys Tyr Gly Thr Ile Glu Ala Leu
            180             185             190
```

-continued

```
Asn Ala Ala Trp Gly Thr Thr Phe Trp Gly Gln Glu Met Asn Gly Phe
        195                 200                 205

Asp Glu Val Leu Ile Pro Arg Phe Met Gly Ala Asp Ser Met Val Asn
        210                 215                 220

Pro Gly Gln Lys Leu Asp Phe Glu Arg Phe Gly Asn Asp Met Leu Leu
225                 230                 235                 240

Asp Phe Tyr Arg Ala Glu Arg Asp Ala Ile Ala Glu Ile Cys Pro Asp
                245                 250                 255

Lys Pro Phe Thr Thr Asn Phe Met Val Ser Thr Asp Gln Cys Cys Met
                260                 265                 270

Asp Tyr Ala Asp Trp Ala Asn Glu Val Asp Phe Val Ser Asn Asp His
        275                 280                 285

Tyr Phe His Glu Gly Glu Ser His Ile Asp Glu Leu Phe Cys Ser Asp
        290                 295                 300

Ala Leu Met Asp Ser Leu Ala Leu Gly Arg Pro Trp Tyr Val Met Glu
305                 310                 315                 320

His Ser Thr Ser Ala Val Gln Trp Lys Asp Leu Asn Ile Arg Lys Arg
                325                 330                 335

Lys Gly Glu Thr Val Arg Asp Ser Val Ala His Val Ala Met Gly Ala
                340                 345                 350

Asp Ala Ile Asn Phe Phe Gln Trp Arg Ala Ser Ala Phe Gly Ala Glu
        355                 360                 365

Ser Phe His Ser Ala Met Val Pro His Ala Gly Glu His Thr Lys Leu
        370                 375                 380

Tyr Arg Ser Val Cys Glu Leu Gly Ala Ala Leu Lys Thr Leu Gly Asp
385                 390                 395                 400

Ala Gly Val Gln Gly Ser Glu Leu Val Arg Ser Asp Thr Ala Ile Leu
                405                 410                 415

Phe Ser Ala Glu Ser Glu Trp Ala Thr Arg Ser Glu Thr Leu Pro Ser
                420                 425                 430

Lys Lys Leu Asn His Trp His Asp Val Arg Asp Trp Tyr Arg Ala Tyr
        435                 440                 445

Leu Asp Ala Gly Thr Arg Ala Asp Ile Val Pro Leu Lys Tyr Asp Trp
        450                 455                 460

Ser Gly Tyr Ala Thr Val Val Leu Pro Thr Val Leu Met Leu Ser Ala
465                 470                 475                 480

Ala Asp Thr Ala Arg Leu Glu Arg Phe Val Arg Asp Gly Gly Thr Val
                485                 490                 495

Val Val Gly Tyr Ala Ser Gly Leu Ile Asp Glu Asn Phe His Thr Trp
                500                 505                 510

Leu Gly Gly Tyr Pro Gly Ala Gly Asp Gly Met Leu Arg Thr Met Leu
        515                 520                 525

Gly Ile Arg Gly Glu Glu Phe Asn Ile Leu Gly Ala Gln Ala Glu Gly
        530                 535                 540

Glu Pro Ser Glu Ile Arg Leu Ser Asn Gly Met Val Thr Arg Leu Trp
545                 550                 555                 560

Gln Asn Asp Ile Ala Val Asp Gly Ala Asp Thr Glu Val Leu Ala Ser
                565                 570                 575

Tyr Ala Gly Thr Gln Ala Asp Glu Trp Glu Leu Asp Gly Thr Ala Ala
        580                 585                 590

Ile Thr Arg Asn Pro Tyr Gly Lys Gly Met Ala Tyr Phe Val Gly Cys
        595                 600                 605

Asp Leu Asn Val Ala Asp Leu Ala Val Phe Val Gly Asp His Leu Thr
```

-continued

```
                610                 615                 620

Val Gly Gln Ala Cys Glu Ala Gly Asp Gly Ala Asp Tyr Asp Pro Thr
625                 630                 635                 640

Ile Thr Leu His Thr Glu Arg Ala Ser Ala Glu Ala Ile Phe Asp Phe
                645                 650                 655

Tyr Leu Pro Arg Gly Lys Asn Glu Thr Val Val Ser Gly Ile Ser Gly
                660                 665                 670

Glu Pro Val Tyr Arg Phe Gln Cys Asp Glu Gly Glu Ala Pro Gly Val
                675                 680                 685

Tyr Thr Ile Arg Arg Asn Gly Val Leu Val Val Lys Arg Tyr Asn Arg
                690                 695                 700

Gln
705

<210> SEQ ID NO 19
<211> LENGTH: 626
<212> TYPE: PRT
<213> ORGANISM: Lactobacillus fermentum

<400> SEQUENCE: 19

Met Glu Ala Glu Leu Lys Trp Leu Asp Asp Pro Glu Val Phe Arg Val
1               5                   10                  15

Asn Gln Leu Pro Ala His Ser Asp His Arg Phe Tyr Arg Asp Gln Glu
                20                  25                  30

Glu Ala Ala Leu Glu Lys Ser Ser Tyr Val Gln Asn Leu Asn Gly Arg
                35                  40                  45

Trp Gly Phe Lys Phe Ser Lys Asn Pro Met Glu Arg Pro Val Asp Phe
        50                  55                  60

Tyr Lys Leu Asp Phe Asp Arg Asn Asp Phe Gly Glu Ile Glu Val Pro
65                  70                  75                  80

Ser Glu Ile Glu Leu Ser Asn Phe Ala Gln Ile Asn Tyr Thr Asn Ile
                85                  90                  95

Thr Met Pro Trp Thr Gly Lys Ile Tyr Arg Arg Pro Ala Tyr Thr Leu
                100                 105                 110

Gly Asp Asn Lys Glu Glu Gly Ser Phe Ser Gln Gly Gln Asp Asn Thr
                115                 120                 125

Val Gly Ser Tyr Val Arg His Phe Thr Leu Ala Glu Gly Leu Lys Asn
        130                 135                 140

His Asp Val His Val Val Phe Glu Gly Val Glu Arg Ala Met Tyr Val
145                 150                 155                 160

Trp Leu Asn Gly His Phe Ile Gly Tyr Ala Glu Asp Ser Phe Thr Pro
                165                 170                 175

Ser Glu Phe Asp Leu Thr Pro Tyr Leu Val Asp Gly Asp Asn Leu Leu
                180                 185                 190

Ala Val Glu Val Tyr Lys His Ala Thr Ser Ser Trp Ile Glu Asp Gln
                195                 200                 205

Asp Met Phe Arg Phe Ser Gly Ile Phe Arg Asp Val Asn Leu Val Ala
        210                 215                 220

Gln Pro Ser Ile His Val Gln Asp Leu Lys Ile Asn Ala Arg Val Ala
225                 230                 235                 240

Asp Asp Met Lys Thr Gly Ser Leu Gly Leu Val Leu Lys Met Val Gly
                245                 250                 255

Gln Pro Gly Ser Val Gln Val Glu Val Ala Asp Gln Thr Gly Ala Ala
                260                 265                 270
```

-continued

```
Val Leu Asn Arg Gln Leu Asn Ala Asp Gly Asn Trp Thr Met Ala Pro
        275                 280                 285

Val Gln Leu Val Gly Ile His Leu Trp Asp Asn His His Pro Tyr Leu
        290                 295                 300

Tyr Gln Leu Thr Leu Thr Val Arg Asp Ala Thr Gly Arg Val Val Glu
305                 310                 315                 320

Val Ile Pro Tyr Gln Phe Gly Phe Arg Arg Val Glu Ile Asp Gln Asp
                325                 330                 335

Lys Val Leu Arg Leu Asn Gly Lys Arg Leu Ile Ile Asn Gly Val Asn
            340                 345                 350

Arg His Glu Trp Asn Cys His Arg Gly Arg Ala Val Thr Ile Glu Asp
            355                 360                 365

Met His Thr Asp Leu Gly Ile Phe Lys Glu Asn Asn Ile Asn Ala Val
        370                 375                 380

Arg Thr Ser His Tyr Pro Asp Gln Ile Pro Trp Tyr Tyr Leu Cys Asp
385                 390                 395                 400

Arg Glu Gly Ile Tyr Met Met Ala Glu Asn Asn Leu Glu Ser His Ala
                405                 410                 415

Thr Trp Gln Lys Phe Gly Gln Asp Glu Pro Ser Tyr Asn Val Pro Gly
            420                 425                 430

Ser Leu Pro Gln Trp Lys Glu Ala Val Val Asp Arg Ala Arg Ser Asn
        435                 440                 445

Tyr Glu Ile Phe Lys Asn His Thr Ala Ile Leu Phe Trp Ser Val Gly
        450                 455                 460

Asn Glu Ser Tyr Ala Gly Glu Asp Ile Leu Ala Met Asn Asn Tyr Tyr
465                 470                 475                 480

Lys Glu Val Asp Asp Thr Arg Pro Val His Tyr Glu Gly Val Val His
                485                 490                 495

Thr Lys Glu Tyr Arg Asp Gln Ile Ser Asp Phe Glu Ser Trp Met Tyr
            500                 505                 510

Leu Pro Pro Lys Glu Val Glu Ala Tyr Leu Lys Lys Asn Pro Asp Lys
            515                 520                 525

Pro Phe Ile Glu Cys Glu Tyr Met His Ser Met Gly Asn Ser Val Gly
        530                 535                 540

Gly Met Gly Ser Tyr Ile Lys Leu Leu Asp Lys Tyr Pro Gln Tyr Cys
545                 550                 555                 560

Gly Gly Phe Ile Trp Asp Phe Val Asp Gln Ala Ile Glu Val Val Asp
                565                 570                 575

Pro Val Thr Gly Gln Lys Ser Met Arg Tyr Gly Gly Asp Phe Asp Asp
            580                 585                 590

His His Ala Asp Asn Glu Phe Ser Gly Asp Gly Ile Cys Phe Ala Asp
        595                 600                 605

Arg Thr Pro Lys Pro Ala Met Gln Glu Val Lys Tyr Tyr Tyr Gly Leu
        610                 615                 620

His Lys
625
```

```
<210> SEQ ID NO 20
<211> LENGTH: 320
<212> TYPE: PRT
<213> ORGANISM: Lactobacillus fermentum

<400> SEQUENCE: 20

Met Asp Tyr Thr Asn Lys Leu His Val Val Tyr Asp Asp Asn Ile Leu
1               5                   10                  15
```

-continued

Gly Leu Asp Gly Lys Asp Phe Gln Tyr Leu Phe Ser Tyr Glu Gln Gly
            20                  25                  30

Gly Pro Glu Ser Phe Lys Ile Lys Gly Lys Glu Trp Leu Tyr Arg Ser
            35                  40                  45

Pro Arg Pro Thr Phe Trp Arg Ala Thr Thr Asp Asn Asp Arg Gly Asn
    50                  55                  60

Gly Phe Asn Val Ser Ser Val Gln Trp Leu Ala Ala Asp Tyr Val Leu
65                  70                  75                  80

Pro Cys Gln Asp Ile Ala Leu Gln Val Asp Gly Lys Asp Lys Lys Leu
                85                  90                  95

Pro Leu Ala Pro Lys Thr Asn Arg Tyr Ser Asn Gln Glu Phe Ala Lys
            100                 105                 110

Lys Val Lys Ile Thr Phe Thr Tyr Gln Thr Gln Thr Val Pro Ala Thr
            115                 120                 125

Thr Val Gln Val Ser Tyr Thr Val Lys Ala Ser Gly Lys Ile Lys Val
    130                 135                 140

Asn Val His Tyr Thr Gly Ala Gln Leu Pro Ser Leu Pro Val Leu Gly
145                 150                 155                 160

Trp Arg Met Ile Met Pro Thr Pro Ala Thr Ser Phe Asp Tyr Glu Gly
            165                 170                 175

Leu Ser Gly Glu Thr Tyr Pro Asp Arg Met Ala Gly Gly Ile Glu Gly
            180                 185                 190

Thr Tyr His Val Glu Gly Leu Pro Val Thr Pro Tyr Leu Val Pro Gln
            195                 200                 205

Glu Asn Gly Met His Met Ala Asn Lys Trp Val Gln Ile Thr Arg Ala
    210                 215                 220

Thr Thr Leu Asn Asn Ala Asp Pro Asp Ala Ala Pro Phe Arg Leu Lys
225                 230                 235                 240

Phe Glu Ala Pro Lys Lys Gly Lys Leu Asn Phe Ser Cys Leu Pro Tyr
                245                 250                 255

Thr Ser Ala Glu Leu Glu Asn Ala Thr His Pro Glu Glu Leu Pro Ala
            260                 265                 270

Ala His Arg Thr Val Leu Val Ile Ala Gly Glu Val Arg Gly Val Gly
            275                 280                 285

Gly Ile Asp Ser Trp Gly Ala Asp Val Glu Glu Lys Tyr His Ile Asp
    290                 295                 300

Ala Thr Val Asp His Asp Phe Ser Phe Lys Ile Val Pro Glu Leu Asn
305                 310                 315                 320

<210> SEQ ID NO 21
<211> LENGTH: 1025
<212> TYPE: PRT
<213> ORGANISM: Kluyveromyces lactis

<400> SEQUENCE: 21

Met Ser Cys Leu Ile Pro Glu Asn Leu Arg Asn Pro Lys Lys Val His
1               5                   10                  15

Glu Asn Arg Leu Pro Thr Arg Ala Tyr Tyr Tyr Asp Gln Asp Ile Phe
            20                  25                  30

Glu Ser Leu Asn Gly Pro Trp Ala Phe Ala Leu Phe Asp Ala Pro Leu
            35                  40                  45

Asp Ala Pro Asp Ala Lys Asn Leu Asp Trp Glu Thr Ala Lys Lys Trp
    50                  55                  60

Ser Thr Ile Ser Val Pro Ser His Trp Glu Leu Gln Glu Asp Trp Lys

-continued

```
65                  70                  75                  80

Tyr Gly Lys Pro Ile Tyr Thr Asn Val Gln Tyr Pro Ile Pro Ile Asp
                85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
            115                 120                 125

Phe Glu Gly Val Asp Asn Cys Tyr Glu Leu Tyr Val Asn Gly Gln Tyr
        130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Val Lys Val Phe Lys
                165                 170                 175

Trp Ser Asp Ser Thr Tyr Ile Glu Asp Gln Asp Gln Trp Trp Leu Ser
            180                 185                 190

Gly Ile Tyr Arg Asp Val Ser Leu Leu Lys Leu Pro Lys Lys Ala His
        195                 200                 205

Ile Glu Asp Val Arg Val Thr Thr Thr Phe Val Asp Ser Gln Tyr Gln
        210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
                245                 250                 255

Asp Ala Ser Ser Leu Leu Asn Glu Glu Asn Gly Asn Thr Thr Phe Ser
            260                 265                 270

Thr Lys Glu Phe Ile Ser Phe Ser Thr Lys Lys Asn Glu Glu Thr Ala
        275                 280                 285

Phe Lys Ile Asn Val Lys Ala Pro Glu His Trp Thr Ala Glu Asn Pro
        290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                325                 330                 335

Asp Gly Asn Ile Thr Val Asn Gly Lys Asp Ile Leu Phe Arg Gly Val
            340                 345                 350

Asn Arg His Asp His His Pro Arg Phe Gly Arg Ala Val Pro Leu Asp
        355                 360                 365

Phe Val Val Arg Asp Leu Ile Leu Met Lys Lys Phe Asn Ile Asn Ala
        370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
            405                 410                 415

Gly Val Gln Glu Pro Phe Asn Arg His Thr Asn Leu Glu Ala Glu Tyr
        420                 425                 430

Pro Asp Thr Lys Asn Lys Leu Tyr Asp Val Asn Ala His Tyr Leu Ser
        435                 440                 445

Asp Asn Pro Glu Tyr Glu Val Ala Tyr Leu Asp Arg Ala Ser Gln Leu
        450                 455                 460

Val Leu Arg Asp Val Asn His Pro Ser Ile Ile Ile Trp Ser Leu Gly
465                 470                 475                 480

Asn Glu Ala Cys Tyr Gly Arg Asn His Lys Ala Met Tyr Lys Leu Ile
            485                 490                 495
```

-continued

```
Lys Gln Leu Asp Pro Thr Arg Leu Val His Tyr Glu Gly Asp Leu Asn
        500                 505                 510

Ala Leu Ser Ala Asp Ile Phe Ser Phe Met Tyr Pro Thr Phe Glu Ile
        515                 520                 525

Met Glu Arg Trp Arg Lys Asn His Thr Asp Glu Asn Gly Lys Phe Glu
        530                 535                 540

Lys Pro Leu Ile Leu Cys Glu Tyr Gly His Ala Met Gly Asn Gly Pro
545                 550                 555                 560

Gly Ser Leu Lys Glu Tyr Gln Glu Leu Phe Tyr Lys Glu Lys Phe Tyr
                565                 570                 575

Gln Gly Gly Phe Ile Trp Glu Trp Ala Asn His Gly Ile Glu Phe Glu
                580                 585                 590

Asp Val Ser Thr Ala Asp Gly Lys Leu His Lys Ala Tyr Ala Tyr Gly
        595                 600                 605

Gly Asp Phe Lys Glu Glu Val His Asp Gly Val Phe Ile Met Asp Gly
        610                 615                 620

Leu Cys Asn Ser Glu His Asn Pro Thr Pro Gly Leu Val Glu Tyr Lys
625                 630                 635                 640

Lys Val Ile Glu Pro Val His Ile Lys Ile Ala His Gly Ser Val Thr
                645                 650                 655

Ile Thr Asn Lys His Asp Phe Ile Thr Thr Asp His Leu Leu Phe Ile
                660                 665                 670

Asp Lys Asp Thr Gly Lys Thr Ile Asp Val Pro Ser Leu Lys Pro Glu
        675                 680                 685

Glu Ser Val Thr Ile Pro Ser Asp Thr Thr Tyr Val Val Ala Val Leu
        690                 695                 700

Lys Asp Asp Ala Gly Val Leu Lys Ala Gly His Glu Ile Ala Trp Gly
705                 710                 715                 720

Gln Ala Glu Leu Pro Leu Lys Val Pro Asp Phe Val Thr Glu Thr Ala
                725                 730                 735

Glu Lys Ala Ala Lys Ile Asn Asp Gly Lys Arg Tyr Val Ser Val Glu
                740                 745                 750

Ser Ser Gly Leu His Phe Ile Leu Asp Lys Leu Leu Gly Lys Ile Glu
        755                 760                 765

Ser Leu Lys Val Lys Gly Lys Glu Ile Ser Ser Lys Phe Glu Gly Ser
        770                 775                 780

Ser Ile Thr Phe Trp Arg Pro Pro Thr Asn Asn Asp Glu Pro Arg Asp
785                 790                 795                 800

Phe Lys Asn Trp Lys Lys Tyr Asn Ile Asp Leu Met Lys Gln Asn Ile
                805                 810                 815

His Gly Val Ser Val Glu Lys Gly Ser Asn Gly Ser Leu Ala Val Val
                820                 825                 830

Thr Val Asn Ser Arg Ile Ser Pro Val Val Phe Tyr Tyr Gly Phe Glu
        835                 840                 845

Thr Val Gln Lys Tyr Thr Ile Phe Ala Asn Lys Ile Asn Leu Asn Thr
        850                 855                 860

Ser Met Lys Leu Thr Gly Glu Tyr Gln Pro Pro Asp Phe Pro Arg Val
865                 870                 875                 880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
                900                 905                 910
```

-continued

```
Phe Gly Leu Tyr Asp Ser Lys Asp Val Glu Glu Phe Val Tyr Asp Tyr
        915                 920                 925

Pro Gln Glu Asn Gly Asn His Thr Asp Thr His Phe Leu Asn Ile Lys
        930                 935                 940

Phe Glu Gly Ala Gly Lys Leu Ser Ile Phe Gln Lys Glu Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
                980                 985                 990

Ile His Gly Val Gly Ser Glu Ala  Cys Gly Pro Ala Val  Leu Asp Gln
        995                 1000                1005

Tyr Arg  Leu Lys Ala Gln Asp  Phe Asn Phe Glu Phe  Asp Leu Ala
    1010                1015                1020

Phe Glu
    1025

<210> SEQ ID NO 22
<211> LENGTH: 1305
<212> TYPE: PRT
<213> ORGANISM: Bifidobacterium bifidum

<400> SEQUENCE: 22

Met Val Glu Asp Ala Thr Arg Ser Asp Ser Thr Thr Gln Met Ser Ser
1               5                   10                  15

Thr Pro Glu Val Val Tyr Ser Ser Ala Val Asp Ser Lys Gln Asn Arg
                20                  25                  30

Thr Ser Asp Phe Asp Ala Asn Trp Lys Phe Met Leu Ser Asp Ser Val
            35                  40                  45

Gln Ala Gln Asp Pro Ala Phe Asp Asp Ser Ala Trp Gln Gln Val Asp
        50                  55                  60

Leu Pro His Asp Tyr Ser Ile Thr Gln Lys Tyr Ser Gln Ser Asn Glu
65                  70                  75                  80

Ala Glu Ser Ala Tyr Leu Pro Gly Gly Thr Gly Trp Tyr Arg Lys Ser
                85                  90                  95

Phe Thr Ile Asp Arg Asp Leu Ala Gly Lys Arg Ile Ala Ile Asn Phe
            100                 105                 110

Asp Gly Val Tyr Met Asn Ala Thr Val Trp Phe Asn Gly Val Lys Leu
        115                 120                 125

Gly Thr His Pro Tyr Gly Tyr Ser Pro Phe Ser Phe Asp Leu Thr Gly
        130                 135                 140

Asn Ala Lys Phe Gly Gly Glu Asn Thr Ile Val Val Lys Val Glu Asn
145                 150                 155                 160

Arg Leu Pro Ser Ser Arg Trp Tyr Ser Gly Ser Gly Ile Tyr Arg Asp
                165                 170                 175

Val Thr Leu Thr Val Thr Asp Gly Val His Val Gly Asn Asn Gly Val
            180                 185                 190

Ala Ile Lys Thr Pro Ser Leu Ala Thr Gln Asn Gly Gly Asn Val Thr
            195                 200                 205

Met Asn Leu Thr Thr Lys Val Ala Asn Asp Thr Glu Ala Ala Ala Asn
        210                 215                 220

Ile Thr Leu Lys Gln Thr Val Phe Pro Lys Gly Gly Lys Thr Asp Ala
225                 230                 235                 240

Ala Ile Gly Thr Val Thr Thr Ala Ser Lys Ser Ile Ala Ala Gly Ala
                245                 250                 255
```

-continued

```
Ser Ala Asp Val Thr Ser Thr Ile Thr Ala Ala Ser Pro Lys Leu Trp
            260                 265                 270

Ser Ile Lys Asn Pro Asn Leu Tyr Thr Val Arg Thr Glu Val Leu Asn
            275                 280                 285

Gly Asp Thr Val Leu Asp Thr Tyr Asp Thr Glu Tyr Gly Phe Arg Trp
            290                 295                 300

Thr Gly Phe Asp Ala Thr Ser Gly Phe Ser Leu Asn Gly Glu Lys Val
305                 310                 315                 320

Lys Leu Lys Gly Val Ser Met His His Asp Gln Gly Ser Leu Gly Ala
                325                 330                 335

Val Ala Asn Arg Arg Ala Ile Glu Arg Gln Val Glu Ile Leu Gln Lys
                340                 345                 350

Met Gly Val Asn Ser Ile Arg Thr Thr His Asn Pro Ala Ala Lys Ala
                355                 360                 365

Leu Ile Asp Val Cys Asn Glu Lys Gly Val Leu Val Val Glu Glu Val
            370                 375                 380

Phe Asp Met Trp Asn Arg Ser Lys Asn Gly Asn Thr Glu Asp Tyr Gly
385                 390                 395                 400

Lys Trp Phe Gly Gln Thr Ile Ala Gly Asp Asn Ala Val Leu Gly Gly
                405                 410                 415

Asp Lys Asp Glu Thr Trp Ala Lys Phe Asp Leu Thr Ser Thr Ile Asn
                420                 425                 430

Arg Asp Arg Asn Ala Pro Ser Val Ile Met Trp Ser Leu Gly Asn Glu
                435                 440                 445

Met Met Glu Gly Ile Ser Gly Ser Val Ser Asp Phe Pro Ala Thr Ser
            450                 455                 460

Ala Lys Leu Val Ala Trp Thr Lys Ala Ala Asp Ser Thr Arg Pro Met
465                 470                 475                 480

Thr Tyr Gly Asp Asn Lys Ile Lys Ala Asn Trp Asn Glu Ser Asn Thr
                485                 490                 495

Met Gly Asp Asn Leu Thr Ala Asn Gly Gly Val Val Gly Thr Asn Tyr
                500                 505                 510

Ser Asp Gly Ala Asn Tyr Asp Lys Ile Arg Thr Thr His Pro Ser Trp
            515                 520                 525

Ala Ile Tyr Gly Ser Glu Thr Ala Ser Ala Ile Asn Ser Arg Gly Ile
            530                 535                 540

Tyr Asn Arg Thr Thr Gly Gly Ala Gln Ser Ser Asp Lys Gln Leu Thr
545                 550                 555                 560

Ser Tyr Asp Asn Ser Ala Val Gly Trp Gly Ala Val Ala Ser Ser Ala
                565                 570                 575

Trp Tyr Asp Val Val Gln Arg Asp Phe Val Ala Gly Thr Tyr Val Trp
                580                 585                 590

Thr Gly Phe Asp Tyr Leu Gly Glu Pro Thr Pro Trp Asn Gly Thr Gly
            595                 600                 605

Ser Gly Ala Val Gly Ser Trp Pro Ser Pro Lys Asn Ser Tyr Phe Gly
            610                 615                 620

Ile Val Asp Thr Ala Gly Phe Pro Lys Asp Thr Tyr Tyr Phe Tyr Gln
625                 630                 635                 640

Ser Gln Trp Asn Asp Asp Val His Thr Leu His Ile Leu Pro Ala Trp
                645                 650                 655

Asn Glu Asn Val Val Ala Lys Gly Ser Gly Asn Lys Val Pro Val Val
                660                 665                 670
```

-continued

```
Val Tyr Thr Asp Ala Ala Lys Val Lys Leu Tyr Phe Thr Pro Lys Gly
        675             680             685

Ser Thr Glu Lys Arg Leu Ile Gly Glu Lys Ser Phe Thr Lys Lys Thr
    690             695             700

Thr Ala Ala Gly Tyr Thr Tyr Gln Val Tyr Glu Gly Thr Asp Lys Asp
705             710             715             720

Ser Thr Ala His Lys Asn Met Tyr Leu Thr Trp Asn Val Pro Trp Ala
            725             730             735

Glu Gly Thr Ile Ser Ala Glu Ala Tyr Asp Glu Asn Asn Arg Leu Ile
            740             745             750

Pro Glu Gly Ser Thr Glu Gly Asn Ala Ser Val Thr Thr Thr Gly Lys
            755             760             765

Ala Ala Lys Leu Lys Ala Asp Ala Asp Arg Lys Thr Ile Thr Ala Asp
    770             775             780

Gly Lys Asp Leu Ser Tyr Ile Glu Val Asp Val Thr Asp Ala Asn Gly
785             790             795             800

His Ile Val Pro Asp Ala Ala Asn Arg Val Thr Phe Asp Val Lys Gly
            805             810             815

Ala Gly Lys Leu Val Gly Val Asp Asn Gly Ser Ser Pro Asp His Asp
            820             825             830

Ser Tyr Gln Ala Asp Asn Arg Lys Ala Phe Ser Gly Lys Val Leu Ala
            835             840             845

Ile Val Gln Ser Thr Lys Glu Ala Gly Glu Ile Thr Val Thr Ala Lys
    850             855             860

Ala Asp Gly Leu Gln Ser Ser Thr Val Lys Ile Ala Thr Thr Ala Val
865             870             875             880

Pro Gly Thr Ser Thr Glu Lys Thr Val Arg Ser Phe Tyr Tyr Ser Arg
            885             890             895

Asn Tyr Tyr Val Lys Thr Gly Asn Lys Pro Ile Leu Pro Ser Asp Val
            900             905             910

Glu Val Arg Tyr Ser Asp Gly Thr Ser Asp Arg Gln Asn Val Thr Trp
            915             920             925

Asp Ala Val Ser Asp Asp Gln Ile Ala Lys Ala Gly Ser Phe Ser Val
    930             935             940

Ala Gly Thr Val Ala Gly Gln Lys Ile Ser Val Arg Val Thr Met Ile
945             950             955             960

Asp Glu Ile Gly Ala Leu Leu Asn Tyr Ser Ala Ser Thr Pro Val Gly
            965             970             975

Thr Pro Ala Val Leu Pro Gly Ser Arg Pro Ala Val Leu Pro Asp Gly
            980             985             990

Thr Val Thr Ser Ala Asn Phe Ala  Val His Trp Thr Lys  Pro Ala Asp
            995             1000            1005

Thr Val  Tyr Asn Thr Ala Gly  Thr Val Lys Val Pro  Gly Thr Ala
    1010            1015            1020

Thr Val  Phe Gly Lys Glu Phe  Lys Val Thr Ala Thr  Ile Arg Val
    1025            1030            1035

Gln Arg  Ser Gln Val Thr Ile  Gly Ser Ser Val Ser  Gly Asn Ala
    1040            1045            1050

Leu Arg  Leu Thr Gln Asn Ile  Pro Ala Asp Lys Gln  Ser Asp Thr
    1055            1060            1065

Leu Asp  Ala Ile Lys Asp Gly  Ser Thr Thr Val Asp  Ala Asn Thr
    1070            1075            1080

Gly Gly  Gly Ala Asn Pro Ser  Ala Trp Thr Asn Trp  Ala Tyr Ser
```

-continued

```
        1085                    1090                    1095

Lys Ala  Gly His Asn Thr Ala  Glu Ile Thr Phe Glu  Tyr Ala Thr
    1100                    1105                    1110

Glu Gln  Gln Leu Gly Gln Ile  Val Met Tyr Phe Phe  Arg Asp Ser
    1115                    1120                    1125

Asn Ala  Val Arg Phe Pro Asp  Ala Gly Lys Thr Lys  Ile Gln Ile
    1130                    1135                    1140

Ser Ala  Asp Gly Lys Asn Trp  Thr Asp Leu Ala Ala  Thr Glu Thr
    1145                    1150                    1155

Ile Ala  Ala Gln Glu Ser Ser  Asp Arg Val Lys Pro  Tyr Thr Tyr
    1160                    1165                    1170

Asp Phe  Ala Pro Val Gly Ala  Thr Phe Val Lys Val  Thr Val Thr
    1175                    1180                    1185

Asn Ala  Asp Thr Thr Thr Pro  Ser Gly Val Val Cys  Ala Gly Leu
    1190                    1195                    1200

Thr Glu  Ile Glu Leu Lys Thr  Ala Thr Ser Lys Phe  Val Thr Asn
    1205                    1210                    1215

Thr Ser  Ala Ala Leu Ser Ser  Leu Thr Val Asn Gly  Thr Lys Val
    1220                    1225                    1230

Ser Asp  Ser Val Leu Ala Ala  Gly Ser Tyr Asn Thr  Pro Ala Ile
    1235                    1240                    1245

Ile Ala  Asp Val Lys Ala Glu  Gly Glu Gly Asn Ala  Ser Val Thr
    1250                    1255                    1260

Val Leu  Pro Ala His Asp Asn  Val Ile Arg Val Ile  Thr Glu Ser
    1265                    1270                    1275

Glu Asp  His Val Thr Arg Lys  Thr Phe Thr Ile Asn  Leu Gly Thr
    1280                    1285                    1290

Glu Gln  Glu Phe Pro Ala Asp  Ser Asp Glu Arg Asp
    1295                    1300                    1305

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
attaaccaug cgacgcaact tcgaatggcc                                      30

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
atcttctcut taccgcctta ccacgagcac g                                    31

<210> SEQ ID NO 25
<211> LENGTH: 33
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
agagaagaut ttcagcctga tacagattaa atc                                33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
atggttaaut cctcctgtta gcccaaaaaa cgg                                33

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cggcgtcaca ctttgctatg cc                                            22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgcgctact gccgccaggc                                               20
```

LACTASE ENZYMES WITH IMPROVED PROPERTIES AT ACIDIC PH

CROSS-REFERENCE TO RELATED APPLICATIONS

The present application is the U.S. National Stage of International Application No. PCT/EP2019/078150, filed Oct. 17, 2019, and claims priority to European Patent Application No. 18200994.4, filed Oct. 17, 2018.

SEQUENCE LISTING

The instant application contains a Sequence Listing which has been submitted electronically in ASCII format and is hereby incorporated by reference in its entirety. Said ASCII copy, created on Aug. 16, 2021, is named 030427-0346_SL.txt and is 135,972 bytes in size.

FIELD OF THE INVENTION

The present invention relates to new improved peptide or dimeric peptides exhibiting beta-galactosidase enzyme activity as well as improved methods for reducing the lactose content in compositions, such as dairy products.

BACKGROUND OF THE INVENTION

In order to grow on milk, lactose hydrolysis is a good way for lactic acid bacteria to obtain glucose and galactose as carbon source. Lactase (beta-galactosidase; EC 3.2.1.23) is the enzyme that performs the hydrolysis step of the milk sugar lactose into monosaccharides. The commercial use of lactase is to break down lactose in dairy products. Lactose intolerant people have difficulties to digest dairy products with high lactose levels. It is estimated that about 70% of the world's population has a limited ability to digest lactose. Accordingly, there is a growing demand for dairy food products that contain no or only low levels of lactose.

Lactases have been isolated from a large variety of organisms, including microorganisms like *Kluyveromyces* and *Bacillus*. *Kluyveromyces*, especially *K. fragilis* and *K. lactis*, and other fungi such as those of the genera *Candida, Torula* and *Torulopsis,* are a common source of fungal lactases, whereas *B. coagulans* and *B. circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so-called neutral lactases having a pH optimum between pH 6 and pH 8, as well as a temperature optimum around 37° C. When such lactases are used in the production of, e.g. low-lactose yoghurt, the enzyme treatment will either have to be done in a separate step before fermentation or rather high enzyme dosages have to be used because their activity will drop as the pH decreases during fermentation.

WO 2009/071539 discloses a lactase originating from *Bifidobacterium bifidum,* which is capable of very efficient hydrolysis in milk, and which is active over a broad pH range, including low pH, e.g. a pH below 6. The lactase may be used in processes for producing milk and fermented milk products, such as cheese, yogurt, butter, butter milk, sour cream etc., for reducing the content of lactose.

WO 2013/160413 discloses a method of producing a fermented milk product using a combination of glucose-negative lactic acid bacteria strains and a conventional lactase with an object of reducing the content of lactose in the fermented milk product while increasing the content of glucose.

EP-A1-2 957 180 discloses a method of producing a fermented milk product using a combination of a starter cultures and a conventional lactase with an object of reducing content of lactose and the level of post-acidification in the fermented milk product.

WO2017216000 discloses a process for producing an acidified milk product comprising the steps of providing a basic acidified milk product, which has a pH of between 3.0 and 5.0 and a content of lactose of at least 1.5 mg/ml, adding to the basic acidified milk product a lactase, which retains its activity at a pH of 5.0 and a temperature of 37° C. at a level of at least 5% as compared to its activity at the optimum pH of the lactase, e.g. a lactase originating from *Bifidobacterium bifidum* with an activity optimum at a pH of 6.0 as measured at a temperature of 37° C.

OBJECT OF THE INVENTION

It is an object of embodiments of the invention to provide beta-galactosidases with properties that enable the production of improved lactose-free or low-lactose products under acidic conditions.

The object of the present invention is to provide an improved process for producing an acidified milk product or milk-derived product with reduced lactose content.

It is a further object of the embodiments of the invention to provide beta-galactosidases with properties that enable the improved, such as easier, faster, more reliable or less expensive production methods for the lowering of lactose in a product, such as lactose-free or low-lactose products, in particular under acidic conditions.

SUMMARY OF THE INVENTION

The present inventor(s) have identified beta-galactosidases with properties not previously described that enable the production of improved lactose-free or low-lactose products as well as enabling improved production methods for such lactose-free or low-lactose products. In particular, these beta-galactosidases have been shown to be very stable with relatively high activity at low pH values. This enables the use of beta-galactosidases at specific pH values and temperatures that were not known to be possible.

The present invention is based on the recognition that an acid lactase (i.e. a peptide exhibiting beta-galactosidase enzyme activity with a pH optimum below pH 6.7 or below pH 5.5) has several advantages when used in a process for producing an acidified milk product, e.g. a fermented milk product, such as yogurt, subjected to heat treatment after fermentation and suitable for storage at ambient temperature. Such a product is also referred to as a post-pasteurized yogurt.

Firstly, an acid lactase has an activity optimum below pH 6.7 such as below pH 5.5 and typically between pH 3.5 to pH 4.5 and hence it has an optimum activity at the typical pH of a fermented milk product. Thus, the lactase has optimum activity both at the end of the fermentation and during storage of the fermented milk product, heat treated or not, which allows a reduction in the amount of lactase needed to remove lactose from acidified milk product to produce a lactose-free product as compared to a lactase having an activity optimum at a neutral pH.

Secondly, when a lactase is added at the start of fermentation in order to produce a lactose-free product the lactase will impact the fermentation process because the lactose concentration will be reduced as compared to the situation where no lactase is present, and such impact often involves a number of undesired effects. Thus, when a lactase is added at the start of the fermentation, a number of fermentation characteristics may be changed, such as the pH profile, the fermentation time and rate, the carbohydrate metabolism of the lactic acid bacteria, the carbohydrate composition of the fermentation broth and the end pH. Thus, the basic characteristics of the fermentation process are changed and it is usually necessary to re-adjust the operation of the fermentation process when using lactases of the prior art.

This effect of adding a lactase at the start of the fermentation is particularly strong when a lactase with an activity optimum at a neutral pH is used, since the lactase will reduce the level of lactose strongly at the start of the fermentation before any significant drop in pH has occurred. The present invention is based on the further recognition that an acid lactase having an activity optimum at a low pH will cause the major part of the reduction of lactose at the end of the fermentation, and hence the undesired effects of subjecting lactose to lactase conversion will be minimized.

Thirdly, in a process for producing a heat-treated fermented milk product, wherein it is desired that enzymatic removal of lactose takes place during storage after heat-treatment, up to now the only option available has been to add the lactase after the heat-treatment, because lactases are heat labile. Addition of lactase after the heat-treatment requires an additional specialized process step and equipment for sterile addition of the lactase to the heat-treated fermented milk product. However, the present invention is based on the further recognition that an acid lactase is heat-resistant, which in a process comprising a heat treatment after fermentation will allow the lactase to be added to the process before the heat treatment without any need for sterilization of the lactase composition.

Fourthly, the present invention is based on the recognition that the fact that an acid lactase is resistant to both heat and acid conditions provides a possibility of using the lactase for any type of process for producing an acidified milk product and adding the lactase in any step of any such process, including at the start of fermentation and both before and after heat treatment of the acidified milk product. Thus, the present invention has provided full flexibility in use. Thus, for any existing process and plant for producing an acidified milk product, it is possible to freely select in which step to add the lactase without modifying the process and so as to optimize the process with respect to lactose removal. Likewise, the full flexibility in use makes it possible to freely select which acid lactase to use so as to optimize the process with respect to lactose removal.

Hence, the present invention relates to a bacterial peptide exhibiting beta-galactosidase enzyme activity which has an activity optimum at a pH of below pH 6.7 such as e.g. between pH 3 and pH 5 when measured at 37° C. and optionally having an amino acid sequence represented by any one of the following sequences SEQ ID NO: 1, 2, 3, 4, 5, 6, 7, 8, 9, 10, 11, 12, 13, 14, 15, 16, 17, 18, 19 and/or 20 or enzymatically active fragments thereof, or an amino acid sequence represented by any one of the following sequences SEQ ID NO: 1, 2, 3, 4, 5, 6, 7, 8, 9, 10, 11, 12, 13, 14, 15, 16, 17, 18, 19 or 20 having not more than 1, 2, 3, 4, 5, 6, 7, 8, 9, 10, 11, 12, 13, 14, 15, 16, 17, 18, 19, 20, 21, or 22 amino acid substitutions, additions or deletions.

In a related aspect, the present invention relates to a bacterial peptide exhibiting beta-galactosidase enzyme activity which has an activity optimum at a pH of below pH 5.5 such as e.g. between pH 3 and pH 5 when measured at 37° C. An optionally having an amino acid sequence represented by SEQ ID NO:1, 2, 3, 5, 6, 7, 11, 12 and/or 14 or enzymatically active fragments thereof, or an amino acid sequence represented by SEQ ID NO:1, 2, 3, 5, 6, 7, 11, 12 and/or 14 having not more than 1, 2, 3, 4, 5, 6, 7, 8, 9, 10, 11, 12, 13, 14, 15, 16, 17, 18, 19, 20, 21, or 22 amino acid substitutions, additions or deletions.

In an aspect related hereto the invention relates to peptides which are characterized as a GH42 type enzyme and has a pH optimum below pH 6.7 such as pH 5.5 and optionally selected from a list consisting of SEQ ID NO: 1, 2, 3, 4, 7, 8, 9, 10, 11, 12, 13, 14, 15, 16 and 18 or enzymatically active fragments thereof, or an amino acid sequence represented by SEQ ID NO: 1, 2, 3, 4, 7, 8, 9, 10, 11, 12, 13, 14, 15, 16 and 18 having not more than 1, 2, 3, 4, 5, 6, 7, 8, 9, 10, 11, 12, 13, 14, 15, 16, 17, 18, 19, 20, 21, or 22 amino acid substitutions, additions or deletions.

Yet a related aspect of the invention relates to a bacterial peptide according to any of the aspects above, which peptide has an amino acid sequence represented by any one of SEQ ID NO:1-20 or a sequence with at least 80% sequence identity to any one of said sequences; or a host cell expressing any one of said peptides, for producing a dairy product or dairy derived product with a reduced lactose content.

The peptide of the invention may be derived preferably be from a lactic acid bacterium such as e.g. a bacterium of the *Lactococcus, Lactobacillus, Streptococcus* genuses.

Preferably, the beta-galactosidase enzyme activity of the peptide of the invention is determined by diluting the lactase in buffer (50 mM $NaH_2PO_4$ buffer pH 6.7 containing 100 μM of $MgSO_4$) and adding the beta-galactosidase enzyme (140 mM of lactose prepared in 100 mM sodium-citrate buffer of pH 4.5, containing 100 μM of $MgSO_4$) to a reaction mixture which is prepared by mixing 13 μL of diluted enzyme to 37 μL of lactose solution and incubating for 10 min at 37° C.

Accordingly, the present invention also related to a process for producing an acidified milk product comprising the steps of:
- a) providing a milk base, and
- b) converting the milk base into an acidified milk product, which has a pH of between 3.0 and 5.0, and
- c) adding before, during or after any of steps a) to b) a bacterial peptide exhibiting beta-galactosidase enzyme activity, which has an activity optimum at a pH below 6.7 when measured at 37° C., preferably between 1.0 and 6.0 when measured at 37° C., more preferably below 5.5 when measured at 37° C., even more preferably between pH 3 and pH 5 when measured at 37° C.

Or alternatively a process for producing an acidified milk product comprising the steps of:
- a) providing a milk base, and
- b) converting the milk base into an acidified milk product, which has a pH of between 3.0 and 5.0, and
- c) adding before, during or after any of steps a) to b) a bacterial peptide as herein disclosed.

The process of present invention may further comprise the step of d) subjecting the acidified milk product to a heat treatment so as to reduce the level of bacteria to no more than 1×10exp02 CFU per g to obtain a heat treated acidified milk product and/or the step of e) storing the acidified milk product obtained in step b) or the heat-treated acidified milk product obtained in step c) at a temperature of at least 20° C. for at least 1 day.

The milk base used in present invention may be converted into an acidified product by addition of a chemical acidifier or converted into an acidified product by fermentation with a lactic acid bacterium starter culture. The bacterial peptide exhibiting beta-galactosidase enzyme activity may preferably be added in step b) or alternatively between step b) and c) and/or between step c) and d).

In yet a preferred aspect the present invention relates to a process where the acidified milk product containing the bacterial peptide exhibiting beta-galactosidase enzyme activity may be stored at a temperature of at least 20° C. or where the acidified milk product obtained in step b) or the heat-treated acidified milk product obtained in step d) is stored at a temperature of at least 20° C. for at least 3 days.

Accordingly, the present invention also relates to an acidified milk product wherein the product contains a bacterial peptide exhibiting beta-galactosidase enzyme activity, which has an activity optimum at a pH below 6.7 when measured at 37° C., preferably below 5.5 when measured at 37° C., more preferably between 1.0 and 5.0, even more preferably between pH 3 and pH 5 when measured at 37° C.

An acidified milk product, which has a pH of between 3.0 and 5.0, wherein the product contains a bacterial peptide according to present invention is encompassed herein.

Further, the present invention relates to an acidified milk product, which has a pH of between 3.0 and 5.0, wherein the product contains a bacterial peptide exhibiting beta-galactosidase enzyme activity which has an activity optimum at a pH of between 1.0 and 5.5 as well as the use of a lactase in a process for producing an acidified milk product from a milk base to convert at least part of the lactose present in the milk base to glucose and galactose, wherein the lactase is an acid lactase, which has an activity optimum at a pH below 6.7 when measured at 37° C., preferably below 5.5 when measured at 37° C., more preferably between 1.0 and 5.0, even more preferably between pH 3 and pH 5 when measured at 37° C.

Encompassed as an aspect of present invention is the use of a lactase in a process for producing an acidified milk product from a milk base to convert at least part of the lactose present in the milk base to glucose and galactose, wherein the lactase is an acid lactase according to the invention.

LEGENDS TO THE FIGURE

FIG. 1. The activity ratio between selected pH values (pH 6.7, pH 5.5 and pH 4.5 measured at 37° C.

DETAILED DISCLOSURE OF THE INVENTION

The present inventors have found that certain peptides and multimeric peptides exhibiting beta-galactosidase enzyme activity are surprisingly stable at many different physical conditions giving a relatively high activity outside of the ranges normally seen to be optimal for this class of enzymes.

The acid lactase of the present invention is defined as a lactase, which has an activity optimum below pH 6.7 such as below pH 5.5.

In a preferred embodiment the measurement is done according to the following protocol which is further detailed in the Examples herein: The lactases, e.g. obtained as cell free extracts are diluted up to 40× in buffer A (50 mM NaH$_2$PO$_4$ buffer pH 6.7 containing 100 μM of MgSO$_4$). In a separate reaction, the diluted enzyme is incubated with lactose solution prepared in buffer F (140 mM of lactose prepared in 100 mM sodium-citrate buffer of pH 4.5, pH 5.5 and 6.7 respectively, containing 100 μM of MgSO$_4$). The reaction mixture is prepared by mixing 13 μL of diluted enzyme and 37 μL of lactose solution in a PCR tube. The reaction mixture is incubated in a DNA thermal cycler using the following incubating parameters (reaction time; 10 min at 37° C., enzyme inactivation; 10 min at 95° C., storage; 4° C.). The reaction mixtures were stored at −20° C. until further use. The maximum absorbance value for each lactase was used to determine μmol of glucose formed per minute, described as 1 Unit of Activity with Lactose at pH 4.5, 5.5 and 6.7 at 37° C. The high activity at relatively low pH at 37° C. is relevant for the lactose hydrolysis in the fermented milk applications and acidic whey lactose hydrolysis.

In terms of applicability for fermented products it is highly advantageous that the enzymes as described herein have a high beta-galactosidase enzymatic activity at a relatively broad pH range of such as down to 4.5, or down to 4.0, or down to 3.5, or even down to pH 3.

Definitions

The term "bacterial peptide" or a as used herein and in the context of the present invention is to be understood as a peptide of bacterial origin or a peptide derived from a bacterium. In the context of present invention, preferred bacteria comprise lactic acid bacteria such as members of the *Lactobacillus, Lactococcus* or *Bifidobacterium* genuses.

The term "activity optimum at a pH below 6.7 when measured at 37° C." as used herein and in the context of the present invention means that a given enzyme is most active at a pH below 6.7, such as e.g. between pH 3 and pH 5, when said activity is measured at 37° C. As such, the most favorable pH value at which the enzyme is most active is a pH below 6.7.

The term "activity optimum at a pH below 5.5 when measured at 37° C." as used herein and in the context of the present invention means that a given enzyme is most active at a pH below 5.5, such as e.g. between pH 3 and pH 5, when said activity is measured at 37° C. As such, the most favorable pH value at which the enzyme is most active is a pH below 5.5.

The term "activity optimum at a pH between pH 3 and pH 5 when measured at 37° C." as used herein and in the context of the present invention means that a given enzyme is most active at a pH between pH 3 and pH 5, when said activity is measured at 37° C. As such, the most favorable pH value at which the enzyme is most active is a pH between pH 3 and pH 5.

The term "milk", as used herein and in the context of the present invention, is to be understood as the lacteal secretion obtained by milking any mammal, such as cow, sheep, goats, buffalo or camel.

The term "composition containing lactose" as used herein refers to any composition, such as any liquid that contain lactose in significant measurable degree, such as a lactose content higher than 0.002% (0.002 g/100 ml). Encompassed within this term are milk and milk-based substrates.

The term "composition containing reduced lactose content" as used herein refers to any composition, such as any liquid that has a lactose content lower than 0.002% (0.002 g/100 ml). Encompassed within this term are milk and milk-based substrates with a lactose content lower than 0.002% (0.002 g/100 ml).

The term "dairy product or dairy derived product with a reduced lactose content" as used herein refers to a dairy product or dairy derived product produced with a lactose content lower than 0.002% (0.002 g/100 ml).

The term "milk-based substrate" or "milk-base", in the context of the present invention, may be any raw and/or processed milk material. Useful milk-based substrates include, but are not limited to solutions/suspensions of any milk or milk like products comprising lactose, such as whole or low fat milk, skim milk, buttermilk, low-lactose milk, reconstituted milk powder, condensed milk, solutions of dried milk, UHT milk, whey, whey permeate, acid whey, cream, fermented milk products, such as yoghurt, cheese, dietary supplement and probiotic dietary products. Typically, the term milk-based substrate refers to a raw or processed milk material that is processed further in order to produce a dairy product.

The term "pasteurization" as used herein refers to the process of reducing or eliminating the presence of live organisms, such as microorganisms in a milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

The term "dairy product" as used herein may be any food product wherein one of the major constituents is milk-based. Usually the major constituent is milk-based and in some embodiments, the major constituent is a milk-based substrate which has been treated with an enzyme having beta-galactosidase activity according to a method of the present invention.

A dairy product according to the invention may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavored milk drink.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavoring agents, microbial cultures such as probiotic cultures, salts, sweeteners, sugars, acids, fruit, fruit prep, fruit juices, or any other component known in the art as a component of, or additive to, a dairy product.

The terms "fermented dairy product" or "fermented milk product" as used herein is to be understood as any dairy product wherein any type of fermentation forms part of the production process. Examples of fermented dairy products are products like yoghurt, buttermilk, creme fraiche, quark and fromage frais of cheese. A fermented dairy product may be produced by or include steps of any method known in the art.

The term "fermentation" as used herein refers to the conversion of carbohydrates into alcohols or acids through the action of a microorganism. In some embodiments fermentation according to the present invention comprises the conversion of lactose to lactic acid. In the context of the present invention, "microorganism" may include any bacterium or fungus being able to ferment the milk substrate.

The term "peptide exhibiting beta-galactosidase enzyme activity" as used herein refers to any peptide, which has enzymatic activity to catalyze the hydrolysis of the disaccharide lactose into its component monosaccharides glucose and galactose. This peptide may also be referred to as a lactase or simply a beta-galactosidase (EC: 3.2.1.23).

The terms "peptide" and "oligopeptide" as used in the context of this present application are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All peptide and polypeptide formulas or sequences herein are written from left to right and in the direction from amino terminus to carboxy terminus. "Proteins" as used herein refers to peptide sequences as they are produced by some host organism and may include posttranslational modification, such as added glycans.

The terms "amino acid" or "amino acid sequence," as used herein, refer to an oligopeptide, peptide, polypeptide, or protein sequence, or a fragment of any of these, and to naturally occurring or synthetic molecules. In this context, "fragment" refers to fragments of a peptide exhibiting beta-galactosidase enzyme activity, which retain some enzymatic activity. Where "amino acid sequence" is recited herein to refer to an amino acid sequence of a naturally occurring protein molecule, "amino acid sequence" and like terms are not meant to limit the amino acid sequence to the complete native amino acid sequence associated with the recited peptide molecule.

Exemplary peptides of the invention also include fragments of at least about 200, 250, 300, 350, 400, 450, 500, 550, 600, 650, 700, 750, 800, 900, 1000, 1100 or more residues in length, or over the full length of an enzyme. Accordingly, a "peptide fragment" or "enzymatically active fragment" of the invention are fragments that retain at least some functional enzymatic activity. Typically, a peptide fragment of the invention will still contain the functional catalytic domain or other essential active sites of the peptide exhibiting beta-galactosidase enzyme activity. Other domains may be deleted.

Unless otherwise stated the term "Sequence identity" for amino acids as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences.

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, gap extension etc., are used.

A peptide with a specific amino acid sequence as described herein may vary from a reference peptide sequence by any of amino acid substitutions, additions/insertions, or deletions.

Some embodiments according to the present invention refers to the use of a peptide with an amino acid sequence represented by SEQ ID NO:1-20 or a sequence with at least 80% sequence identity to any one of said sequences. In some embodiments this sequence identity may be at least about 81%, 82%, 83%, 84%, 85%, 86%, 87%, 88%, 89%, 90%, 91%, 92%, 93%, 94%, 95%, 96%, 97%, 98%, or 99%, such as a peptide with not more than 1, 2, 3, 4, 5, 6, 7, 8, 9, 10, 11, 12, 13, 14, 15, 16, 17, 18, 19, 20, 21, or 22 amino acid substitutions, additions or deletions as compared to any one reference amino acid sequence represented by SEQ ID NO:1-20. The invention also features biologically active fragments of the peptides according to the invention. Biologically active fragments of a peptide of the invention include peptides comprising amino acid sequences sufficiently identical to or derived from the amino acid sequence of peptide of the invention which include fewer amino acids than the full-length protein but which exhibit a substantial part of the biological activity of the corresponding full-length peptide. Typically, biologically active fragments comprise a domain or motif with at least one activity of a variant protein of the invention. A biologically active fragment of a peptide of the invention can be a peptide which is, for example, 200, 300, 400, 500, 600, 700, 800, 900, 1000, 1100 or more amino acids in length.

The term "host cell", as used herein, includes any cell type which is susceptible to transformation, transfection, transduction, and the like with a nucleic acid construct or expression vector comprising a polynucleotide encoding the peptides of the present invention. A host cell may be the cell type, where a specific enzyme is derived from or it may be an alternative cell type susceptible to the production of a specific enzyme. The term includes both wild type and attenuated strains.

Suitable host cell may be any bacteria including lactic acid bacteria within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Also included are lactic acid producing bacteria belonging to the group of anaerobic bacteria, bifidobacteria, i.e. *Bifidobacterium* spp., which are frequently used as food cultures alone or in combination with lactic acid bacteria. Also included within this definition are *Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis biovar. diacetylactis, Lactobacillus casei* subsp. *casei* and *Lactobacillus paracasei* subsp. *Paracasei* and thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*. Other specific bacteria within this definition includes bacteria of the family Bifidobacteriaceae, such as from the genus *Bifidobacterium*, such as from a strain of *Bifidobacterium animalis* or *Bifidobacterium longum, Bifidobacterium adolescentis, Bifidobacterium bifodum, Bifidobacterium breve, Bifidobacterium catenulatum, Bifidobacterium infantus* or from the genus *Lactobacillus*, such as *L. sakei, L. amylovorus, L. delbrueckii* subsp. *Lactis*, and *L. helveticus*.

Also included within this definition of host cells include strain of *Agaricus*, e.g. *A. bisporus; Ascovaginospora;*

*Aspergillus*, e.g. *A. niger, A. awamori, A. foetidus, A. japonicus, A. oryzae; Candida; Chaetomium; Chaetotomastia; Dictyostelium*, e.g. *D. discoideum; Kluveromyces*, e.g. *K. fragilis, K. lactis; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer; Sclerotinia*, e.g. *S. libertiana; Torula; Torulopsis; Trichophyton*, e.g. *T. rubrum; Whetzelinia*, e.g. *W. sclerotiorum; Bacillus*, e.g. *B. coagulans, B. circulans, B. megaterium, B. novalis, B. subtilis, B. pumilus, B. stearothermophilus, B. thuringiensis; Bifidobacterium*, e.g. *B. Iongum, B. bifidum, B. animalis; Chryseobacterium; Citrobacter*, e.g. *C. freundii; Clostridium*, e.g. *C. perfringens; Diplodia*, e.g. *D. gossypina; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Miriococcum; Myrothesium; Mucor; Neurospora*, e.g. *N. crassa; Proteus*, e.g. *P. vulgaris; Providencia*, e.g. *P. stuartii; Pycnoporus*, e.g. *Pycnoporus cinnabarinus, Pycnoporus sanguineus; Ruminococcus*, e.g. *R. torques; Salmonella*, e.g. *S. typhimurium; Serratia*, e.g. *S. liquefasciens, S. marcescens; Shigella*, e.g. *S. flexneri; Streptomyces*, e.g. *S. antibioticus, S. castaneoglobisporus, S. violeceoruber; Trametes; Trichoderma*, e.g. *T. reesei, T. viride; Corynebacteria; Pichia; Saccharomyces; Hansenula; Yersinia*, e.g. *Y. enterocolitica.*

SEQUENCES

TABLE 1

| The gene numbers with corresponding sequence identification number. | | |
| --- | --- | --- |
| Gene number | Sequence identity number | Species name |
| G1 | SEQ ID No 1 | *Bifidobacterium adolescentis* |
| G3 | SEQ ID No 2 | *Bifidobacterium adolescentis* |
| G32 | SEQ ID No 3 | *Bifidobacterium adolescentis* |
| G39 | SEQ ID No 4 | *Lactobacillus amylovorus* |
| G40 | SEQ ID No 5 (domain a) SEQ ID No 6 (domain b) | *Lactobacillus amylovorus* |
| G46 | SEQ ID No 7 | *Bifidobacterium bifidum* |
| G60 | SEQ ID No 8 | *Lactobacillus brevis* |
| G62 | SEQ ID No 9 | *Bifidobacterium catenulatum* |
| G67 | SEQ ID No 10 | *Bifidobacterium pseudocatenulatum* |
| G137 | SEQ ID No 11 | *Lactobacillus gasseri* |
| G140 | SEQ ID No 12 | *Lactobacillus helvaticus* |
| G162 | SEQ ID No 13 | *Bifidobacterium longum* |
| G166 | SEQ ID No 14 | *Bifidobacterium longum* |
| G169 | SEQ ID No 15 | *Bifidobacterium longum* |
| G217 | SEQ ID No 16 | *Lactobacillus reuteri* |
| G262 | SEQ ID No 17 | *Lactobacillus delbreuckii lactis* |
| G311 | SEQ ID No 18 | *Bifidobacterium angulatum* |
| G330 | SEQ ID No 19 (domain a) SEQ ID No 20 (domain b) | *Lactobacillus fermentum* |
| G500 | SEQ ID No 21 | *Kluyveromyces lactis* |
| G600 | SEQ ID No 22 | *Bifidobacterium bifidum* |

SEQ ID No 1: G1

MRRNFEWPKLLTADGRGIAFGGDYNPDQWSEDIWDDDIRLMKQAGVNTVALAIFSWDRIQPTEDR

WDFGWLDRIIDKLGNAGIAVDLASATATAPLWLYESHPEVLPRDKYGHPVNAGSRQSWSPTSPVFK

EYALTLCRKLAERYGTNPYVTAWHMGNEYGWNNREDYSDNALDAFRAWCRRKYGTIGALNQAWG

TTFWGQEMNGFDEVLIPRFMGADSMVNPGQKLDFERFGNDMLLDFYKAERDAIAEICPDKPFTTNF

MVSTDQCCMDYAAWAEEVNFVSNDHYFHEGESHLDELACSDALMDSLALGKPWYVMEHSTSAVQ

WKPLNTRKRKGETVRDSLAHVAMGADAINFFQWRASAFGAESFHSAMVPHAGEDTKLFRQVCELG

ASLHTLADAGVQGTELAHSDTAILFSAESEWATRSQTLPSMKLNHWHDVRDWYRAFLNAGSRADI

VPLAYDWSSYKTVVLPTVLILSAADTQRLADFAAAGGRVVVGYATGLIDEHFHTWLGGYPGAGDGL

LRSMLGVRGEEFNILGAEAEGEPGEIRLSSADDSAALDGTTTRLWQNDVNVTGEHAQVLATYAGEE

ADEWELDGTAAVTRNPYGSGEAYFVGCDLDVADLTKLVRAYLAAPSQDNADVLHTVRESADATFDF

YLPRGKETVELQGIEGEPVILFQTERGKKPGSYTVHRNGVLVVRR

SEQ ID No 2: G3
MNQRREHRWPRPLEGRRARIWYGGDYNPDQWPEEVWDEDVRLMVKAGVNLVSVGIFSWAKIEPR

EDMYDFGWLDRIIDKLGKAGIAVDLASATASPPMWLTQAHPEVLWKDYRGDVCQPGARQHWRPT

SPVFCEYALKLCRAMAEHYKDNPYVVAWHVGNEYGCHNRFDYSEDAERAFQDWCEERYGTIEAVN

DAWGTAFWAQHLNDFSEIVPPRFIGDGNFMNPGKLLDFKRFSSDALKSFYVAERDALAEITPEKPLT

TNFMVSAGGSVLDYDDWGGEVDFVSNDHYFIPGEAHLDELAFSASLVDGISRKDPWFLMEHSTSA

VNWRPINYRKEPGQLVRDSLAHVAMGADAVCYFQWRQSRSGAEKFHSAMLPHAGEDSQTFRDVC

ELGRDLGTLADEGLLGTKLAKSSVAIVFDYESEWASEHTATPTQNVHHIDEPLAWFRALADVGVTA

DVVPIRSNWDEYDVAILPSVYILSEENTRRVRDYVANGGKLIATYYTGISDERDHVWLGGYPGSIRD

VVGVRIEEFAPMGSDWPGVPDHLDLDNGAVAHDIVDVIGSIGKDAKVLASFKDDPWTGMDGRPAI

VSNPYGEGRSVYVGARLGRDGIARSLPMILETLGVEVKDSSDPDLLRIERVDESTGARFTFLFNRTKE

PVSMLVEGRPVVMSLADCAGATVTINPNGVLVVKQ

SEQ ID No 3: G32
MRRNFEWPKLLTADGRGIAFGGDYNPDQWSEDIWDDDIRLMKQAGVNTVALAIFSWDRIQPTEDR

WDFGWLDRIIDKLGNAGIAVDLASATATAPLWLYESHPEVLPRDKYGHPVNAGSRQSWSPTSPVFK

EYALTLCRKLAERYGTNPYVTAWHMGNEYGWNNREDYSDNALDAFRAWCRRKYGTIGALNQAWG

TTFWGQEMNGFDEVLIPRFMGADSMVNPGQKLDFERFGNDMLLDFYKAERDAIAEICPDKPFTTNF

MVSTDQCCMDYAAWAEEVNFVSNDHYFHEGKSHLNKLACSDALMDSLALGKPWYVMEHSTSAVQ

WKPLNTRKRKGETVRDSLAHVAMGADAINFFQWRASAFGAESFHSAMVPHAGEDTKLFRQVCELG

ASLHTLADAGVQGTELAHSDTAILFSAESEQATRSQTLPSMKLNHWHDVRDWYRAFLDAGSRADI

VPLAYDWSSYKTVVLPTVLILSAADTQRLADFAAAGGRVVIGYATGLIDEHFHTWLGGYPGAGDGLL

RLMLGVRGEEFNILGAEAEGEPSEIRLASADDSVAMDGSTTRLWQNDVNVTGEHAQVLATYAGEEA

DEWELDGTAAVTRNPYGSGEAYFVGCDLDVADLTKLVRAYLAAPSQDNADVLHTVRESADATFDFY

LPRGKETVELQGIEGEPVILFQTERGKKPGSYTVHRNGVLVVRR

SEQ ID No 4: G39
MTKTLSRFLYGGDYNPDQWTEETWPEDIKVFKKVDLNSATINIFSWAVLEPREGVYDFSKLDKIVQE

LSDANFDIVMGTATAAMPAWMFKKYPDIARVDYQGRRHVFGQRHNFCPNSKNYQRLDSELVEKLA

QHYADNSHIVVWHVNNEYGGNCYCGNCQNAFRDWLRNKYKTLGALNKAWNMNVWSHTIYDWD

EIVVPNELGDAWGPESSETIVAGLSIDYLRFQSESLQNLFKMEKAVIKKYDPETPVTTNFHSLPNKMI

DYQKWAKDQDIISYDSYPTYDAPAYKPAFLYDLMRSLKHQPFMLMESAPSQVNWQSYSPLKRPGQ

MAATELQAVAHGADTVQFFQLKQAVGGSEKFHSAIIAHSQRTDTRAFCELADLGQKLKEAGPTILGS

KTKAKVAIVFDWSNFWSYEYVDGITQDLNYVDSILDYYRQFYERNIPTDIIGVDDDFSNYDLVVAPV

LYMVKAGLAEKINSYVEKGGHLVTTYMSGMVDSTDNVYLGGYPGPLKDVTGIWVEESDAMVPGQK

-continued

VRVTMDGKEYETNLMCDLIHPNKAKVLASYADEFYTGTAAITENDYGKGKAWYVGTKLGHQGLTQL

FNHIVLETGVESLVCDSHKLEVTKRVTADGKELYFVLNMSNEERELPNKFADYEDILTGEKAKSSMK

GWDVQVLTK

SEQ ID No 5 (G40 domain a)
MKANIKWLDDPEVFRINQLPAHSDHPFYKDYREWQNHSSSFKQSLNGAWQFHFSKDPQSRPIDFY

KRSFDSSSFDTIPVPSEIELNGYAQNQYTNILYPWESKIYRKPAYTLGRGIKDGDFSQGKDNTVGSY

LKHFDLNPALAGHDIHIQFEGVERAMYVYLNGHFIGYAEDSFTPSEFDLTPYIQAKDNILAVEVFKHS

TASWLEDQDMFRFSGIFRSVELLALPRTHLMDLDIKPTVVNDYHDGVFNAKLHFMGKTSGNVHVLI

EDIDGKTLLNKKLPLKSTVEIENETFANVHLWDNHDPYLYQLIIEVHDQDGKLVELIPYQFGFRKIEIT

KDHVVLLNGKRLIINGVNRHEWDAKRGRSITLADMKQDIATFKHNNINAVRTCHYPNQIPWYYLCD

QNGIYMMAENNLESHGTWQKLGQVEATSNVPGSIPEWREVVVDRARSNYETFKNHTAILFWSLGN

ESYAGSNIAAMNKLYKDHDSSRLTHYEGVFHAPEFKKEISDLESCMYLPPKEAEEYLQNPKKPLVECE

YMHDMGTPDGGMGSYIKLIDKYPQYMGGFIWDFIDQALLVHDPVSGQDVLRYGGDFDDRHSDYEF

SGDGLMFADRTPKPAMQEVRYYYGLHK

SEQ ID No. 6 (G40 domain b)
MAYTNNLHVVYGEASLGVNGQDFAYLFSYERGGLESLKIKDKEWLYRTPTPTFWRATTDNDRGSGF

NQKAAQWLGADMFTKCVGIHVQVDDHRFDELPVAPINNQFSNQEFAHEVKVAFDYETLTTPATKVK

IIYNINDFGHMTITMHYFGKKGLPPLPVIGMRFIMPTKAKSFDYTGLSGETYPDRMAGAERGTFHIDG

LPVTKYLVPQENGMHMQTNELVITRNSTQNNADKDGDFSLKITQTKQPFNFSLLPYTAEELENATHI

EELPLARRSVLVIAGAVRGVGGIDSWGSDVEEQYHIDPEQDHEFSFTLN

SEQ ID No 7: G46
MERNMSKRRKHSWPQPLKGAESRLWYGGDYNPDQWPEEVWDDDIRLMKKAGVNLVSVGIFSWA

KIEPEEGKYDFDWLDRAIDKLGKAGIAVDLASATASPPMWLTQAHPEVLWKDERGDTVWPGAREH

WRPTSPVFREYALNLCRRMAEHYKGNPYVVAWHVSNEYGCHNRFDYSDDAMRAFQKWCKKRYKTI

DAVNEAWGTAFWAQHMNDFSEIIPPRYIGDGNFMNPGKLLDYKRFSSDALKELYIAERDVLESITPG

LPLTTNFMVSAGGSMLDYDDWGAEVDFVSNDHYFTPGEAHFDEVAYAASLMDGISRKEPWFQMEH

STSAVNWRPINYRAEPGSVVRDSLAQVAMGADAICYFQWRQSKAGAEKWHSSMVPHAGEDSQIF

RDVCELGADLGRLSDEGLMGTKTVKSKVAVVFDYESQWATEYTANPTQQVDHWTEPLDWFRALAD

NGITADVVPVRSDWDSYEIAVLPCVYLLSEETSRRVREFVANGGKLFVTYYTGLSDENDHIWLGGYP

GSIRDVVGVRVEEFAPMGNDMPGALDHLDLDNGTVAHDFADVITSTADTSTVLASYKAERWTGMN

EVPAIVANGYGDGRTVYVGCRLGRQGLAKSLPAMLGSMGLSDLAGDGRVLRVERADAAAASHFEF

VFNRTHEPVTVDVEGEAIAASLAHVDDGRATIDPTGVVVLRR

SEQ ID No 8: G60
MKRELKSKVFLHGGDYNPEQWLGEPEIINEDFALFKNAAINTVTVGIFSWAKLEPEEGKYDFAWLDD

IFDRVEKMNGYVILATPSGARPAWLARKYPEVLRTDFNNQKRGFGGRHNHCLTSPIYRKKVREINTK

LAEHFGKRPSLILWHISNEYSGECYCDLCQQAFRDWLKKKYRTLERLNHSWWNTFWSHTFSDWN

QIHAPSPLSEMGNKGMNLDWKRFVSDQAISFIDNEVEPLRKITSEIPVTTNMMAGNPLMDPFTGYN

YQEMAKHLDVISWDSYPLWGNDFQSTEKLGQNVGLIHDFFRSLKHQNFMIMENTPSRVNWADIDR

AKRPGMHQLASLQDIAHSSDSVLYFQLRASRGSAEMFHGAVIEHRHPEKTRVFHDVKDVGHDLEKL

ESIYSTSYTKAKVGIVYDYNNIWALEDAEGYSKDKKIWQTIQSQYQYFYQNDIPVDFVSPNDNFTQY

KLLIDPMHFLMTKEYMDKLESFVKKCGYVVGTYISGVVDENGLAYMNEWPKQLQSIYGIEPLETDSL

YPKQSNSIEFAGHRYQAYDFCETIFKHDAKVLAKYTTDFYSGTPALTAHKCGEGKGYYIACRTDTDFL

SAIYGQIVKELDLLPNLPIKKETTKISLQVRENDDEKYLFVQNFSHEQQSILLKQKMKEMLSDEFEEN

KVIVKPYGTKIYQMN

SEQ ID No 9: G62
MTQRRSYRWPQPLAGQQARIWYGGDYNPDQWPEEVWDDDVRLMKKAGVNLVSVGIFSWAKIET

SEGVYDFDWLDRIIDKLGEAGIAVDLASATASPPMWLTQAHPEVLWKDYRGDVCQPGARQHWRPT

SPVFREYALKLCRAMAEHYKGNPYVVAWHVSNEYGCHNRFDYSEDAERAFRKWCEERYGTIDAVN

DAWGTAFWAQRMNDFTEIVPPRFIGDGNFMNPGKLLDFKRFSSDALKAFYVAERDALAEITPDLPLT

TNFMVSAAGSVLDYDDWGREVDFVSNDHYFIPGEAHLDELAFSASLVDGIARKDPWFLMEHSTSA

VNWRPVNYRKEPGQLVRDSLAHVAMGADAVCYFQWRQSKAGAEKFHSAMVPHTGEDSAVFRDVC

ELGADLNTLADNGLLGTKLAKSKVAVVFDYESEWATEHTATPTQKVHHVDEPLQWFRALADHGVTA

DVVPVSSNWDEYEVVVLPSVYILSEETTRRVRDYVVNGGRLIVTYYTGLSDEKDHVWLGGYPGSIR

DVVGVRVEEFMPMGDDFPGVPDCLGLSNGAVAHDIADVIGSVDGTATVLETFRDDPWTGMDGAPA

IVANTFGEGRSVYVGARLGRDGIAKSLPEIFESLGMAETGENDSRVLRVEREGSDGSRFVFSFNRTH

EAVQIPFEGKIVVSSFAEVSGENVSIKPNGVIVTKQ

SEQ ID No 10: G67
MTQRRAYRWPQPLAGQQARIWYGGDYNPDQWPEEVWDDDVRLMKKAGVNLVSVGIFSWAKIET

SEGVYDFDWLDRIINKLGEAGIAVDLASATASPPMWLTQAHPEVLWKDYRGDVCQPGARQHWRPT

SPVFREYALKLCRAMAEHYKGNPYVVAWHVSNEYGCHNRFDYSEDAERAFRKWCEERYGTIDAVN

DAWGTAFWAQRMNDFTEIVPPRFIGDGNFMNPGKLLDFKRFSSDALKAFYVAERDALAEITPDLPLT

TNFMVSAAGSVLDYDDWGREVDFVSNDHYFIPGEAHLDELAFSASLVDGIARKDPWFLMEHSTSA

VNWRPVNYRKEPGQLVRDSLAHVAMGADAVCYFQWRQSKAGAEKFHSAMVPHAGEDSAVFRDVC

ELGADLNTLADNGLLGTKLAKSKVAVVFDYESEWASEHTATPTQKVHHVDEPLQWFRALADHGVTA

DVVPVRGAWDDYEMVVLPSVYLLSEETTRRVRDYVVGGGRLVVTYYTGISDEKDHVWLGGYPGSIR

DVVGVRVEEFMPMGDDFPGVPDCLGLSNGAVAHDIADVIGSVDGTATVLETFKDDPWTGMDGAPA

IVAHTFGEGRSVYVGARLGRDGIALSLPEILDSLGMAEAGGNDGRVLRVEREGADGSRFVFSFNRT

HETVRVPVEGEVVVSSFAEVSGETISIKPNGVIVTKQ

SEQ ID No 11: G137
MKRILNTNEFLHGGDYNPEQWWDEPDVINQDFALFKQAKINTVTVGIFSWAKLEPEEGNYDFSWL

DSIFDRVEEMNGHVVLATPSGARPAWLAQKYPEVLRTDNLGNKRGFGGRHNHCLTSPIYREKVREI

NTKLAEHFGQRKSLVLWHISNEYSGECYCESCKNAFRDWLKNKYGNLDNLNHAWWNTFWSHTYN

DWSQVNPPSPLGEMGNKGMNLDWKRFITDQTISFIDNEAAPLRKITPNVPVTTNMMAGNPLMDPFA

GFDYQKVAKHLDFISWDSYPAWGNDNQTTAELGRNVGLVHDFFRSLKHQNFLVMENTPSRVNWH

SVDRAKRPGMHELASLQDVARGSQGVLYFQLRASRGSSEMFHGAVIEHLHPEQTRAFKDVTTVGK

DLENIRPIINTNYAKARVAIVFSYDSYWALQDAESYSKDKKIWQTIQKHYRYFYKHDIPVDFVSVED

DFSNYDLLIDPMHFLMSKAYLKKLASYVKNGGRVVGTYISGVVDENDLAYMNEWPKELQDIYGVEP

LETDVLYPGQSNTLNFDGHEYKAHDYCETLINCRGKVLAKYASDFYQDTPAVVEHEYGAGKGYYLAC

RTDYDLLEKFYEKITANLIPEFPVKKFSSNISIQVRENKDQKYYFVQNFSDKSEQIKVDGELEDLLEKK

IDRGEVVLNPFGSKIYYKKGN

SEQ ID No 12: G140
MLEPEEGKYDFSELDKVVKKLSDANFDIVIGTSTAAMPAWMFKKYPDVARVDYQGRRHVFGQRYNF

CPNSKNYQRLAGNLVEELAKHYQNNPNIVVWHVNNEYGGNCYCENCQHEFRKWLKDKYQTLDALN

KAWNMNVWSHTIYDWDEIVVSNELGDAWGPEGSETIVAGLSIDYLRFQSESLQNLFKMEKQIIKKH

-continued

DSEAPVTTNFHSLPNKMIDYQKWAKDQDIISYDSYHTYDAPTYKPAFLYNLMRSLKHQPFMLMESAP

SQVNWQPYSPLKRPGQMAATELQAVAHGADTVQFFQLKQAVGGSEKFHSAVIAHSQRTDTRVFKE

LVDLGHKLKRAGSTILGSTINAKVGIVFDWSNFWSYEYVDGISQDMDYVDSILDYYRQFYERNIPTD

IISVDDDFSKYDLIVAPVLYMVKDGLAEKINNYVECGGNFVTTYMSGMVDSTDNVYLGGYPGPLKNV

TGIWVEESDAVVPGHTTTVSLKGKDYKAGFVCDLIHPEQAKVLAEYSNEFYAGTPAITENKYGQGKA

WYVGTRLDHTGLTQLFNHIVLESNIESLVCDGDKLEVTKRVTQDGQELYFVLNMSNEVRNLPQKFIG

YQDILTDKKASDKLERWGVQVLTK

SEQ ID No 13: G162
MTTHRAFRWPSLLTESGRGIAFGGDYNPDQWPEETLDEDIRLMGEAGVNVVSLAIFSWDKIEPVEG

AFTFEWLDHVIDRLGRAGIAVDLASATAAAPLWLYESHPEVLPVDRYGHTVNAGSRQSWQPTSPVF

KEYALRLCRKLAEHYKDNPYVTAWHMGNEYGWNNRYDYSDNALAAFRTWCEAKYGTIDALNEAW

GTAFWSQHVNSFDEVLLPRHMGGDAMVNPSQQLDYERFGNDMLLDFYKAERDAIEQICPDKPFTT

NFMVSTDQCVMNYAKWADEVDFVSNDHYFHEGESHLDELACSDALMDSLALGKPWYVMEHSTSA

VQWKPLNTRKRAGELMRDSLAHVAMGADAICFFQWRQSKSGAEAFHSAMLPHAGADSKVFRGVC

ELGKALKTLSDAGLQGTELERAGTAILFSAESEWATRSETLPSMKLNHWHDVRDWYRGFLDAGLRA

DVVPLAYDWTGYKTIVLPTVLSLSDEDVLRIADFAKAGGTVIVGYAAGLIDEHFHIGLGGYPGAGNG

LLRDMLGIRSEEFNILGEEAEGEPSEISLSNGLTTRLWQNDVTSVAADTTVLASYAGESAADWELER

TPAITSRPYGNGTAIYVGCDLNRHDIAQLLKALGSRWQELSAQPTESGQTPTYPTTDPRILHTIRRSA

DGSTRFDFYLNRSNQPVAINGVEGDPIIAHRCETDAVGYTLNRNAILIAKTSC

SEQ ID No 14: G166
MERKEFKWPQPLAGNKPRIWYGGDYNPDQWPEEVWDEDVALMQQAGVNLVSVAIFSWAKLEPEE

GVYDFDWLDRVIDKLGKAGIAVDLASGTASPPMWMTQAHPEILWVDYRGDVCQPGARQHWRATS

PVFLDYALSLCRKMAEHYKDNPYVVSWHVSNEYGCHNRFDYSEDAERAFQKWCEKKYGTIDAVND

AWGTAFWAQRMNNFSEIIPPRFIGDGNFMNPGKLLDWKRFSSDALLDFYKAERDALLEIAPKPQTT

NFMVSAGGTGIDYDKWGYDVDFVSNDHYFTPGEAHFDELAYSASLCDGIARKNPWFLMEHSSSAV

NWRPINYRVEPGELVRDSLAHLAMGSDAICYFQWRQSKAGAEKWHSSMVPHAGPDSQIFRDVCEL

GADLNKLADEGLLSTKLVKSKVAVVFDYESQWVTEHTATPTQEVRHWTEPLAWFRALADNGLTAD

VVPVRGSWDEYEAVVLPSLTILSEETTRRVREYVANGGKLFVTYYTGLVDDKDHVWLGGYPGSIRD

VVGVRVEEFAPMGNDFPGAMDHLDLDNGTVAHDFADVITSVADTAHVVASFKADKWTGFDGAPAI

TVNDFGDGKAAYVGARLGREGLAKSLPALLEELGIETSAEDDRGEVLRVERADETGENHFVFLFNRT

HDVAVVDVEGEPLVASLAQVNESERTAAIQPNGVLVVKL

SEQ ID No 15: G169
MTTRRTFRWPSLLTESGRGIAFGGDYNPDQWPEETLDEDIRLMVQAGVNTVALAIFSWDKIEPREG

EFTFEWLDHVIDKLGAASIAVDLASATATAPLWLYERHPEVLPIDRYGHVVNAGSRQSWQPTSPVLK

EYALRLCRKLAEHYKDNPYVTAWHMGNEYGWNNRYDYSDNALAAFRTWCEAKYGTVDALNEAWG

TAFWSQHVNSFDEVLLPRHMGGDSMVNPPQQLDYERFGNDMLLDFYKAERDAIEEICPGKPFTTNF

MVSTDQCTMDYAQWANEVDFVSNDHYFHEGESHLDELACSDALMDSLALGKPWYVMEHSTSAVQ

WKPLNTRKRAGELMRDSLAHVAMGADAINFFQWRQSASGAEAFHSAMVPHAGSDTKLFRGVCEL

GAALKTLSDAGVQDTELKRADTAILFSAESEWATRSETLPSMKLNHWHDVRDWYRGYLDAGARAD

VVPLAYDWSGYQTIVLPTVIALSDEDTRRIADFAENGGTVIVGYATGLIDEHFHIGLGGYPGAGNGLL

-continued

RDMLGIRSEEFNILGEEAEDEPAEIGLSNGLTTRLWQNDVTSVAPDTRVLATYVGTAAADWELDGV

PAITSHPHGQGAAIYVGCDLGRHDITHLLKELNTTAPSDERAPDQRPGGGEINAATTTAAATTHDPR

ILHTIRQSSDGTIRFDFYLNRSKQPVAVNGVEGDPIIAHRCETDAVGYTLNRNAILIAKTSC

SEQ ID No 16: G217
MMKKELPRFLYGGDYNPEQWPEETWDEDIKVFKQADINSATINVFSWALLEPQEGKYDFTKLDKIIK

ELTVADFDIVLATSTAAMPAWMFKKYPDVARVDYQGRRHVFGARHNFCPSSKNYRRLAKNLVEQLA

KRYGDNPHIVAWHVNNEYGGNCYCEECQTEFQQWLKARYQTLDNLNHAWNMNVWSHTIHDWNE

IVVPNELGDAWGPEGSETIVAGLSIDYLRFQSAQMLDLFKMEKQIIEKYDPTTLVTTNFHSLPNKMID

YQQWASAQDIISYDSYPAYDAPIYQPAFLYDLMRSLKHQPFMLMESTPSQVNWQPYSPLKRPGQMA

ATELQAVAHGADTVQFFQLKQALGGSEKFHGAVISHANRTDTRVFKEVAKLGHDLRKVGPVIKDSQ

TKARVALIFDWSNFWSFEYVDGITQDLKYVPIILDYYRQFYELNIPTDVISVDDDFRQYDLVVAPVLY

MVKGGLGKKITDYVANGGNFITSFMSGMVNESDNIYPGGYPGPLKDVMGLWVEESDAILPNKDVK

LTMTTGDELTGYLIADLIRLNGAHVLAEYASEFYAGTPAVTENTYSKGKAWYVGSRLDHASLRKIIMH

IVDDVHLSALVKEPTELEITKRQNSAGQDIYFVLNMGKGKQPLPVEFQKGYRDLLTGDSPETMLDS

WDVEILVQE

SEQ ID NO 17: G262
MSNKLVKEKRVDQADLAWLTDPEVYEVNTIPPHSDHESFQSQEELEEGKSSLVQSLDGNWLIDYAE

NGQGPINFYAEDFDDSNFKSVKVPGNLELQGFGQPQYVNIQYPWDGSEEIFPPQVPSKNPLASYVR

YFDLDEALWDKEVSLKFAGAATAIYVWLNGHFVGYGEDSFTPSEFMVTKFLKKEGNRLAVALYKYSS

ASWLEDQDFWRLSGLFRSVTLEAKPLLHLEDLKLTASLTDNYQKGKLEVEANIAYRLPNASFKLEVR

DSEGDLVAEKVGPIRSEKLGFSLADLPVAAWSAEKPNLYQVRLYLYQAGSLLEVSRQEVGFRNFELK

DGIMYLNGQRIVFKGVNRHEFDSKLGRAITEADMIWDIKTMKQSNINAVRCSHYPNQSLFYRLCDK

YGLYVIDEANLESHGTWEKVGHEDPSFNVPGDDQHWLGASLSRVKNMMARDKNHASILIWSLGN

ESYAGTVFAQMADYVRKADPTRVQHYEGVTHNRKFDDATQIESRMYAPAKEIEEYLTKKPAKPFISV

EYAHAMGNSVGDLAAYTALEKYPHYQGGFIWDWIDQGLEKDGHLLYGGDFDDRPTDYEFCGDGLV

FADRTTSPKLANVKALYSNLKLEVKDGQLFIKNDNLFTNSSAYYFLASLLVDGKLTYQSQPLTFGLEP

GESGTFVLPWPEVEDEKGEIVYQVTAHLKEDLPWADEGFTVAEAEEAVTKLPEFYPAGRPELVDSDF

NLGLKGNGFRILFSKAKGWPVSIKYAGREYLKRLPEFTFWRALTDNDRGAGYGYDLAKWENAGKYA

RLQDISYEIKENSALVKTTFTLPVALKGDLTITYEVDSLGKIAVTANFPGAVENGLLPAFGLNFALPKEL

SDYRYYGLGPNESYADRLEGSYLGIYQGAVEKNFTPYLRPQEAGNRSKVRYYQLFDEEGGLEFTANG

ADLNLSALPYSAAQIEAADHAFELTNNYTWVRALAAQMGVGGDDSWGQKVHPEFCLDAQEARQLK

LVIQPLLLK

SEQ ID No 18: G311
MAHRRTFHWPSLLTESGRGIAFGGDYNPDQWPEDVWDDDIRLMKQAGVNTVALAIFSWDRIQPEK

HRWEFGWLDCIIDKLGKAGIAVDLASATATAPLWLYEQHPEVLPHDKYGHPINAGSRQSWSPTSPV

FKEYALTLCRKLAERYGTNPYVTAWHMGNEYGWNNRYDYCDNALHAFRAWCERKYGTIEALNAAW

GTTFWGQEMNGFDEVLIPRFMGADSMVNPGQKLDFERFGNDMLLDFYRAERDAIAEICPDKPFTTN

FMVSTDQCCMDYADWANEVDFVSNDHYFHEGESHIDELFCSDALMDSLALGRPWYVMEHSTSAV

QWKDLNIRKRKGETVRDSVAHVAMGADAINFFQWRASAFGAESFHSAMVPHAGEHTKLYRSVCEL

GAALKTLGDAGVQGSELVRSDTAILFSAESEWATRSETLPSKKLNHWHDVRDWYRAYLDAGTRAD

IVPLKYDWSGYATVVLPTVLMLSAADTARLERFVRDGGTVVVGYASGLIDENFHTWLGGYPGAGDG

MLRTMLGIRGEEFNILGAQAEGEPSEIRLSNGMVTRLWQNDIAVDGADTEVLASYAGTQADEWELD

-continued

GTAAITRNPYGKGMAYFVGCDLNVADLAVFVGDHLTVGQACEAGDGADYDPTITLHTERASAEAIF

DFYLPRGKNETVVSGISGEPVYRFQCDEGEAPGVYTIRRNGVLVVKRYNRQ

SEQ ID No 19. (G330 domain a)
MEAELKWLDDPEVFRVNQLPAHSDHRFYRDQEEAALEKSSYVQNLNGRWGFKFSKNPMERPVDFY

KLDFDRNDFGEIEVPSEIELSNFAQINYTNITMPWTGKIYRRPAYTLGDNKEEGSFSQGQDNTVGSY

VRHFTLAEGLKNHDVHVVFEGVERAMYVWLNGHFIGYAEDSFTPSEFDLTPYLVDGDNLLAVEVYK

HATSSWIEDQDMFRFSGIFRDVNLVAQPSIHVQDLKINARVADDMKTGSLGLVLKMVGQPGSVQV

EVADQTGAAVLNRQLNADGNWTMAPVQLVGIHLWDNHHPYLYQLTLTVRDATGRVVEVIPYQFGF

RRVEIDQDKVLRLNGKRLIINGVNRHEWNCHRGRAVTIEDMHTDLGIFKENNINAVRTSHYPDQIP

WYYLCDREGIYMMAENNLESHATWQKFGQDEPSYNVPGSLPQWKEAVVDRARSNYEIFKNHTAIL

FWSVGNESYAGEDILAMNNYYKEVDDTRPVHYEGVVHTKEYRDQISDFESWMYLPPKEVEAYLKKN

PDKPFIECEYMHSMGNSVGGMGSYIKLLDKYPQYCGGFIWDFVDQAIEVVDPVTGQKSMRYGGDF

DDHHADNEFSGDGICFADRTPKPAMQEVKYYYGLHK

SEQ ID No 20: (G330 domain b)
MDYTNKLHVVYDDNILGLDGKDFQYLFSYEQGGPESFKIKGKEWLYRSPRPTFWRATTDNDRGNGF

NVSSVQWLAADYVLPCQDIALQVDGKDKKLPLAPKTNRYSNQEFAKKVKITFTYQTQTVPATTVQV

SYTVKASGKIKVNVHYTGAQLPSLPVLGWRMTMPTATSFDYEGLSGETYPDRMAGGIEGTYHVEGL

PVTPYLVPQENGMHMANKWVQITRATTLNNADPDAAPFRLKFEAPKKGKLNFSCLPYTSAELENATH

PEELPAAHRTVLVIAGEVRGVGGIDSWGADVEEKYHIDATVDHDFSFKIVPELN

SEQ ID No 21: G500 (Reference enzyme)
MSCLIPENLRNPKKVHENRLPTRAYYYDQDIFESLNGPWAFALFDAPLDAPDAKNLDWETAKKWSTI

SVPSHWELQEDWKYGKPIYTNVQYPIPIDIPNPPTVNPTGVYARTFELDSKSIESFEHRLRFEGVDNC

YELYVNGQYVGFNKGSRNGAEFDIQKYVSEGENLVVVKVFKWSDSTYIEDQDQWWLSGIYRDVSL

LKLPKKAHIEDVRVTTTFVDSQYQDAELSVKVDVQGSSYDHINFTLYEPEDGSKVYDASSLLNEENG

NTTFSTKEFISFSTKKNEETAFKINVKAPEHWTAENPTLYKYQLDLIGSDGSVIQSIKHHVGFRQVEL

KDGNITVNGKDILFRGVNRHDHHPRFGRAVPLDFVVRDLILMKKFNINAVRNSHYPNHPKVYDLFD

KLGFWVIDEADLETHGVQEPFNRHTNLEAEYPDTKNKLYDVNAHYLSDNPEYEVAYLDRASQLVLRD

VNHPSIIIWSLGNEACYGRNHKAMYKLIKQLDPTRLVHYEGDLNALSADIFSFMYPTFEIMERWRKN

HTDENGKFEKPLILCEYGHAMGNGPGSLKEYQELFYKEKFYQGGFIWEWANHGIEFEDVSTADGKL

HKAYAYGGDFKEEVHDGVFIMDGLCNSEHNPTPGLVEYKKVIEPVHIKIAHGSVTITNKHDFITTDHL

LFIDKDTGKTIDVPSLKPEESVTIPSDTTYVVAVLKDDAGVLKAGHEIAWGQAELPLKVPDFVTETAE

KAAKINDGKRYVSVESSGLHFILDKLLGKIESLKVKGKEISSKFEGSSITFWRPPTNNDEPRDFKNW

KKYNIDLMKQNIHGVSVEKGSNGSLAVVTVNSRISPVVFYYGFETVQKYTIFANKINLNTSMKLTGE

YQPPDFPRVGYEFWLGDSYESFEWLGRGPGESYPDKKESQRFGLYDSKDVEEFVYDYPQENGNHT

DTHFLNIKFEGAGKLSIFQKEKPFNFKISDEYGVDEAAHACDVKRYGRHYLRLDHAIHGVGSEACGP

AVLDQYRLKAQDFNFEFDLAFE

SEQ ID No 22: G600 (Reference enzyme)
MVEDATRSDSTTQMSSTPEVVYSSAVDSKQNRTSDFDANWKFMLSDSVQAQDPAFDDSAWQQV

DLPHDYSITQKYSQSNEAESAYLPGGTGWYRKSFTIDRDLAGKRIAINFDGVYMNATVWFNGVKLG

THPYGYSPFSFDLTGNAKFGGENTIVVKVENRLPSSRWYSGSGIYRDVTLTVTDGVHVGNNGVAIK

TPSLATQNGGNVTMNLTTKVANDTEAAANITLKQTVFPKGGKTDAAIGTVTTASKSIAAGASADVTS

TITAASPKLWSIKNPNLYTVRTEVLNGDTVLDTYDTEYGFRWTGFDATSGFSLNGEKVKLKGVSMH

-continued

HDQGSLGAVANRRAIERQVEILQKMGVNSIRTTHNPAAKALIDVCNEKGVLVVEEVFDMWNRSKN

GNTEDYGKWFGQTIAGDNAVLGGDKDETWAKFDLTSTINRDRNAPSVIMWSLGNEMMEGISGSV

SDFPATSAKLVAWTKAADSTRPMTYGDNKIKANWNESNTMGDNLTANGGVVGTNYSDGANYDKI

RTTHPSWAIYGSETASAINSRGIYNRTTGGAQSSDKQLTSYDNSAVGWGAVASSAWYDVVQRDFV

AGTYVWTGFDYLGEPTPWNGTGSGAVGSWPSPKNSYFGIVDTAGFPKDTYYFYQSQWNDDVHTL

HILPAWNENVVAKGSGNKVPVVVYTDAAKVKLYFTPKGSTEKRLIGEKSFTKKTTAAGYTYQVYEGT

DKDSTAHKNMYLTWNVPWAEGTISAEAYDENNRLIPEGSTEGNASVTTTGKAAKLKADADRKTITA

DGKDLSYIEVDVTDANGHIVPDAANRVTFDVKGAGKLVGVDNGSSPDHDSYQADNRKAFSGKVLA

IVQSTKEAGEITVTAKADGLQSSTVKIATTAVPGTSTEKTVRSFYYSRNYYVKTGNKPILPSDVEVRY

SDGTSDRQNVTWDAVSDDQIAKAGSFSVAGTVAGQKISVRVTMIDEIGALLNYSASTPVGTPAVLP

GSRPAVLPDGTVTSANFAVHWTKPADTVYNTAGTVKVPGTATVFGKEFKVTATIRVQRSQVTIGSS

VSGNALRLTQNIPADKQSDTLDAIKDGSTTVDANTGGGANPSAWTNWAYSKAGHNTAEITFEYAT

EQQLGQIVMYFFRDSNAVRFPDAGKTKIQISADGKNWTDLAATETIAAQESSDRVKPYTYDFAPVG

ATFVKVTVTNADTTTPSGVVCAGLTEIELKTATSKFVTNTSAALSSLTVNGTKVSDSVLAAGSYNTPA

IIADVKAEGEGNASVTVLPAHDNVIRVITESEDHVTRKTFTINLGTEQEFPADSDERD

EXAMPLES

General Material and Methods

Molecular Cloning and Genetic Techniques

Techniques for restriction enzyme digestions, ligation, transformation and other standard molecular biology manipulations were based on methods described in the literature (Maniatis et al. "Molecular cloning: a laboratory manual, 2nd edition" Cold Spring Harbor Laboratory Press, Cold Spring Harbor, NY, 1989; Sambrook and Russell "Molecular Cloning: A Laboratory Manual, 3rd edition" Cold Spring Harbor Laboratory Press, Cold Spring Harbor, NY 2001; Miller "Experiment in molecular genetics" Cold Spring Harbor Laboratory Press, 1972); or as suggested by the manufacturer. The PCR was carried out in a DNA thermal cycler obtained from (Bio-Rad, USA). DNA sequencing was performed by LGC, Berlin, Germany. Proteins were analyzed by polyacrylamide gel electrophoresis (PAGE) under the denaturation conditions using sodium dodecyl sulphate on gels containing 10% SDS (Mini-PRO-TEAN® TGX Stain-free™ gel, Biorad, USA). Protein concentrations were determined using BCA method by following the protocol supplied with the kit.

Bacterial Strains, Plasmid and Growth Conditions

*Escherichia coli* strain TOP10 (Invitrogen) was used for the cloning and isolation of plasmids. The beta-galactosidase deficient *E. coli* strain BW25113 (A(araD-araB)567, ΔlacZ4787(::rrnB-3), Δ-, rph-1, Δ(rhaD-rhaB)568, hsdR514) (Datsenko K A, Wanner B L; 2000, Proc Natl Acad Sci U.S.A. 97: 6640-6645) was used in combination with the pBAD/His vector (obtained from Invitrogen™ Life Technologies Corporation Europe BV) for recombinant protein production.

Growth Media for Protein Expression

2×PY medium containing (16 g/L BD BBL™ Phyton™ Peptone, 10 g/L Yeast Extract, 5 g/L NaCl) was used for the recombinant protein production. The growth medium was supplemented with ampicillin (100 µg/ml) to maintain the plasmid. Protein production was initiated by adding 0.05% of arabinose in to the culture medium.

Example 1: Construction of the Expression Vector for the Production of Lactases The genomic DNA of the lactic acid bacteria or bifidobacteria was extracted using commercial genomic extraction kit by following the supplied protocol (DNeasy, Qaigen, Germany). The lactase gene was amplified by PCR using two synthetic primers, using the purified genomic DNA source as biomass, and the PCR reagents were supplied in the Phusion U Hot start DNA polymerase (Thermo Scientific, USA) kit. The lactase gene was cloned into the start codon of the expression vector pBAD/His using the USER cloning method (Nour-Eldin H H, Geu-Flores F, Halkier B A, Plant Secondary Metabolism Engineering, Methods in Molecular Biology, 643; 2010), resulting in the expression construct. With the USER cloning method long complementary overhangs in both PCR product and destination vector were generated. These overhangs can anneal to each other to form a stable hybridization product which was used to transform into *E. coli* without ligation. For the generation of overhangs in the PCR product, a single deoxyuradine residue is included in the upstream region of each primer to amplify target DNA. The lactase gene was amplified using the forward primer (5'-ATTAAC-CAUGCGACGCAACTTCGAATGGCC-3' (SEQ ID NO: 23)) and reverse primer (ATCTTCTCUTTACCGCCTTAC-CACGAGCACG (SEQ ID NO: 24) containing a uridine at 9th position (as shown in bold), followed by with the lactase gene sequence. In parallel, the vector DNA was PCR amplified using the forward (5'-AGAGAAGAUTTTCAGCCT-GATACAGATTAAATC-3' (SEQ ID NO: 25) and reverse primer (5'-ATGGTTAAUTCCTCCTGTTAGCC-CAAAAAACGG-3' (SEQ ID NO: 26)) pair containing single deoxyuracil residue at 9th positions (as highlighted in bold) followed by vector DNA sequence. The PCR products were purified using the commercial PCR purification kit (Qiagen, Denmark). The purified PCR products (lactase gene and the vector DNA) were mixed in equimolar amount and incubated with a commercial USER enzyme mix (New England Biolabs, USA) by following the supplied protocol. These enzymes remove the uracil residue and also the short fragment upstream of the uridine, thereby creating complementary overhang in the PCR products. These complementary overhangs anneal with each other resulting in the pBAD-lactase expression vector. Aliquots of the ligation mixture were transformed into chemically competent E. coli TOP 10 cells. Transformants were selected at 37° C. on LB-Amp plates (LB; Luria-Bertani, Amp; 100 µg/ml ampicillin). The following day, colony PCR was carried out using a small biomass from the overnight grown transformant using the vector primers (primer 1; 5'-CGGCGT-CACACTTTGCTATGCC-3' (SEQ ID NO: 27) and primer 2; 5'-CCGCGCTACTGCCGCCAGGC-3' (SEQ ID NO: 28)). The positive clones from the colony PCR were cultured in 5 mL LB-Amp medium and plasmid DNA was isolated from the cells. The cloned lactase gene was sequenced to verify that no additional mutations had been introduced during the amplification of the gene. The plasmid DNA was transformed in to the expression host E. coli strain BW25113.

Example 2: Expression of Lactases in E. coli Expression Host

The lactase enzyme was produced in E. coli BW25113 using the pBAD expression system. Freshly transformed E. coli BW25113 cells carrying the plasmid DNA were collected from a Lb-Amp plate using a sterile loop and used to inoculate 5 mL of Lb-Amp medium. The overnight grown culture (200 µL) was used to inoculate 50 mL 2×PY medium (containing 100 µg/mL ampicillin) in a 250 mL flask in a shaker (Innova® 42). The culture was grown at 37° C. at 220 rpm until the OD600 reached between 0.6-0.8. The lactase expression was initiated by adding 0.05% arabinose into the culture medium and the cells were cultured for additional 16-20 hours at 18° C. at 180 rpm. Cells were harvested by centrifugation (5000 rpm, 10 min at 4° C.) and were stored at −20° C. until further use.

Example 3: Activity Determination Using Enzymes on Lactose as Substrate at pH 6.7 at 37° C.

To measure the beta-galactosidase activity, the lactases were diluted to 40× in buffer A (50 mM $NaH_2PO_4$ buffer pH 6.7 containing 100 µM of $MgSO_4$). In a separate reaction, the diluted enzyme was incubated with lactose solution prepared in buffer B (140 mM of lactose prepared in 100 mM sodium-citrate buffer of pH 6.7, containing 100 µM of $MgSO_4$). The reaction mixture was prepared by mixing 13 µL of diluted enzyme and 37 µL of lactose solution in a PCR tube. The reaction mixture was incubated in a DNA thermal cycler with the following incubation parameters (reaction time; 10 min at 37° C., enzyme inactivation; 10 min at 95° C., cooling; 4° C.). The reaction mixtures were stored at −20° C. until further use. To determine the amount of glucose formed during the reaction, 10 µL of the reaction mixture was transferred to one well of standard microtiter plate (Thermo Fischer Scientific, Denmark) containing 80 µL of buffer C (100 mM of $NaH_2PO_4$ buffer, pH 7.0, containing glucose oxidase; 0.6 g/L (Sigma Aldrich), 2,2'-azino-bis(3-ethylbenzothiazoline-6-sulfonic acid diammonium salt); ABTS: 1.0 g/L (Sigma Aldrich), horseradish peroxidase; 0.02 g/L (Sigma Adrich)) and incubated at 30° C. for 40 min. After 40 min, the absorbance was determined at 610 nm using SpectroStar Omega UV-plate reader (BMG Labtech, Germany). The absorbance values between 0.1 and 1.5 were used for calculations, if the A610 nm value>1.5, the reaction mixture was diluted up to 10× with buffer A. With each enzyme, the reactions were carried out in triplicate and the mean value of the triplicate measurement was used for calculation. The protein purification performed with the E. coli cells transformed with the empty pBAD/His was used for normalization. Using a known concentration of glucose (0-2.5 mM), a standard curve was drawn, and the slope of the curve was used to calculate the glucose formed during the reaction. The maximum absorbance value for each lactase was used to determine µmol of glucose formed per minute, described as 1 Unit of Activity with Lactose at pH 6.7 at 37° C. The activity of reference sequences SEQ ID NO:21 and SEQ ID NO:22 were determined under the similar conditions.

Example 4: Activity Determination Using Enzymes on Lactose as Substrate at pH 5.5 at 37° C.

The lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer E (140 mM of lactose prepared in 100 mM sodium-citrate buffer of pH 5.5, containing 100 µM of $MgSO_4$). The reaction mixture was prepared by mixing 13 µL of diluted enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). The reaction mixtures were stored at −20° C. until further use. The maximum absorbance value for each lactase was used to determine µmol of glucose formed per minute, described as 1 Unit of Activity with Lactose at pH 5.5 at 37° C. The maximum absorbance value for each lactase was used to determine µmol of glucose formed per minute, described as 1 Unit of Activity with Lactose at pH 5.5 at 37° C. The activity of reference sequences SEQ ID NO:21 and SEQ ID NO:22 were determined under the similar conditions.

Example 5: Activity Determination Using Enzymes on Lactose as Substrate at pH 4.5 at 37° C.

The lactases were diluted up to 40× in buffer A (50 mM $NaH_2PO_4$ buffer pH 6.7 containing 100 µM of $MgSO_4$). In a separate reaction, the diluted enzyme was incubated with lactose solution prepared in buffer F (140 mM of lactose prepared in 100 mM sodium-citrate buffer of pH 4.5, containing 100 µM of $MgSO_4$). The reaction mixture was prepared by mixing 13 µL of diluted enzyme and 37 µL of lactose solution in a PCR tube. The reaction mixture was incubated in a DNA thermal cycler using the following incubating parameters (reaction time; 10 min at 37° C., enzyme inactivation; 10 min at 95° C., storage; 4° C.). The maximum absorbance value for each lactase was used to determine µmol of glucose formed per minute, described as 1 Unit of Activity with Lactose at pH 4.5 at 37° C. The maximum absorbance value for each lactase was used to determine µmol of glucose formed per minute, described as 1 Unit of Activity with Lactose at pH 4.5 at 37° C. The activity of reference sequences SEQ ID NO:21 and SEQ ID NO:22 were determined under the similar conditions.

The invention claimed is:

1. A process for producing a lactose-free or low-lactose acidified milk product, comprising:
   (a) acidifying a milk base to obtain an acidified milk product having a pH of 3.0 to 5.0, and
   (b) before, during, or after step (a), adding a bacterial peptide to the milk base or acidified milk product, wherein the bacterial peptide exhibits beta-galactosidase enzyme activity which has an activity optimum at a pH of below pH 6.7 and wherein the bacterial peptide is selected from peptides having the amino acid sequence of any one of SEQ ID NOs. 1, 2, 3 and 14, and
   wherein the acidified milk product has a lower lactose level than an acidified milk product produced by a process where no bacterial peptide is added, but is otherwise identical to the process as claimed.

2. The process according to claim 1, wherein the bacterial peptide has an optimum beta-galactosidase activity at a pH of below pH 5.5 when measured at 37° C.

3. The process according to claim 1, wherein the bacterial peptide is derived from a lactic acid bacterium of a genus selected from *Lactococcus, Lactobacillus*, and *Streptococcus*.

4. The process according to claim 1, wherein activity of the bacterial peptide is determined by preparing a reaction mixture comprising (i) 13 μL of a diluted bacterial peptide composition comprising the bacterial peptide diluted in 50 mM $NaH_2PO_4$ buffer at pH 6.7 containing 100 μM of $MgSO_4$ and (ii) 37 μL of a lactose solution comprising 140 mM of lactose in 100 mM sodium-citrate buffer at pH 4.5 containing 100 μM of $MgSO_4$ and incubating the reaction mixture for 10 min at 37° C.

5. The process according to the claim 1, further comprising subjecting the acidified milk product to a heat treatment so as to reduce the level of bacteria in the acidified milk product to no more than $1 \times 10^2$ colony forming units (CFU) per g, to obtain a heat treated acidified milk product.

6. The process according to claim 5, wherein the bacterial peptide is added after the acidifying step, prior to the heat treatment.

7. The process according to claim 1, further comprising storing the acidified milk product comprising the bacterial peptide at a temperature of at least 20° C. for at least 1 day.

8. The process according to claim 1, wherein the acidifying comprises one or more of adding a chemical acidifier and fermenting with a lactic acid bacterium starter culture.

9. The process according to claim 1, wherein the bacterial peptide is added during or after the acidifying step.

10. The process according to claim 1, wherein the bacterial peptide has an optimum beta-galactosidase activity at a pH of from 3 to 5 when measured at 37° C.

11. The process according to claim 1, further comprising storing the acidified milk product comprising the bacterial peptide at a temperature of at least 20° C. for at least 3 days.

12. A process according to claim 1, wherein the bacterial peptide has the amino acid sequence of SEQ ID NO: 1.

13. The process according to claim 1, wherein the bacterial peptide has the amino acid sequence of SEQ ID NO: 2.

14. The process according to claim 1, wherein the bacterial peptide has the amino acid sequence of SEQ ID NO: 3.

15. The process according to claim 1, wherein the bacterial peptide has the amino acid sequence of SEQ ID NO: 14.

* * * * *